US009163017B2

(12) United States Patent
Degoey et al.

(10) Patent No.: US 9,163,017 B2
(45) Date of Patent: *Oct. 20, 2015

(54) ANTI-VIRAL COMPOUNDS

(71) Applicant: ABBVIE INC., North Chicago, IL (US)

(72) Inventors: David A. Degoey, Salem, WI (US);
Pamela L. Donner, Mundelein, IL (US);
Warren M. Kati, Gurnee, IL (US);
Charles W. Hutchins, Green Oaks, IL (US); Mark A. Matulenko, Libertyville, IL (US); Tammie K. Jinkerson, Pleasant Prairie, WI (US); Ryan G. Keddy, Beach Park, IL (US)

(73) Assignee: ABBVIE INC., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/021,435

(22) Filed: Sep. 9, 2013

(65) Prior Publication Data
US 2014/0213601 A1    Jul. 31, 2014

Related U.S. Application Data

(63) Continuation of application No. 12/644,427, filed on Dec. 22, 2009, now Pat. No. 8,541,424.

(60) Provisional application No. 61/140,262, filed on Dec. 23, 2008.

(51) Int. Cl.
*C07D 471/04*    (2006.01)

(52) U.S. Cl.
CPC .................... *C07D 471/04* (2013.01)

(58) Field of Classification Search
CPC .................................................. C07D 471/04
USPC ..................................... 514/264.11; 544/279
See application file for complete search history.

(56) References Cited

U.S. PATENT DOCUMENTS

| | | | |
|---|---|---|---|
| 5,830,867 A | 11/1998 | Bhatnagar et al. | |
| 5,935,982 A | 8/1999 | Dykstra et al. | |
| 6,235,493 B1 | 5/2001 | Bissell et al. | |
| 6,369,091 B1 | 4/2002 | Sircar et al. | |
| 6,703,403 B2 | 3/2004 | Norbeck et al. | |
| 6,780,529 B2 | 8/2004 | Kimura | |
| 6,881,741 B2 | 4/2005 | Kong et al. | |
| 6,919,366 B2 | 7/2005 | Sircar et al. | |
| 7,141,574 B2 | 11/2006 | Beaulieu et al. | |
| 7,183,270 B2 * | 2/2007 | Cherney et al. | 514/210.18 |
| 7,659,270 B2 | 2/2010 | Bachand et al. | |
| 7,704,992 B2 | 4/2010 | Bachand et al. | |
| 7,728,027 B2 | 6/2010 | Pack et al. | |
| 7,741,347 B2 | 6/2010 | Bachand et al. | |
| 7,745,636 B2 | 6/2010 | Bachand et al. | |
| 7,759,495 B2 | 7/2010 | Bachand et al. | |
| 7,763,731 B2 | 7/2010 | Rockway et al. | |
| 7,906,655 B2 | 3/2011 | Belema et al. | |
| 8,034,966 B1 | 10/2011 | Lalezari | |
| 8,101,643 B2 | 1/2012 | Qiu et al. | |
| 8,546,405 B2 * | 10/2013 | DeGoey et al. | 514/256 |
| 2002/0183319 A1 | 12/2002 | Liang et al. | |
| 2003/0004203 A1 | 1/2003 | Sircar et al. | |
| 2003/0100582 A1 | 5/2003 | Sircar et al. | |
| 2005/0059650 A1 | 3/2005 | Jones et al. | |
| 2005/0075343 A1 | 4/2005 | Sircar et al. | |
| 2005/0197375 A1 | 9/2005 | Sircar et al. | |
| 2006/0003942 A1 | 1/2006 | Tung et al. | |
| 2006/0058317 A1 | 3/2006 | Gravestock et al. | |
| 2006/0105997 A1 | 5/2006 | Arrington et al. | |
| 2006/0135773 A1 | 6/2006 | Semple et al. | |
| 2007/0004741 A1 | 1/2007 | Apodaca et al. | |
| 2007/0142434 A1 | 6/2007 | Sandanayaka et al. | |
| 2007/0197558 A1 | 8/2007 | Betebenner et al. | |
| 2007/0232672 A1 | 10/2007 | Betebenner et al. | |
| 2007/0232645 A1 | 10/2007 | Rockway et al. | |
| 2007/0299068 A1 | 12/2007 | Karp et al. | |
| 2008/0044379 A1 | 2/2008 | Bachand et al. | |
| 2008/0044380 A1 | 2/2008 | Bachand et al. | |
| 2008/0050336 A1 | 2/2008 | Bachand et al. | |
| 2008/0221107 A1 | 9/2008 | Giordanetto et al. | |
| 2008/0292589 A1 | 11/2008 | Anilkumar et al. | |
| 2008/0299075 A1 | 12/2008 | Bachand et al. | |
| 2008/0311075 A1 | 12/2008 | Bachand et al. | |
| 2009/0004111 A1 | 1/2009 | Rice et al. | |
| 2009/0041716 A1 | 2/2009 | Kim et al. | |
| 2009/0043107 A1 | 2/2009 | Pack et al. | |
| 2009/0047247 A1 | 2/2009 | Qiu et al. | |

(Continued)

FOREIGN PATENT DOCUMENTS

BR    PI 0401908-3 A    1/2006
CN    1292697 A    4/2001

(Continued)

OTHER PUBLICATIONS

Liu et al., "Discovery of a Novel CCR5 Antagonist Lead Compound Through Fragment Assembly," Molecules 13:2426-2441 (2008).

Office Action in Chinese Application No. 201080026637.8 dated Aug. 28, 2014.

Notice of Allowance in Russian Application No. 2011156145 dated Sep. 29, 2014.

Adjabeng G., et al., "Novel Class of Tertiary Phosphine Ligands Based on a Phosphaadamantane Framework and use in the Suzuki cross-Coupling Reactions of Aryl Halides Under Mild Conditions," Organic Letters, 2003, vol. 5(6), pp. 953-955.

(Continued)

*Primary Examiner* — Erich A Lesser

(74) *Attorney, Agent, or Firm* — J.A. Lindeman & Co., PLLC

(57) ABSTRACT

Compounds effective in inhibiting replication of Hepatitis C virus ("HCV") are described. This invention also relates to processes of making such compounds, compositions comprising such compounds, and methods of using such compounds to treat HCV infection.

26 Claims, No Drawings

(56) References Cited

U.S. PATENT DOCUMENTS

| | | |
|---|---|---|
| 2009/0068140 A1 | 3/2009 | Bachand et al. |
| 2009/0093456 A1 | 4/2009 | Arnold et al. |
| 2009/0104151 A1 | 4/2009 | Hanson et al. |
| 2009/0202478 A1 | 8/2009 | Bachand et al. |
| 2009/0202483 A1 | 8/2009 | Bachand et al. |
| 2010/0055071 A1 | 3/2010 | Leivers et al. |
| 2010/0068176 A1 | 3/2010 | Belema et al. |
| 2010/0068197 A1 | 3/2010 | Anderson et al. |
| 2010/0080772 A1 | 4/2010 | Belema et al. |
| 2010/0143499 A1 | 6/2010 | Condon |
| 2010/0158862 A1 | 6/2010 | Kim et al. |
| 2010/0160355 A1 | 6/2010 | DeGoey et al. |
| 2010/0168138 A1 | 7/2010 | DeGoey et al. |
| 2010/0215616 A1 | 8/2010 | Romine et al. |
| 2010/0215618 A1 | 8/2010 | Carter et al. |
| 2010/0221214 A1 | 9/2010 | Or et al. |
| 2010/0221215 A1 | 9/2010 | Qiu et al. |
| 2010/0221216 A1 | 9/2010 | Or et al. |
| 2010/0226882 A1 | 9/2010 | Or et al. |
| 2010/0226883 A1 | 9/2010 | Qiu et al. |
| 2010/0233120 A1 | 9/2010 | Bachand et al. |
| 2010/0233122 A1 | 9/2010 | Qiu et al. |
| 2010/0249190 A1 | 9/2010 | Lopez et al. |
| 2010/0260708 A1 | 10/2010 | Belema et al. |
| 2010/0260715 A1 | 10/2010 | Or et al. |
| 2010/0266543 A1 | 10/2010 | Qiu et al. |
| 2010/0267634 A1* | 10/2010 | Donner et al. .......... 514/10 |
| 2010/0303755 A1 | 12/2010 | Lopez et al. |
| 2010/0310512 A1 | 12/2010 | Guo et al. |
| 2010/0316607 A1 | 12/2010 | Or et al. |
| 2010/0317568 A1 | 12/2010 | DeGoey et al. |
| 2011/0008288 A1 | 1/2011 | Or et al. |
| 2011/0064695 A1 | 3/2011 | Qiu et al. |
| 2011/0064696 A1 | 3/2011 | Or et al. |
| 2011/0064697 A1 | 3/2011 | Qiu et al. |
| 2011/0064698 A1 | 3/2011 | Or et al. |
| 2011/0070196 A1 | 3/2011 | Qiu et al. |
| 2011/0070197 A1 | 3/2011 | Or et al. |
| 2011/0077280 A1 | 3/2011 | Bender et al. |
| 2011/0092415 A1 | 4/2011 | DeGoey et al. |
| 2011/0112100 A1 | 5/2011 | Milbank et al. |
| 2011/0136799 A1 | 6/2011 | Chern et al. |
| 2011/0142798 A1 | 6/2011 | Qiu et al. |
| 2011/0150827 A1 | 6/2011 | Dousson et al. |
| 2011/0152246 A1 | 6/2011 | Buckman et al. |
| 2011/0172238 A1 | 7/2011 | Henderson et al. |
| 2011/0189129 A1 | 8/2011 | Qiu et al. |
| 2011/0195044 A1 | 8/2011 | Romine et al. |
| 2011/0207699 A1 | 8/2011 | DeGoey et al. |
| 2011/0217261 A1 | 9/2011 | Or et al. |
| 2011/0218175 A1 | 9/2011 | Or et al. |
| 2011/0223134 A1 | 9/2011 | Nair et al. |
| 2011/0237579 A1 | 9/2011 | Li et al. |
| 2011/0237636 A1 | 9/2011 | Belema et al. |
| 2011/0274648 A1 | 11/2011 | Lavoie et al. |
| 2011/0281910 A1 | 11/2011 | Lavoie et al. |
| 2011/0286961 A1 | 11/2011 | Belema et al. |
| 2011/0294819 A1 | 12/2011 | Lopez et al. |
| 2011/0300104 A1 | 12/2011 | Qiu et al. |
| 2012/0004196 A1 | 1/2012 | DeGoey et al. |
| 2012/0028978 A1 | 2/2012 | Zhong et al. |
| 2012/0040977 A1 | 2/2012 | Li et al. |
| 2012/0115918 A1 | 5/2012 | DeGoey et al. |
| 2012/0172290 A1 | 7/2012 | Krueger et al. |
| 2012/0220562 A1 | 8/2012 | DeGoey et al. |

FOREIGN PATENT DOCUMENTS

| | | |
|---|---|---|
| CN | 1585756 A | 2/2005 |
| DE | 75755 C | 6/1894 |
| EA | 010023 B1 | 8/2006 |
| EA | 7722 B1 | 12/2006 |
| EP | 2242751 A1 | 8/2009 |
| JP | 2003282270 | 10/2003 |
| JP | 2010126571 A | 6/2010 |
| RU | 2286343 | 7/2004 |
| RU | 2006106272 A | 8/2006 |
| WO | WO 94/27627 A1 | 12/1994 |
| WO | WO 99/59587 A1 | 11/1999 |
| WO | WO 99/61020 A1 | 12/1999 |
| WO | WO 00/12521 A1 | 3/2000 |
| WO | WO 02/14314 A2 | 2/2002 |
| WO | WO 02/48147 A2 | 6/2002 |
| WO | WO 03/040112 A1 | 5/2003 |
| WO | WO 03/082186 A2 | 10/2003 |
| WO | WO 2004/005283 A1 | 1/2004 |
| WO | WO 2004/014313 A2 | 2/2004 |
| WO | WO 2004/014852 A2 | 2/2004 |
| WO | WO 2004/014852 A3 | 4/2004 |
| WO | WO 2005/007658 A2 | 1/2005 |
| WO | WO 2005/012288 A1 | 2/2005 |
| WO | 2005026129 A1 | 3/2005 |
| WO | 2005054199 A1 | 6/2005 |
| WO | WO 2004/014313 A3 | 12/2005 |
| WO | WO 2006/020951 A1 | 2/2006 |
| WO | WO 2006/033703 A1 | 3/2006 |
| WO | 2006079833 A1 | 8/2006 |
| WO | 2006113769 A1 | 10/2006 |
| WO | WO 2006/133326 A1 | 12/2006 |
| WO | WO 2007/070556 A2 | 6/2007 |
| WO | WO 2007/070600 A2 | 6/2007 |
| WO | WO 2007/076034 A2 | 7/2007 |
| WO | WO 2007/076035 A2 | 7/2007 |
| WO | WO 2007/082554 A1 | 7/2007 |
| WO | WO 2007/070556 A3 | 8/2007 |
| WO | WO 2007/081517 C1 | 9/2007 |
| WO | WO 2007/070600 A3 | 11/2007 |
| WO | WO 2007/131366 A1 | 11/2007 |
| WO | WO 2007/144174 A1 | 12/2007 |
| WO | WO 2008/014236 A1 | 1/2008 |
| WO | WO 2008/014238 A2 | 1/2008 |
| WO | 2008021388 A1 | 2/2008 |
| WO | WO 2008/021927 A2 | 2/2008 |
| WO | WO 2008/021928 A2 | 2/2008 |
| WO | WO 2008/021936 A2 | 2/2008 |
| WO | WO 2008/021928 A3 | 3/2008 |
| WO | WO 2008/021936 A3 | 4/2008 |
| WO | WO 2008/021927 A3 | 5/2008 |
| WO | WO 2008/064218 A2 | 5/2008 |
| WO | WO 2008/070447 A2 | 6/2008 |
| WO | WO 2008/074450 A2 | 6/2008 |
| WO | WO 2008/064218 A3 | 10/2008 |
| WO | WO 2008/128121 A1 | 10/2008 |
| WO | 2008144463 A1 | 11/2008 |
| WO | WO 2008/133753 A2 | 11/2008 |
| WO | WO 2008/144380 A1 | 11/2008 |
| WO | 2008154271 A1 | 12/2008 |
| WO | WO 2009/003009 A1 | 12/2008 |
| WO | WO 2009/020534 A2 | 2/2009 |
| WO | WO 2009/020825 A1 | 2/2009 |
| WO | WO 2009/020828 A1 | 2/2009 |
| WO | WO 2008/070447 A3 | 3/2009 |
| WO | WO 2009/093082 A1 | 7/2009 |
| WO | WO 2009/094224 A1 | 7/2009 |
| WO | WO 2009/102318 A1 | 8/2009 |
| WO | WO 2009/102325 A1 | 8/2009 |
| WO | WO 2009/102568 A1 | 8/2009 |
| WO | WO 2009/102633 A1 | 8/2009 |
| WO | WO 2009/102694 A1 | 8/2009 |
| WO | WO 2009/136290 A1 | 11/2009 |
| WO | WO 2009/143361 A1 | 11/2009 |
| WO | WO 2009/155709 A1 | 12/2009 |
| WO | WO 2010/015090 A1 | 2/2010 |
| WO | WO 2010/017401 A1 | 2/2010 |
| WO | WO 2010/039793 A1 | 4/2010 |
| WO | WO 2010/059858 A1 | 5/2010 |
| WO | WO 2010/062821 A1 | 6/2010 |
| WO | WO 2010/065674 A1 | 6/2010 |
| WO | WO 2010/065681 A1 | 6/2010 |
| WO | WO 20101065668 A1 | 6/2010 |
| WO | WO 2010/075376 A2 | 7/2010 |
| WO | WO 2010/075380 A1 | 7/2010 |
| WO | WO 2010/091413 A1 | 8/2010 |

(56) References Cited

FOREIGN PATENT DOCUMENTS

| | | |
|---|---|---|
| WO | WO 2010/096302 A1 | 8/2010 |
| WO | WO 2010/096462 A1 | 8/2010 |
| WO | WO 2010/096777 A1 | 8/2010 |
| WO | WO 2010/099527 A1 | 9/2010 |
| WO | WO 2010/111483 A1 | 9/2010 |
| WO | WO 2010/111534 A1 | 9/2010 |
| WO | WO 2010/111673 A1 | 9/2010 |
| WO | WO 2010/115767 A1 | 10/2010 |
| WO | WO 2010/117635 A1 | 10/2010 |
| WO | WO 2010/117704 A1 | 10/2010 |
| WO | WO 2010/117977 A1 | 10/2010 |
| WO | WO 2010/120621 A1 | 10/2010 |
| WO | WO 2010/120935 A1 | 10/2010 |
| WO | WO 2010/122162 A1 | 10/2010 |
| WO | WO 2010/132538 A1 | 11/2010 |
| WO | WO 2010/132601 A1 | 11/2010 |
| WO | WO 2010/138368 A1 | 12/2010 |
| WO | WO 2010/138488 A1 | 12/2010 |
| WO | WO 2010/138790 A1 | 12/2010 |
| WO | WO 2010/138791 A1 | 12/2010 |
| WO | WO 2010/144646 A2 | 12/2010 |
| WO | WO 2010/148006 A1 | 12/2010 |
| WO | WO 2011/004276 A1 | 1/2011 |
| WO | WO 2011/009084 A2 | 1/2011 |
| WO | WO 2011/015658 A1 | 2/2011 |
| WO | WO 2011/026920 A1 | 3/2011 |
| WO | WO 2011/028596 A1 | 3/2011 |
| WO | WO 2011/031904 A1 | 3/2011 |
| WO | WO 2011/031934 A1 | 3/2011 |
| WO | WO 2011/050146 A1 | 4/2011 |
| WO | WO 2011/054834 A1 | 5/2011 |
| WO | WO 2011/059850 A1 | 5/2011 |
| WO | WO 2011/059887 A1 | 5/2011 |
| WO | WO 2011/060000 A1 | 5/2011 |
| WO | WO 2011/066241 A1 | 6/2011 |
| WO | WO 2011/068941 A2 | 6/2011 |
| WO | WO 2011/075439 A1 | 6/2011 |
| WO | WO 2011/075607 A1 | 6/2011 |
| WO | WO 2011/075615 A1 | 6/2011 |
| WO | WO 2011/079327 A1 | 6/2011 |
| WO | WO 2011/081918 A1 | 7/2011 |
| WO | WO 2011/082077 A1 | 7/2011 |
| WO | WO 2011/087740 A1 | 7/2011 |
| WO | WO 2011/091417 A1 | 7/2011 |
| WO | WO 2011/091446 A1 | 7/2011 |
| WO | WO 2011/091532 A1 | 8/2011 |
| WO | WO 2011/112429 A1 | 9/2011 |
| WO | WO 2011/119853 A1 | 9/2011 |
| WO | WO 2011/119858 A1 | 9/2011 |
| WO | WO 2011/119860 A1 | 9/2011 |
| WO | WO 2011/119870 A1 | 9/2011 |
| WO | WO 2011/127350 A1 | 10/2011 |
| WO | WO 2011/146401 A1 | 11/2011 |
| WO | WO 2011/150243 A1 | 12/2011 |
| WO | WO 2011/156543 A2 | 12/2011 |
| WO | WO 2011/156578 A1 | 12/2011 |
| WO | WO 2012/051361 A1 | 4/2012 |
| WO | WO 2012/083164 A1 | 6/2012 |
| WO | WO 2012/083170 A1 | 6/2012 |

OTHER PUBLICATIONS

Adjabeng G., et al., "Palladium Complexes of 1,3,5,7-tetramethyl-2,4,8-trioxa-6-phenyl-6-phosphaadamantane: Synthesis, Crystal Structure and Use in the Suzuki and Sonogashira Reactions and the Alpha-arylation of Ketones," The Journal of Organic Chemistry, 2004, vol. 69(15), pp. 5082-5086.

Aldous D.J., et al., "A Simple Enantioselective Preparation of (2S,5S)-2,5-diphenylpyrrolidine and Related Diaryl Amines," Tetrahedron Asymmetry, 2000, vol. 11, pp. 2455-2462.

Alesso E.N., et al., "Synthesis of Diastereoisomeric 1,2,3-Triphenylindans," Australian Journal of Chemistry, 1997, vol. 50, pp. 149-152.

Angiolini M., et al., "Synthesis of Azabicycloalkane Amino Acid Scaffolds as Reverse-Turn Inducer Dipeptide Mimics," European Journal Organization Chemistry, 2000, pp. 2571-2581.

Boehm T., et al., "Uber Die Bildung Von Gamma-Piperidonderivaten Aus Azetessigester, Aromatischen Aldehyden und Aminen, Eine Modifikation Der Hantzschschen Pyridinsynthese," Pharmaceutical, 1943, vol. 281, pp. 62-77.

Brettle R., et al., "A Highly Efficient Enzymic Route to Novel Chiral Liquid Crystals based on 3-Aryl-2-cycloalken-1-ones," Journal of the Chemical Society, Chemical Communications, 1994, pp. 2305-2306.

Bundgaard H., "Design of Pro Drugs," 1985, pp. 1-6.

Bundgaard H., "Design of prodrugs," pp. 7-9 & 21-24, 1985.

Carlo et al., "Synthetic Exploitation of the Ring-Opening of 3,4-Dinitrothiophene, IX[?)Pyrrolidines, Pyrrolines and Pyrroles from 1,4-Diaryl-2,3-dinitro-1,3-butadienes via a 5-endo-trig Cyclization", European Journal of Organic Chemistry, 2000(6), 903-912, 2000.

Charifson P.S., et al., "Novel Dual-Targeting Benzimidazole Urea Inhibitors of DNA Gyrase and Topoisomerase IV Possessing Potent Antibacterial Activity: Intelligent Design and Evolution through the Judicious Use of Structure-Guided Design and Structure-Activity Relationships," Journal of Medicinal Chemistry, 2008, vol. 51(17), pp. 5243-5263.

Chong J.M., et al., "Asymmetric Synthesis of trans.2,5-Diphenylpyrrolidine: A C2-Symmetric Chiral Amine," Tetrahedron Asymmetry, 1995, vol. 6(2), pp. 409-418.

Clark W.M., et al., "A Highly Enantioselective Conjugate Reduction of 3-Arylinden-1-ones Using Bakers' Yeast for the Preparation of (S)-3-Arylindan-1-ones," Organic Letters, 1999, vol. 1(11), pp. 1839-1842.

Clarke et al., "Pot, atom and step economic (PASE) synthesis of highly functionalized piperidines: a ?ve-component condensation", Tetrahedron Letters, 48(30), 5209-5212, 2007.

Clarke et al., "Pot, Atom and Step Economic (PASE) Synthesis of Highly Substituted Piperidines: A Five-Component Condensation", Synthesis, 21, 3530.

Collado I., et al., "Stereoselective Addition of Grignard-Derived Organocopper Reagents to N-Acyliminium Ions: Synthesis of Enantiopure 5- and 4,5-Substituted Prolinates," Journal of Organic Chemistry, 1995, vol. 60, pp. 5011-5015.

Conte I., et al., "Synthesis and SAR of Piperazinyl-N-Phenylbenzamides as Inhibitors of Hepatitis C Virus RNA Replication in Cell Culture," Bioorganic and Medicinal Chemistry Letters, 2009, vol. 19(6), pp. 1779-1783.

Dell'Erba C., et al., "Synthetic Exploitation of the Ring-Opening of 3,4-Dinitrothiophene, IX Pyrrolidines, Pyrrolines and Pyrroles from 1,4-Diaryl-2,3-Dinitro-1,3-Butadienes Via a 5-Endo-Trig Cyclization," European Journal of Organic Chemistry, 2000, pp. 903-912.

Effenberger F., et al., "Synthesis, Structure, and Spectral Behavior of Donor-Acceptor Substituted Biphenyls," The Journal of Organic Chemistry, 1983, vol. 48, pp. 4649-4658.

Fan X., et al., "An Efficient and Practical Synthesis of the HIV Protease Inhibitor 159 Atazanavir via a Highly Diastereoselective Reduction Approach," Organic Process Research and Development, 2008, vol. 12(1), pp. 69-75.

Fiedler, "Encyclopedia of Excipients for Pharmaceuticals, Cosmetics and related Areas," 5th Edition, Hoepfner E.M., et al., eds., Editio Cantor Verlag Aulendorf, 2002, Table of Contents.

Gordon T.D., et al, "Synthetic Approaches to the Azole Peptide Mimetics," Tetrahedron Letters, 1993, vol. 34(12), pp. 1901-1904.

Greene T.W. et al., "Protective Groups in Organic Synthesis," 1999, Ed. 3, John Wiley & Sons, pp. 494-653.

Hartwig J.F., et al., "111.3.2 Palladium-Catalyzed Amination of Aryl Halides and Related Reactions," Handbook of Organopalladium Chemistry for Organic Synthesis, 2002, pp. 1051-1096.

Hoover J.E, Remington's Pharmaceutical Sciences, Tbl of Cont, 1975.

Jacques et al., "Enantiomers, Racemates, and Resolutions," J. Wiley & Sons, Chapter 3, pp. 197-213, 1981.

Jeffrey J.L., et al., "Concise Synthesis of Pauciflorol F Using a Larock Annulation," Organic Letters, 2009, vol. 11(23), pp. 5450-5453.

Jing Q., et al., "Bulky Achiral Triarylphosphines Mimic BINAP in Ru(II)-Catalyzed Asymmetric Hydrogenation of Ketones," Advanced Synthesis & Catalysis, 2005, vol. 347, pp. 1193-1197.

(56) References Cited

OTHER PUBLICATIONS

Khan et al., "Effects of Substituents in the ?-Position of 1,3-Dicarbonyl Compounds in Bromodimethylsulfonium Bromide-Catalyzed Multicomponent Reactions: A Facile Access to Functionalized Piperidines", Journal of organic chemistry, 73(21), 8398-8402 2008.
Kuethe J.T., et al., "Asymmetric Synthesis of 1,2,3-Trisubstituted Cyclopentanes and Cyclohexanes as Key Components of Substance P Antagonists," The Journal of Organic Chemistry, 2002, vol. 67(17), pp. 5993-6000.
Lachman L., et al., Pharmaceutical Dosage Forms: Tablets, vol. 3, 1990, Informa Healthcare, Table of Contents.
Li Chuan-Ying., et al., "Olefination of Ketones for the Enantioselective Synthesis of Allenes via an Ylide Route," Tetrahedron, 2007, vol. 63, pp. 8046-8053.
Lieberman L., et al., eds., Pharmaceutical Dosage Forms, vol. 1, Marcel Dekker, Inc., 1980, Table of Contents.
Louie J., et al., "Palladium-Catalyzed Amination of Aryl Triflates and Importance of Triflate Addition Rate," Journal of Organic Chemistry, 1997, vol. 62(5), pp. 1268-1273.
L-selectride, Retrieved from the Internet: <URL: http://en.wikipedia.org/w/index.php?0ldid=488453454>.
Lucas S., et al.,"In Vivo Active Aldosterone Synthase Inhibitors with Improved Selectivity: Lead Optimization Providing a Series of Pyridine Substituted 3,4-Dihydro-1H-Quinolin-2-one Derivatives," Journal of Medicinal Chemistry, 2008, vol. 51(24), pp. 8077-8087.
Masters K., "Spray Drying Handbook" 4th Edition, John Wiley & Sons, 1985, Table of Contents.
Masui M., et al., "A Practical Method for Asymmetric Borane Reduction of Prochiral Ketones Using Chiral Amino Alcohols and Trimethyl Borate," Synlett, 1997, pp. 273-274.
Matzeit A, et al., "Radical Tandem Cyclizations by Anodic Decarboxylation of Carboxylic Acids," Synthesis, 1995, pp. 1432-1444.
Misra et al., "Organocatalyzed highly atom economic one pot synthesis of tetrahydropyridines as antimalarials," Bioorg Med Chem., 17(2), 625-33, 2008.
Moinet C., et al., "Novel Non-Peptide Ligands for the Somatostatin sst3 Receptor," Bioorganic & Medicinal Chemistry Letters, 2001, vol. 11(8), pp. 991-995.
Muci A., et al., "Practical Palladium Catalysts for C-N and C-O Bond Formation," Topics in Current Chemistry, 2002, vol. 219, pp. 131-209.
Muri E.M.F., et al., "Pseudo-Peptides Derived From Isomannide As Potential Inhibitors of Serine Proteases," Amino Acids, 2005, vol. 28(4), pp. 413-419.
Naylor E.M., et al. , "3-Pyridylethanolamines: Potent and Selective Human 63 Adrenergic Receptor Agonists," Bioorganic & Medicinal Chemistry Letters, 1998, vol. 8(21), pp. 3087-3092.
Nevar N.M., et al., "One Step Preparation of 1,4-Diketones from Methyl Ketones and a-Bromomethyl Ketones in the Presence of ZnC12•t-BuOH•Et2NR as a Condensation Agent," Synthesis, 2000, vol. 9, pp. 1259-1262.
Pak V.D., et al., "Catalytic Condensation of Schiffs Base With P-Methoxybenzal Acetone," Catalytic Synthesis of Organic Nitrate Compounds, 1970, vol. 68 (Part 4), pp. 66-71.
Peng T., et al., "Construction of a Library of Rhodol Fluorophores for Developing New Fluorescent Probes," Organic Letters, 2010, vol. 12(3), pp. 496-499.
Penning T.D., et al, "Discovery and SAR of 2-(1-Propylpiperidin-4-yl)-1H-Benzimidazole-4-Carboxamide: A Potent Inhibitor of Poly(ADP-ribose) Polymerase (PARP) for the Treatment of Cancer ," Bioorganic & Medicinal Chemistry, 2008, vol. 16(14), pp. 6965-6975.
Polymer Handbook, Brandrup J., et al., Eds., Interscience Publishers, 1975, Table of Contents.
Rosen M.H., et al., "Contraceptive Agents from Cycloaddition Reactions of Diarylcyclopropenones and Diarylthiirene 1, 1-Dioxides," Journal of Medicinal Chemistry, 1976, vol. 19(3), pp. 414-419.

Sato M., et al., "Efficient Preparation of Optically Pure C2-Symmetrical Cyclic Amines for Chiral Auxiliary," Synthesis, 2004, vol. 9, pp. 1434-1438.
Sawyer Scott J., et., al., "Synthetic and Structure/Activity Studies on Acid-Substituted 2-Arylphenols:Discovery of 2-[2-Propyl-3-[-3-[2-ethyl-4-(4-fluorophenyl)-5-hydroxyphenoxy]propoxy]phenoxy] benzoic Acid, a High-Affinity Leukotriene Bq Receptor Antagonist", J Med Chem., Oct. 27, 1995, 38(22), 4411-32.
Shuzo Takagi, "Antimicrobial Agents From Bletilla Striata", Phyrochemisrry, 1983, 22(4), 1011-1015.
Smith AB., et al., "Indole Diterpene Synthetic Studies: Development of a Second-Generation Synthetic Strategy for (+)-Nodulisporic Acids A and B," Journal of Organic Chemistry, 2007, vol. 72(13), pp. 4611-4620.
Smith, David C. et al., "Reissert Compound Chemistry. XXVI. The Syntheses of Bisbenzylisoquinolines", J. Heterocyclic Chem., 1976, 13, 573.
Sperling L. H., "Introduction to Physical Polymer Science," 2nd Edition, John Wiley & Sons, Inc., 1992, Table of Contents.
Sugawara M., et al., "Remarkable gamma-Effect of Tin: Acid-Promoted Cyclopropanation Reactions of alpha-((alkoxycarbonyl)oxy)stannanes with Alkenes," Journal of the American Chemical Society, 1997, vol. 119(49), pp. 11986-11987.
Tatsumi et al., "Enzyme-Mediated Coupling of 3,4-Dichloroaniline and Ferulic for Pollutant Binding to Humic Materials Add: A Model", Environ. Sci. Technol., 28(2), 210-215, 1994.
Tellinghuisen T.L., et al., "Structure of the Zinc-Binding Domain of an Essential Component of the Hepatitis C Virus Replicase," Nature, 2005, vol. 435(7040), pp. 374-379.
Vallee R.J., et al., "Photoannelation Reactions of 3-(Alk-1-ynyl)cyclohept-2-en-1-ones," Helvetica Chimica Acta, 2010, vol. 93(1), pp. 17-24.
Verboom W., et al., ""tert-Amino effect" in Heterocyclic Synthesis. Formation of N-Heterocycles by Ring Closure Reactions of Substituted 2-vinyl-N,N-dialkylanilines," Journal of Organic Chemistry, 1984, vol. 49(2), pp. 269-276.
Willis M.C., et al., "Palladium-Catalyzed Tandem Alkenyl and Aryl C-N Bond Formation: A Cascade N-Annulation Route to 1-Functionalized Indoles," Angewandte Chemie International Edition, 2005, vol. 44(3), pp. 403-406.
Wolfe J.P., et al., "Palladium-Catalyzed Amination of Aryl Triflates," Journal of Organic Chemistry, 1997, vol. 62(5), pp. 1264-1267.
Xiao et al., "A Practical Synthetic Pathway to Polysubstituted Tetrahydropyridines via Multicomponent Reactions Catalyzed by BF3•OEt2", 2005(10), 1531-1534, 2005.
Zhang J., et al., "Stereoselective Bromination-Suzuki Cross-Coupling of Dehydroamino Acids to Form Novel Reverse-Turn Peptidomimetics: Substituted Unsaturated and Saturated Indolizidinone Amino Acids," Journal of the American Chemical Society, 2002, vol. 4(23), pp. 4029-4032.
International Search Report for PCT/US2009/069188, dated Jun. 8, 2010, 4 pages.
International Preliminary Report on Patentability and Written Opinion for PCT/US2009/069188, dated Jun. 29, 2011, 10 pages.
International Search Report of PCT/US2009/069177, dated Aug. 10, 2010, 5 pages.
International Preliminary Report on Patentability and Written Opinion for PCT/US2009/069177, dated Aug. 10, 2010, 11 pages.
International Search Report for PCT/US2010/031102, dated Sep. 1, 2010, 4 pages.
International Preliminary Report on Patentability and Written Opinion for PCT/US2010/031102, dated Oct. 18, 2011, 7 pages.
International Search Report of PCT/US2011/065486, dated Mar. 26, 2012, 2 pages.
International Search Report for PCT/US2009/038077, dated Jan. 21, 2011, 4 pages.
International Preliminary Report on Patentability and Written Opinion for PCT/US2009/038077, dated Dec. 12, 2011, 11 pages.
International Search Report for PCT/US2011/39769, dated Oct. 6, 2011, 3 pages.
International Preliminary Report on Patentability and Written Opinion for PCT/US2011/39769, dated Dec. 10, 2012, 7 pages.

(56) References Cited

OTHER PUBLICATIONS

International Search Report for PCT/US2011/056045, dated Apr. 2, 2012, 4 pages.
International Search Report for PCT/US2012/026456, dated Jun. 22, 2012, 3 pages.
International Search Report for PCT/US2011/065501, dated Apr. 3, 2012, 5 pages.
Aug. 1, 2012, Office Action in U.S. Appl. No. 12/644,432.
Oct. 2, 2012, Office Action in U.S. Appl. No. 12/759,986.
Jun. 20, 2013, Office Action in U.S. Appl. No. 13/328,767.
Jul. 18, 2013, Office Action in U.S. Appl. No. 12/759,986.
Office Action for JP application 2012-506183 dated Jun. 24, 2014.
M. Alajarin et al.: "Dimerization of Tris(o-ureidobenzyl)amines: A Novel Class of Aggregates," Chem. Commun., pp. 169-170, 2001.
Office Action in U.S. Appl. No. 14/017,901 dated Nov. 28, 2014.
Office Action in CN Application No. 201180067764.7 dated Aug. 20, 2014.

\* cited by examiner

ANTI-VIRAL COMPOUNDS

This application is a Continuation of U.S. patent application Ser. No. 12/644,427, filed Dec. 22, 2009; which claims the benefit from and incorporates herein by references the entire content of U.S. Provisional Application No. 61/140,262, filed Dec. 23, 2008.

FIELD

The present invention relates to compounds effective in inhibiting replication of Hepatitis C virus ("HCV"). The present invention also relates to compositions comprising these compounds and methods of using these compounds to treat HCV infection.

BACKGROUND

HCV is an RNA virus belonging to the *Hepacivirus* genus in the Flaviviridae family. HCV has enveloped virions that contain a positive stranded RNA genome encoding all known virus-specific proteins in one single, uninterrupted, open reading frame. The open reading frame comprises approximately 9500 nucleotides encoding a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B.

HCV infection is associated with progressive liver pathology, including cirrhosis and hepatocellular carcinoma. Chronic hepatitis C may be treated with peginterferon-alpha in combination with ribavirin. Substantial limitations to efficacy and tolerability remain as many users suffer from side effects and viral elimination from the body is often inadequate. Therefore, there is a need for new drugs to treat HCV infection.

SUMMARY

The present invention features compounds of Formulae I, II and III, and pharmaceutically acceptable salts thereof. These compounds and salts are capable of inhibiting the replication of HCV.

The present invention also features compositions comprising the compounds or salts of the present invention. The compositions can also include other therapeutic agents, such as HCV helicase inhibitors, HCV polymerase inhibitors, HCV protease inhibitors, NS5A inhibitors, CD81 inhibitors, cyclophilin inhibitors, or internal ribosome entry site (IRES) inhibitors.

The present invention further features methods of using the compounds or salts of the present invention to inhibit HCV replication. The methods comprise contacting cells infected with HCV virus with a compound or salt of the present invention, thereby inhibiting the replication of HCV virus in the cells.

In addition, the present invention features methods of using the compounds or salts of the present invention, or compositions comprising the same, to treat HCV infection. The methods comprise administering a compound or salt of the present invention, or a pharmaceutical composition comprising the same, to a patient in need thereof, thereby reducing the blood or tissue level of HCV virus in the patient.

The present invention also features use of the compounds or salts of the present invention for the manufacture of medicaments for the treatment of HCV infection.

Furthermore, the present invention features processes of making the compounds or salts of the invention.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description.

DETAILED DESCRIPTION

The present invention features compounds having Formula I, and pharmaceutically acceptable salts thereof,

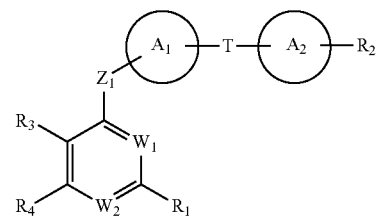

I wherein:
- $A_1$ is $C_3$-$C_{14}$carbocyclyl or 3- to 14-membered heterocyclyl, and is substituted with —$X_1$—$R_7$, wherein said $C_3$-$C_{14}$carbocyclyl and 3- to 14-membered heterocyclyl are optionally substituted with one or more $R_A$;
- $X_1$ is selected from a bond, -$L_S$-, —O—, —S—, or —N($R_B$)—;
- $R_7$ is selected from hydrogen, -$L_A$, $C_5$-$C_{10}$carbocyclyl, or 5- to 10-membered heterocyclyl, wherein at each occurrence said $C_5$-$C_{10}$carbocyclyl and 5- to 10-membered heterocyclyl are each independently optionally substituted with one or more $R_A$;
- $Z_1$ is selected from a bond, —C($R_C R_{C'}$)—, —O—, —S—, or —N($R_B$)—;
- $W_1$ and $W_2$ are each independently selected from N or C($R_D$);
- $R_1$ is selected from hydrogen or $R_A$;
- $R_3$ and $R_4$ are each independently selected from hydrogen or $R_A$; or $R_3$ and $R_4$, taken together with the carbon atoms to winch they are attached, form a $C_5$-$C_{10}$carbocyclic or 5- to 10-membered heterocyclic ring, wherein said $C_5$-$C_{10}$carbocyclic and 5- to 10-membered heterocyclic ring are optionally substituted with one or more $R_A$;
- $A_2$ is $C_3$-$C_{14}$carbocyclyl or 3- to 14-membered heterocyclyl, and is optionally substituted with one or more $R_A$;
- $R_2$ is —N($R_B$)C(O)C($R_5 R_6$)N($R_8$)-T-$R_D$,

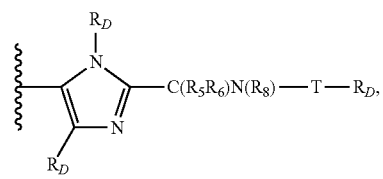

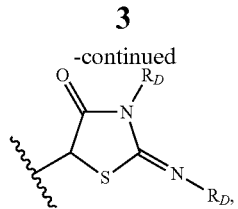

or -L$_K$-B;

R$_5$ is R$_C$;

R$_6$ is R$_{C'}$, and R$_8$ is R$_B$; or R$_6$ and R$_8$, taken together with the atoms to which they are attached, form a 3- to 10-membered heterocyclic ring which is optionally substituted with one or more R$_A$;

L$_K$ is a bond; C$_1$-C$_6$alkylene, C$_2$-C$_6$alkenylene, or C$_2$-C$_6$alkynylene, each of which is independently optionally substituted at each occurrence with one or more substituents selected from halogen, R$_S$ (except hydrogen), —O—R$_S$, —S—R$_S$, —N(R$_S$R$_{S'}$), —OC(O)R$_S$, —C(O)OR$_S$, nitro phosphate, oxo, thioxo, formyl or cyano; or —N(R$_B$)C(O)— or —C(O)N(R$_B$)—;

B is C$_3$-C$_{10}$carbocycle or 3- to 10-membered heterocycle, and is optionally substituted with one or more R$_A$;

T is independently selected at each occurrence from a bond, -L$_S$-, -L$_S$-M-L$_{S'}$-, L$_S$-M-L$_{S'}$-M'-L$_{S''}$-, wherein M and M' are independently selected from a bond, —O—, —S—, —N(R$_B$)—, —C(O)—, —S(O)$_2$—, —S(O)—, —OS(O)—, —OS(O)$_2$O—, —S(O)$_2$O—, —S(O)O—, —C(O)O—, —OC(O)—, —OC(O)O—, —C(O)N(R$_B$)—, —N(R$_B$)C(O)—, —N(R$_B$)C(O)O—, —OC(O)N(R$_B$)—, —N(R$_B$)S(O)—, —N(R$_B$)S(O)$_2$—, —S(O)N(R$_B$)—, —S(O)$_2$N(R$_B$)—, —C(O)N(R$_B$)C(O)—, —N(R$_B$)C(O)N(R$_{B'}$)—, —N(R$_B$)SO$_2$N(R$_{B'}$)—, —N(R$_B$)S(O)N(R$_{B'}$)—, C$_5$-C$_{10}$carbocycle, or 5- to 10-membered heterocycle, and wherein at each occurrence T is independently optionally substituted with one or more R$_A$;

R$_A$ is independently selected at each occurrence from halogen, hydroxy, mercapto, amino, carboxy, nitro, phosphate, oxo, thioxo, formyl, cyano, -L$_A$, or -L$_S$-R$_B$;

R$_B$ and R$_{B'}$ are each independently selected at each occurrence from hydrogen; or C$_1$-C$_6$alkyl, C$_2$-C$_6$alkenyl, C$_2$-C$_6$alkynyl, C$_3$-C$_6$carbocyclyl, C$_3$-C$_6$carbocyclylC$_1$-C$_6$alkyl, 3- to 6-membered heterocyclyl, or (3- or 6-membered heterocyclyl)C$_1$-C$_6$alkyl, each of which is independently optionally substituted at each occurrence with one or more substituents selected from halogen, hydroxy, mercapto, amino, carboxy, nitro, phosphate, oxo, thioxo, formyl or cyano;

R$_C$ and R$_{C'}$ are each independently selected at each occurrence from hydrogen; halogen; hydroxy; mercapto; amino; carboxy; nitro; phosphate; oxo; thioxo; formyl; cyano; or C$_1$-C$_6$alkyl, C$_2$-C$_6$alkenyl, C$_2$-C$_6$alkynyl, or C$_3$-C$_6$carbocyclyl, each of which is independently optionally substituted at each occurrence with one or more substituents selected from halogen, hydroxy, mercapto, amino, carboxy, nitro, phosphate, oxo, thioxo, formyl or cyano;

R$_D$, R$_{D'}$ and R$_{D''}$ are each independently selected at each occurrence from hydrogen or R$_A$ L$_A$ is independently selected at each occurrence from C$_1$-C$_6$alkyl, C$_2$-C$_6$alkenyl, or C$_2$-C$_6$alkynyl, each of which is independently optionally substituted at each occurrence with one or more substituents selected from halogen, —O—R$_S$, —S—R$_S$, —N(R$_S$R$_{S'}$), —OC(O)R$_S$, —C(O)OR$_S$, nitro, phosphate, oxo, thioxo, formyl or cyano;

L$_S$, L$_{S'}$, and L$_{S''}$ are each independently selected at each occurrence from a bond; or C$_1$-C$_6$alkylene, C$_2$-C$_6$alkenylene, or C$_2$-C$_6$alkynylene, each of which is independently optionally substituted at each occurrence with one or more substituents selected from halogen, —O—R$_S$, —S—R$_S$, —N(R$_S$R$_{S'}$), —OC(O)R$_S$, C(O)OR$_S$, nitro, phosphate, oxo, thioxo, formyl or cyano;

R$_E$ is independently selected at each occurrence from —O—R$_S$, —S—R$_S$, —C(O)R$_S$, —OC(O)R$_S$, —C(O)OR$_S$, —N(R$_S$R$_{S'}$), —S(O)R$_S$, —SO$_2$R$_S$, —C(O)N(R$_S$R$_{S'}$), —N(R$_S$)C(O)R$_{S'}$, —N(R$_S$)C(O)N(R$_S$R$_{S'}$), —N(R$_S$)SO$_2$R$_{S'}$, —SO$_2$N(R$_S$R$_{S'}$), —N(R$_S$)SO$_2$N(R$_S$R$_{S''}$), —N(R$_S$)S(O)N(R$_S$R$_{S''}$), —OS(O)—R$_S$, —OS(O)$_2$—R$_S$, —S(O)$_2$OR$_S$, —S(O)OR$_S$, —OC(O)OR$_S$, —N(R$_S$)C(O)OR$_{S'}$, —OC(O)N(R$_S$R$_{S'}$), —N(R$_S$)S(O)—R$_{S'}$, —S(O)N(R$_S$R$_{S'}$), —C(O)N(R$_S$)C(O)—R$_{S'}$, C$_3$-C$_{10}$carbocyclyl, or 3- to 10-membered heterocyclyl, wherein said C$_3$-C$_{10}$carbocyclyl and 3- to 10-membered heterocyclyl are each independently optionally substituted at each occurrence with one or more substituents selected from C$_1$-C$_6$alkyl, C$_2$-C$_6$alkenyl, C$_2$-C$_6$alkynyl, R$_S$ (except hydrogen), halogen, —O—R$_B$, —S—R$_B$, —N(R$_B$R$_{B'}$), —OC(O)R$_B$, —C(O)OR$_B$, nitro, phosphate, oxo, thioxo, formyl or cyano; and R$_S$, R$_{S'}$ and R$_{S''}$ are each independently selected at each occurrence from hydrogen; or C$_1$-C$_6$alkyl, C$_2$-C$_6$alkenyl, C$_2$-C$_6$alkynyl, C$_3$-C$_6$carbocyclyl, C$_3$-C$_6$carbocyclylC$_1$-C$_6$alkyl, 3- to 6-membered heterocyclyl, or (3- or 6-membered heterocyclyl)C$_1$-C$_6$alkyl, each of which is independently optionally substituted at each occurrence with one or more substituents selected from halogen, —O—R$_B$, —S—R$_B$, —N(R$_B$R$_{B'}$), —OC(O)R$_B$, —C(O)OR$_B$, nitro, phosphate, oxo, thioxo, formyl or cyano.

A$_1$ preferably is selected from C$_5$-C$_6$carbocycles or 5- to 6-membered heterocycles (e.g., phenyl, thiazolyl, thienyl, pyrrolidinyl or piperidinyl), and is optionally substituted with one or more R$_4$, A$_1$ is substituted with —X$_1$—R$_7$. The ring system in A$_1$ can be identical to, or different from, that in A$_2$. For instance, A$_1$ and A$_2$ can both be phenyl, or A$_1$ is phenyl and A$_2$ is thiazolyl, thienyl, furanyl, imidazolyl, pyridinyl, pyrimidinyl, pyridazinyl, benzoxazolyl, benzothienyl, benzimidazolyl, indolyl, or

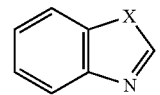

(where X is O, S or N(R$_B$)). Z$_1$ and T can be attached to A$_1$ via any two substitutable ring atoms on A$_1$. Two adjacent R$_4$ on A$_1$, taken together with the ring atoms to which they are attached, may form a C$_5$-C$_6$carbocycle or a 5- to 6-membered heterocycle.

Z$_1$ preferably is —N(R$_B$)—, such as —NH— or —N(C$_1$-C$_6$alkyl)-.

R$_3$ and R$_4$, taken together with the carbon atoms to which they are attached, preferably form a C$_5$-C$_6$carbocycle or a 5- to 6-membered heterocycle, which is optionally substituted with one or more R$_4$. Non-limiting examples of suitable 5- to 6-membered carbocycles or heterocycles for this purpose include

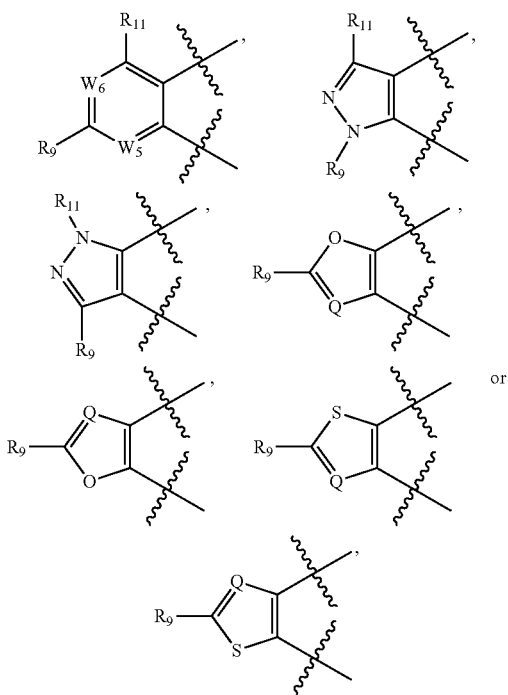

where $W_5$ and $W_6$ are independently N or $C(R_D)$, Q is N or $C(R_D)$, and $R_D$, $R_9$ and $R_{11}$ are each independently selected at each occurrence from hydrogen or $R_A$. Preferred examples of suitable 5- to 6-membered heterocycles include

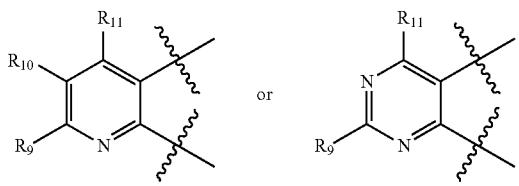

where $R_9$, $R_{10}$, and $R_{11}$ are each independently selected from hydrogen or $R_A$. More preferably, $R_3$ and $R_4$ taken together with the carbon atoms to which they are attached, form

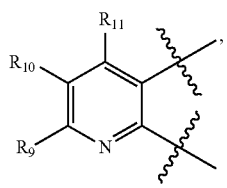

where $R_9$, $R_{10}$ and $R_{11}$ are each independently selected from hydrogen; halogen; or $C_1$-$C_6$alkyl, $C_2$-$C_6$alkenyl, $C_2$-$C_6$alkynyl, $C_3$-$C_6$carbocyclyl, or $C_3$-$C_6$carbocyclyC$_1$-$C_6$alkyl, each of which is independently optionally substituted at each occurrence with one or more substituents selected from halogen, hydroxy, mercapto, amino, carboxy, nitro, phosphate, oxo, thioxo, formyl or cyano. Highly preferably, $R_9$ is selected from $C_1$-$C_6$alkyl, $C_2$-$C_6$alkenyl; $C_2$-$C_6$alkynyl, $C_3$-$C_6$carbocyclyl (e.g., $C_1$-$C_6$cycloalkyl), or $C_3$-$C_6$carbocyclyC$_1$-$C_6$alkyl (e.g., $C_3$-$C_6$cycloalkylC$_1$-$C_6$alkyl), each of which is independently optionally substituted at each occurrence with one or more substituents selected from halogen, hydroxy, mercapto, amino, carboxy, nitro, phosphate, oxo, thioxo, formyl or cyano; and $R_{10}$ and $R_{11}$ are hydrogen.

$R_1$ can be, without limitation, hydrogen or $C_1$-$C_6$alkyl. Preferably, $R_1$ is hydrogen.

$X_1$ is preferably selected from —$CH_2$—, —O—, or —S—.

$R_7$ can be selected, without limitation, from $C_5$-$C_6$carbocycles or 5- to 6-membered heterocycles, and is optionally substituted with one or more $R_A$. Preferably, $R_7$ is phenyl, and is optionally substituted with one or more $R_A$ (e.g., —N($R_S R_S'$), such as —NH$_2$ or —NH($C_1$-$C_6$alkyl)).

$A_2$ can be selected, without limitation, from $C_5$-$C_{10}$carbocycles or 5- to 10-membered heterocycles, and is optionally substituted with one or more $R_A$. Preferably, $A_2$ is selected from $C_5$-$C_6$carbocycles or 5- to 6-membered heterocycles, and is optionally substituted with one or more $R_A$. Two adjacent $R_A$ on $A_2$, taken together with the ring atoms to which they are attached, may form a $C_5$-$C_6$carbocycle or a 5- to 6-membered heterocycle. Non-limiting examples of suitable $A_2$ include phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl, each of which is optionally substituted with one or more $R_A$. As a non-limiting example, $A_2$ is

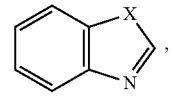

where X is O, S or N($R_B$). T and $R_2$ can be attached to $A_2$ via any two substitutable ring atoms on $A_2$. For instance, $A_2$ can be

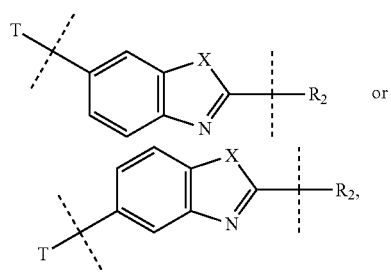

$R_2$ can be —N($R_B$)C(O)C($R_5 R_6$)N($R_8$)-T-$R_D$, where $R_5$ is $R_C$ (e.g., hydrogen) and $R_6$ and $R_8$, taken together with the atoms to which they are attached, form a 5- to 6-membered heterocyclic ring which is optionally substituted with one or more $R_A$. $R_6$ and $R_8$, taken together with the atoms to which they are attached, can form, without limitation,

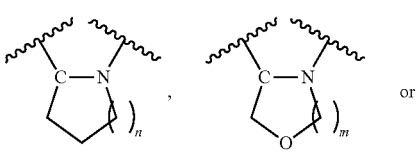

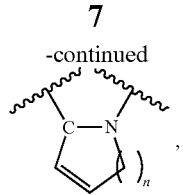

each of which is independently optionally substituted with one or more $R_A$, where n is 0, 1 or 2, and m is 1 or 2. Two adjacent $R_A$, taken together with the atoms to which they are attached, can form a $C_5$-$C_6$carbocycle or a 5- to 6-membered heterocycle.

-T-$R_D$ preferably is —C(O)-$L_S$-$R_{12}$ or —C(O)-$L_S$-M'-$L_{S''}$-$R_{12}$, where $R_{12}$ is (i) hydrogen, (ii) $C_1$-$C_6$alkyl, $C_2$-$C_6$alkenyl or $C_2$-$C_6$alkynyl, each of which is independently optionally substituted at each occurrence with one or mote substituents selected from halogen, —O—$R_S$, —S—$R_S$, —N($R_SR_{S'}$), —OC(O)$R_S$, —C(O)O$R_S$, nitro, phosphate, oxo, thioxo, formyl or cyano, or (iii) $C_3$-$C_{10}$carbocyclyl or 3- to 10-membered heterocyclyl, each of which is independently optionally substituted at each occurrence with one or more substituents selected from $C_1$-$C_6$alkyl, $C_2$-$C_6$alkenyl, $C_2$-$C_6$alkynyl, $R_S$ (except hydrogen), halogen, —O—$R_B$, —S—$R_B$; —N($R_BR_{B'}$), —OC(O)$R_B$, —C(O)O$R_B$, nitro, phosphate, oxo, thioxo, formyl or cyano. -T-$R_D$ can also be, without limitation, -$L_S$-($C_3$-$C_{10}$carbocyclyl) or -$L_S$-(3- to 10-membered heterocyclyl), where said $C_3$-$C_{10}$carbocyclyl and 3- to 10-membered heterocyclyl are each independently optionally substituted with one or more substituents selected from $C_1$-$C_6$alkyl, $C_2$-$C_6$alkenyl, $C_2$-$C_6$alkynyls $R_S$ (except hydrogen), halogen, —O—$R_B$, —S—$R_B$, —N($R_BR_{B'}$), —OC(O)$R_B$, —C(O)$R_B$, nitro, phosphate, oxo, thioxo, formyl or cyano. In addition, -T-$R_D$ can be, without limitation, -$L_S$-$R_E$, —C(O)-$L_S$-$R_E$, —C(O)O-$L_S$-$R_E$.

Preferably, $R_2$ is

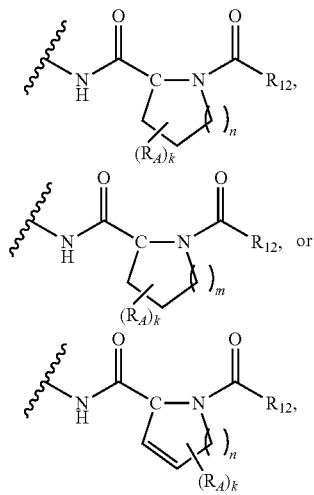

where n is 0, 1 or 2, m is 1 or 2, and k is 0, 1, 2, 3, or 4. Two adjacent $R_A$, taken together with the atoms to which they are attached, can form a $C_5$-$C_6$carbocycle or a 5- to 6-membered heterocycle. $R_{12}$ can be, without limitation, -$L_T$-N($R_B$)-$L_{TT}$-$R_E$, -$L_T$-N($R_B$)C(O)-$L_{TT}$-$R_E$, or -$L_T$-N($R_B$)C(O)-$L_{TT}$-$R_E$, wherein $L_T$ and $L_{TT}$ are each independently selected from (i) a bond, or (ii) $C_1$-$C_6$alkylene, $C_2$-$C_6$alkenylene, or $C_2$-$C_6$alkynylene, each of which is independently optionally substituted at each occurrence with one or more substituents selected from halogen, $C_3$-$C_{10}$carbocyclyl, 3- to 10-membered heterocyclyl, —O—$R_S$, —S—$R_S$, —N($R_SR_{S'}$), —OC(O)$R_S$, —C(O)O$R_S$; nitro, phosphate, oxo, thioxo, formyl or cyano. Preferably, $R_{12}$ is -$L_T$-N($R_B$)-$L_{TT}$-$R_S$, -$L_T$-N($R_S$)C(O)-$L_{TT}$-$R_S$, or -$L_T$-N($R_S$)C(O)-$L_{TT}$-$R_S$, where $L_T$ and $L_{TT}$ are as defined immediately above. $R_{12}$ can also be, without limitation, -$L_S$-$R_E$, such as -$L_S$-O—$R_S$, -$L_S$-S—$R_S$, or -$L_S$-N($R_SR_{S'}$). In addition, $R_{12}$ can be, without limitation, -$L_S$-($C_3$-$C_{10}$carbocyclyl) or -$L_S$-(3- to 10-membered heterocyclyl), where said $C_3$-$C_{10}$carbocyclyl and 3- to 10-membered heterocyclyl are each independently optionally substituted with one or more substituents selected from $C_1$-$C_6$alkyl, $C_2$-$C_6$alkenyl, $C_2$-$C_6$alkynyl, $R_S$ (except hydrogen), halogen, —O—$R_S$—S—$R_B$, —N($R_BR_{B'}$), —OC(O)$R_B$, —C(O)O$R_B$, nitro, phosphate, oxo, thioxo, formyl or cyano.

$R_2$ can also be

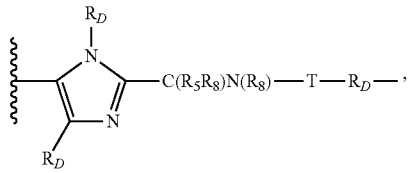

where $R_5$ is $R_C$ (e.g., hydrogen), and $R_6$ and $R_8$ taken together with the atoms to which they are attached, form a 5- to 6-membered heterocyclic ring which is optionally substituted with one or more $R_A$. For instance, $R_6$ and $R_8$, taken together with the atoms to which they are attached, can form, without limitation,

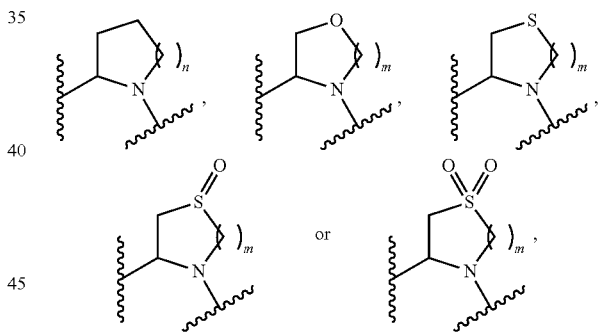

each of which is optionally substituted with one or more $R_A$, where n is 0, 1 or 2, and m is 1 or 2. Two adjacent $R_A$, taken together with the atoms to which they are attached, can form a $C_5$-$C_6$carbocycle or a 5- to 6-membered heterocycle.

-T-$R_{D''}$ can be, without limitation, —C(O)-$L_S$-$R_{12}$ or —C(O)-$L_S$-M'-$L_{S''}$-$R_{12}$, where $R_{12}$ is (i) hydrogen, (ii) $C_1$-$C_6$alkyl, $C_2$-$C_6$alkenyl or $C_2$-$C_6$alkynyl, each of which is independently optionally substituted at each occurrence with one or more substituents selected from halogen, —O—$R_S$, —S—$R_S$, —N($R_SR_{S'}$), —OC(O)$R_S$, —C(O)O$R_S$, nitro, phosphate, oxo, thioxo, formyl or cyano, or (iii) $C_3$-$C_{10}$carbocyclyl or 3- to 10-membered heterocyclyl, each of which is independently optionally substituted at each occurrence with one or more substituents selected from $C_1$-$C_6$alkyl, $C_2$-$C_6$alkenyl, $C_2$-$C_6$alkynyl, $R_S$ (except hydrogen), halogen, —O—$R_B$, —S—$R_B$, —N($R_BR_{B'}$), —OC(O)$R_B$, —C(O)$R_B$, nitro, phosphate, oxo, thioxo, formyl or cyano. -T-$R_{D''}$ can also be, without limitation, -$L_S$-($C_3$-$C_{10}$carbocyclyl) or -$L_S$-(3- to 10-membered heterocyclyl), where said $C_3$-$C_{10}$carbocyclyl and 3- to 10-membered heterocyclyl are each independently optionally substituted with one or more substituents selected from $C_1$-$C_6$alkyl, $C_2$-$C_6$alkenyl, $C_2$-$C_6$alkynyl, $R_S$ (except hydrogen), halogen, —O—$R_S$, —S—$R_B$, —N($R_B R_{B'}$), —OC(O)$R_B$, —C(O)O$R_B$, nitro, phosphate, oxo, thioxo, formyl or cyano. In addition, -T-$R_{D''}$ can be, without limitation, -$L_S$-$R_E$, —C(O)-$L_S$-$R_E$, —C(O)O-$L_S$-$R_E$.

Preferably, $R_2$ is

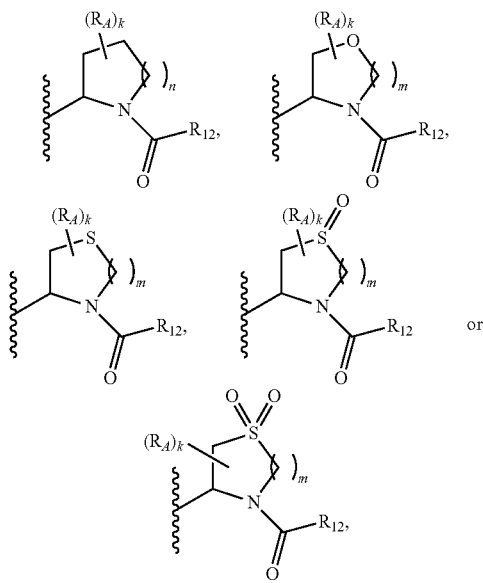

where n is 0, 1 or 2, m is 1 or 2, and k is 0, 1, 2, 3 or 4. Two adjacent $R_A$, taken together with the atoms to which they are attached, can form a $C_5$-$C_6$carbocycle or a 5- to 6-membered heterocycle. $R_{12}$ can be, without limitation, -$L_T$-N($R_B$)-$L_{TT}$-$R_E$, -$L_T$-N($R_B$)C(O)-$L_{TT}$-$R_E$, or -$L_T$-N($R_B$)C(O)-$L_{TT}$-$R_E$, wherein $L_T$ and $L_{TT}$ are each independently selected from (i) a bond, or (ii) $C_1$-$C_6$alkylene, $C_2$-$C_6$alkenylene, or $C_2$-$C_6$alkynylene, each of which is independently optionally substituted at each occurrence with one or more substituents selected from halogen, $C_3$-$C_{10}$carbocyclyl, 3- to 10-membered heterocyclyl, —O—$R_S$, —S—$R_S$, —N($R_S R_{S'}$), —OC(O)$R_S$, —C(O)O$R_S$, nitro, phosphate, oxo, thioxo, formyl or cyano. Preferably, $R_{12}$ is -$L_T$-N($R_B$)-$L_{TT}$-$R_S$, -$L_T$-N($R_B$)C(O)-$L_{TT}$-$R_S$, or -$L_T$-N($R_B$)C(O)-$L_{TT}$-$R_S$, where $L_T$ and $L_{TT}$ are as defined immediately above, $R_{12}$ can also be, without limitation, -$L_S$-$R_E$, such as -$L_S$-O—$R_S$, -$L_S$-S—$R_S$, or -$L_S$-N($R_S R_{S'}$). In addition, $R_{12}$ can be, without limitation, -$L_S$-($C_3$-$C_{10}$carbocyclyl) or -$L_S$-(3- to 10-membered heterocyclyl), where said $C_3$-$C_{10}$carbocyclyl and 3- to 10-membered heterocyclyl are each independently optionally substituted with one or more substituents selected from $C_1$-$C_6$alkyl, $C_2$-$C_6$alkenyl, $C_2$-$C_6$alkynyl, $R_S$ (except hydrogen), halogen, —O—$R_B$, —S—$R_B$, —N($R_B R_{B'}$), —OC(O)$R_B$, —C(O)O$R_B$, nitro, phosphate, oxo, thioxo, formyl or cyano.

Furthermore, $R_2$ can be, without limitation, -$L_K$-B, where B is $C_3$-$C_{10}$carbocycle or 3- to 10-membered heterocycle, and is optionally substituted with one or more $R_A$. Non-limiting examples of suitable B include

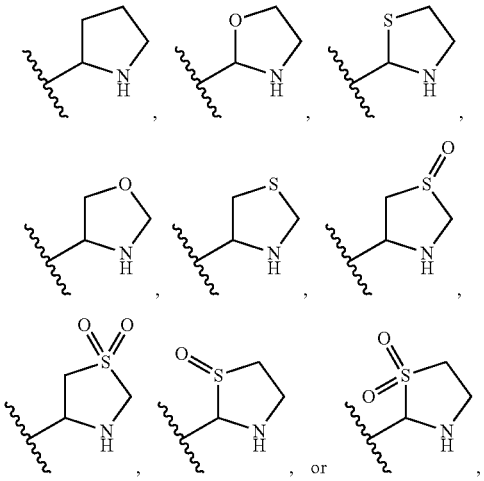

each of which is optionally substituted with one or more $R_A$. Two adjacent $R_A$, taken together wills the atoms to which they are attached, can form a $C_5$-$C_6$carbocycle or a 5- to 6-membered heterocycle. Preferred examples of suitable B include

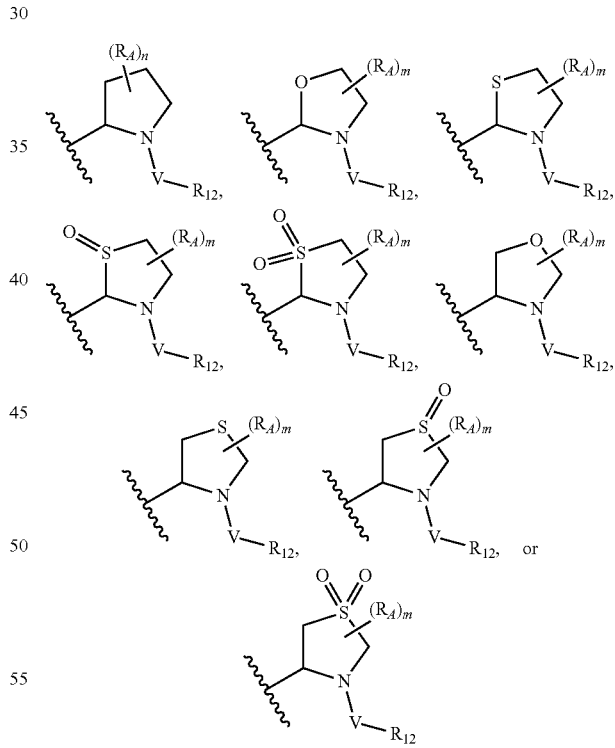

wherein n is 0, 1, 2, 3 or 4, m is 0, 1, 2 or 3, V is —C(O)— or —S(O)$_2$—, and $R_{12}$ is —$R_S$, —O$R_S$ or —N($R_S R_{S'}$), and wherein two adjacent $R_A$, taken together with the atoms to which they are attached, can form a $C_5$-$C_6$carbocycle or a 5- to 6-membered heterocycle. In one example, $R_2$ is

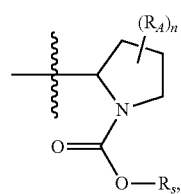

where n is 0, 1, 2, 3 or 4, and two adjacent $R_A$, taken together with the atoms to which they are attached, can form a $C_5$-$C_6$carbocycle or a 5- to 6-membered heterocycle.

$R_2$ can also be, without limitation,

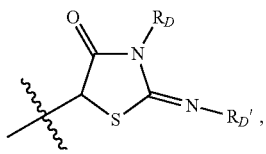

where $R_D$ an $R_{D'}$ are independently selected from (i) $C_1$-$C_6$alkyl, $C_2$-$C_6$alkenyl or $C_2$-$C_6$alkynyl, each of which is independently optionally substituted at each occurrence with one or more substituents selected from halogen, —O—$R_S$, —S—$R_S$, —N($R_S R_{S'}$), —OC(O))$R_S$, —C(O)$R_S$, nitro, phosphate, oxo, thioxo, formyl or cyano; (ii) -$L_S$-$C_3$-$C_{10}$carbocyclyl or -$L_S$-(3- to 10-membered heterocyclyl), each of which is optionally substituted with one or more substituents selected from $C_1$-$C_6$alkyl, $C_2$-$C_6$alkenyl, $C_2$-$C_6$alkynyl, $R_S$ (except hydrogen), halogen, —O—$R_B$, —S—$R_B$, —N($R_B R_{B'}$), —OC(O)$R_B$, —C(O)O$R_B$, nitro, phosphate, oxo, thioxo, formyl or cyano; or (iii) -$L_S$-O—$R_S$, -$L_S$-S—$R_S$, or -$L_S$-N($R_S R_{S'}$). Alternatively, $R_D$ and $R_{D'}$ can join to form a 5- to 6-membered heterocycle.

T can be selected, without limitation, from the following moieties:

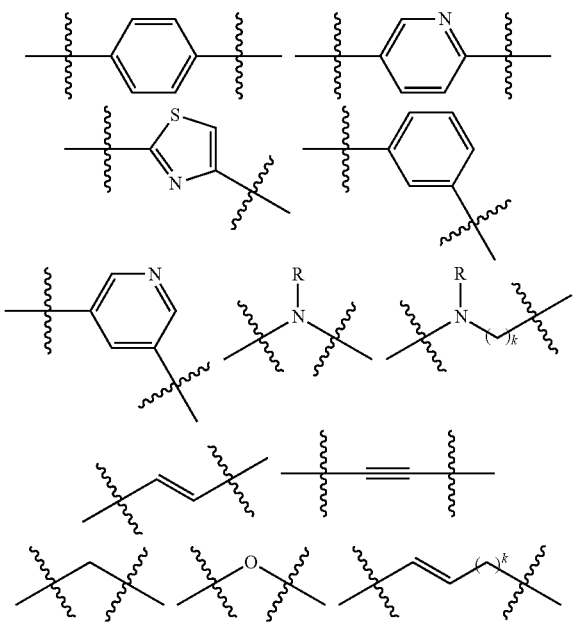

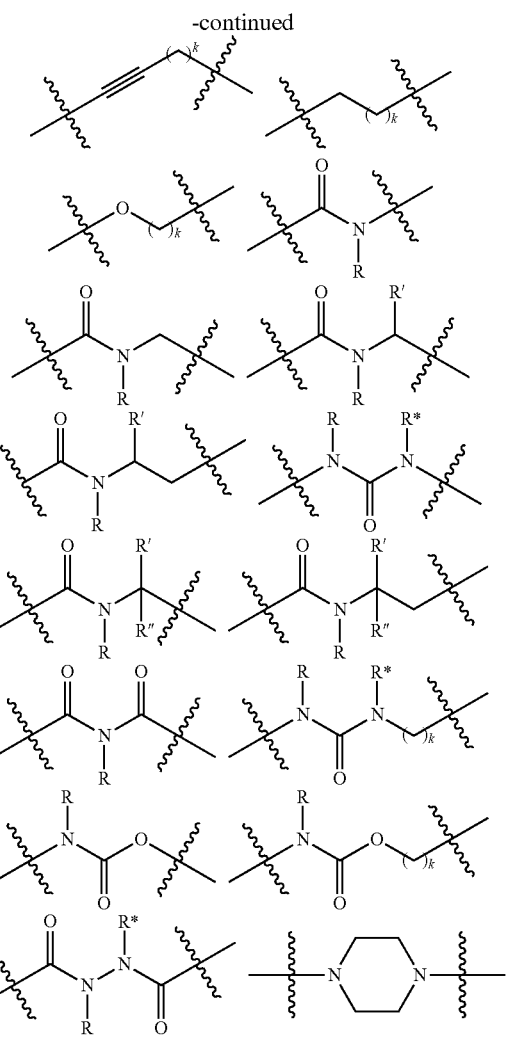

where k is 1 or 2, R and R* are independently hydrogen or $C_1$-$C_6$alkyl, and R' and R" are independently $C_1$-$C_6$alkyl or $C_6$-$C_{10}$aryl.

Preferably, T is selected from table 4 described below. More preferably, T is -$L_S$-N($R_T$)-$L_{S'}$- (e.g., CH$_2$—N($R_T$)—CH$_2$—), or -$L_S$-C($R_T R_{T'}$)-$L_{S'}$- (e.g., —CH$_2$—C($R_T R_{T'}$)—CH$_2$—) $R_T$ is $C_1$-$C_6$alkyl, $C_2$-$C_6$alkenyl, or $C_2$-$C_6$alkynyl, each of which is independently optionally substituted at each occurrence with one or more substituents selected from halogen, —O—$R_S$, —S—$R_S$, —N($R_S R_{S'}$), —OC(O)$R_S$, —C(O)O$R_S$, nitro, phosphate, oxo, thioxo, formyl or cyano; or $R_T$ is $C_3$-$C_6$carbocyclyl, $C_3$-$C_6$carbocyclyl$C_1$-$C_6$alkyl, 3- to 6-membered heterocyclyl, or (3- or 6-membered heterocyclyl)$C_1$-$C_6$alkyl, each of which is independently optionally substituted at each occurrence with one or more substituents selected from $C_1$-$C_6$alkyl, $C_2$-$C_6$alkenyl, $C_2$-$C_6$alkynyl, $R_S$ (except hydrogen), halogen, —O—$R_B$, —S—$R_B$, —N($R_B R_{B'}$), —OC(O)$R_S$, —C(O)O$R_B$, nitro, phosphate, oxo, thioxo, formyl or cyano. $R_T$ is $R_A$, and preferably $R_T$ is hydrogen, $L_S$, $L_{S'}$, $R_A$, $R_B$, $R_{B'}$, $R_S$, and $R_{S'}$ are as defined above.

In one embodiment, $A_1$ is 5- to 6-membered carbocycle or heterocycle (e.g., phenyl, thiazolyl, thienyl, pyrrolidinyl or piperidinyl), which is substituted with —$X_1$—$R_7$ and is optionally substituted with one or more $R_A$; and $A_2$ is 5- to 10-membered carbocycle or heterocycle (e.g., phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl) and is optionally substituted with one or more $R_4$. $R_3$ and $R_4$, taken together with the carbon atoms to which they are attached, form a 5- to 6-membered carbocycle or heterocycle which is optionally substituted with one or more $R_4$. Preferably, $A_2$ is 5- to 6-membered carbocycle or heterocycle (e.g., phenyl), and is optionally substituted with one or more $R_4$; $A_1$ is phenyl and is optionally substituted with one or more $R_4$; $X_1$ is —CH$_2$—, —O—, or —S—; and $R_7$ is 5- to 6-membered carbocycle or heterocycle (e.g., phenyl) which is optionally substituted with one or more $R_4$.

In another embodiment, $W_1$ and $W_2$ are N, and $Z_1$ is —N($R_B$)—. Preferably, $Z_1$ is selected from —NH—, —N($C_1$-$C_6$alkyl)-, —N($C_2$-$C_6$alkenyl)-, —N($C_1$-$C_6$alkynyl)-, —N($C_1$-$C_6$haloalkyl)-, —N($C_2$-$C_6$haloalkenyl)-, or —N($C_2$-$C_6$haloalkynyl)-. More preferably, $Z_1$ is selected from —NH— or —N($C_1$-$C_6$alkyl)-.

In still another embodiment, $R_3$ and $R_4$ taken together with the carbon atoms to which they are attached, form

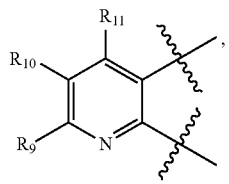

where $R_9$, $R_{10}$, and $R_{11}$ are each independently selected from hydrogen or $R_4$. Preferably, $W_1$ and $W_2$ are N, $Z_1$ is —N($R_B$)— (e.g., —NH— or —N($C_1$-$C_6$alkyl)-), and $X_1$ is —CH$_2$—, —O— or —S—. $R_7$ preferably is phenyl, and is optionally substituted with one or more $R_4$. Also preferably, $R_1$ is hydrogen; and $R_9$, $R_{10}$, and $R_{11}$ are each independently selected from hydrogen; halogen; or $C_1$-$C_6$alkyl, $C_2$-$C_6$alkenyl, $C_2$-$C_6$alkynyl, $C_3$-$C_6$carbocyclyl, or $C_3$-$C_6$carbocyclyl$C_1$-$C_6$alkyl, each of which is independently optionally substituted at each occurrence with one or more substituents selected from halogen, hydroxy, mercapto, amino, carboxy, nitro, phosphate, oxo, thioxo, formyl or cyano. Highly preferably, $R_{10}$ and $R_{11}$ are hydrogen; and $R_9$ is selected from $C_1$-$C_6$alkyl, $C_2$-$C_6$alkenyl, $C_2$-$C_6$alkynyl, $C_3$-$C_6$carbocyclyl (e.g., $C_3$-$C_6$cycloalkyl), or $C_3$-$C_6$carbocyclyC$_1$-$C_6$alkyl (e.g., $C_3$-$C_6$cycloalkylC$_1$-$C_6$alkyl), and is optionally substituted with one or more substituents selected from halogen, hydroxy, mercapto, amino, carboxy, nitro, phosphate, oxo, thioxo, formyl or cyano.

In yet another embodiment, $R_3$ and $R_4$ are each independently selected from hydrogen or $R_4$; and $R_7$ is a 5- to 6-membered carbocycle or heterocycle (e.g., phenyl), which is optionally substituted with one or more $R_4$.

In a further embodiment, $R_3$ and $R_4$ are each independently selected from hydrogen or $R_4$; $A_1$ is 5- to 6-membered carbocycle or heterocycle (e.g., phenyl, thiazolyl, thienyl, pyrrolidinyl or piperidinyl), which is substituted with —$X_1$—$R_7$ and is optionally substituted with one or more $R_4$; and $A_2$ is a 5- to 10-membered carbocycle or heterocycle (e.g., phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl), and is optionally substituted with one or more $R_4$. Preferably, $A_2$ is 5- to 6-membered carbocycle or heterocycle (e.g., phenyl), and is optionally substituted with one or more $R_4$; $A_1$ is phenyl and is optionally substituted with one or more $R_4$; $X_1$ is —CH$_2$—, —O—, or —S—; and $R_7$ is 5- to 6-membered carbocycle or heterocycle (e.g., phenyl) which is optionally substituted with one or more $R_4$. $W_1$ and $W_2$ can be N, and $Z_1$ can be —N($R_B$)—, such as —NH—, —N($C_1$-$C_6$alkyl)-, —N($C_2$-$C_6$alkenyl)-, —N($C_2$-$C_6$alkynyl)-, —N($C_1$-$C_4$haloalkyl)-, —N($C_2$-$C_6$haloalkenyl)-, or —N($C_2$-$C_6$haloalkynyl)-.

In still yet another embodiment,

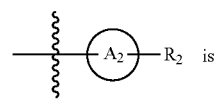

is

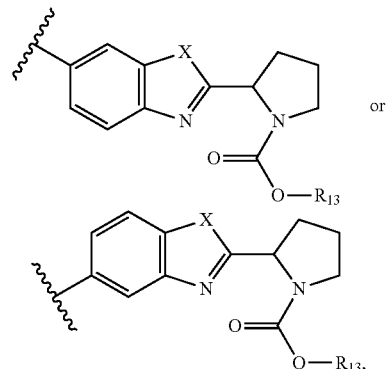

where X is O, S or N($R_B$), and $R_{13}$ is $R_S$. Preferably, $R\_is$ $C_1$-$C_6$alkyl, $C_2$-$C_6$alkenyl, $C_2$-$C_6$alkynyl, $C_3$-$C_6$carbocyclyl, $C_3$-$C_6$carbocyclylC$_1$-$C_6$alkyl, 3- to 6-membered heterocyclyl, or (3- or 6-membered heterocyclyl)C$_1$-$C_6$alkyl, each of which is independently optionally substituted at each occurrence with one or more substituents selected from halogen, —O— $R_B$, —S—$R_B$, —N($R_B R_{B'}$), —OC(O)$R_B$, —C(O)OR$_S$, nitro, phosphate, oxo, thioxo, formyl or cyano. X preferably is O, S, NH or N($C_1$-$C_6$alkyl).

The present invention also features compounds having Formula II or III, and pharmaceutically acceptable salts thereof,

II

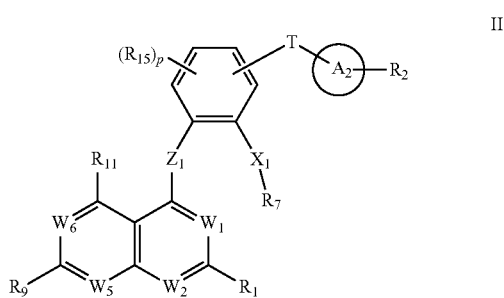

-continued

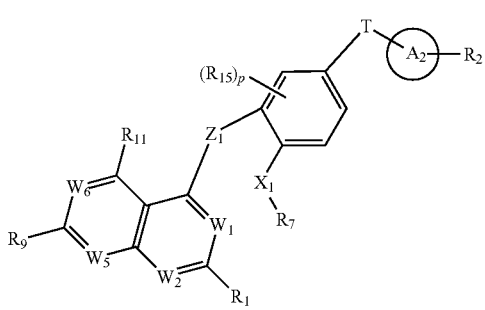

III wherein:
- $X_1$ is independently selected from a bond, $-L_S-$, $-O-$, $-S-$, or $-N(R_B)-$;
- $R_7$ is selected from hydrogen, $-L_A$, $C_5-C_{10}$carbocyclyl, or 5- to 10-membered heterocyclyl, wherein said $C_5-C_{10}$carbocyclyl and 5- to 10-membered heterocyclyl are each independently optionally substituted with one or more $R_A$;
- $Z_1$ is selected from a bond, $-C(R_CR_{C'})-$, $-O-$, $-S-$, or $-N(R_B)-$;
- $W_1$, $W_2$, $W_5$, and $W_6$ are each independently selected from N or $C(R_D)$, wherein $R_D$ is independently selected at each occurrence from hydrogen or $R_A$;
- $R_1$, $R_9$, $R_{11}$, $R_{15}$ are each independently selected at each occurrence from hydrogen or $R_A$;
- p is selected from 0, 1, 2, or 3;
- $A_2$ is $C_3-C_{14}$carbocyclyl or 3- to 14-membered heterocyclyl, and is optionally substituted with one or more $R_A$;
- $R_2$—$N(R_B)C(O)C(R_5R_6)N(R_8)$-T-$R_D$,

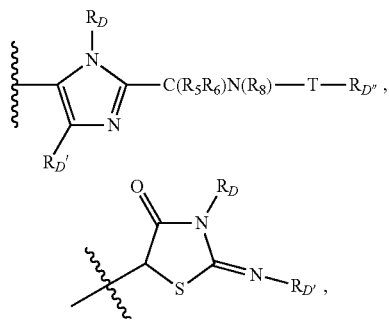

or $-L_K$-B;
- $R_5$ is $R_C$;
- $R_6$ is $R_{C'}$, and $R_S$ is $R_B$; or $R_6$ and $R_8$, taken together with the atoms to which they are attached, form a 3- to 10-membered heterocyclic ring which is optionally substituted with one or more $R_A$;
- $L_K$ is a bond; $C_1-C_6$alkylene, $C_2-C_6$alkenylene, or $C_2-C_6$alkynylene, each of which is independently optionally substituted at each occurrence with one or more substituents selected from halogen, $R_S$ (except hydrogen), $-O-R_S$, $-S-R_S$, $-N(R_SR_{S'})$, $-OC(O)R_S$, $-C(O)OR_S$, nitro, phosphate, oxo, thioxo, formyl or cyano; or $-N(R_B)C(O)-$ or $-C(O)N(R_B)-$;
- B is $C_1-C_{10}$carbocycle or 3- to 10-membered heterocycle, and is optionally substituted with one or more $R_A$;
- T is independently selected at each occurrence from a bond, $-L_S-$, $-L_S-M-L_{S'}-$, $-L_S-M-L_{S'}-M'-L_{S''}-$, wherein M and M' are each independently selected from a bond, $-O-$, $-S-$, $-N(R_B)-$, $-C(O)-$, $-S(O)_2-$, $-S(O)-$, $-OS(O)-$, $-OS(O)_2-$, $-S(O)_2O-$, $-S(O)O-$, $-C(O)O-$, $-OC(O)-$, $-OC(O)O-$, $-C(O)N(R_B)-$, $-N(R_B)C(O)-$, $-N(R_B)C(O)O-$, $-OC(O)N(R_B)-$, $-N(R_B)S(O)-$, $-N(R_B)S(O)_2-$, $-S(O)N(R_B)-$, $-S(O)_2N(R_B)-$, $-C(O)N(R_B)C(O)-$, $-N(R_B)C(O)N(R_{B'})-$, $-N(R_B)SO_2N(R_{B'})-$, $-N(R_B)S(O)N(R_{B'})-$, $C_5-C_{10}$carbocycle, or 5- to 10-membered heterocycle, and wherein at each occurrence T is independently optionally substituted with one or more $R_A$;
- $R_A$ is independently selected at each occurrence from halogen, hydroxy, mercapto, amino, carboxy, nitro, phosphate, oxo, thioxo, formyl, cyano, $-L_A$, or $-L_S-R_E$;
- $R_B$ and $R_{B'}$ are each independently selected at each occurrence from hydrogen; or $C_1-C_6$alkyl, $C_2-C_6$alkenyl, $C_2-C_6$alkynyl, $C_3-C_6$carbocyclyl, $C_3-C_6$carbocycylC$_1$-C$_6$alkyl, 3- to 6-membered heterocyclyl, or (3- or 6-membered heterocyclyl)C$_1$-C$_6$alkyl, each of which is independently optionally substituted at each occurrence with one or more substituents selected from halogen, hydroxy, mercapto, amino, carboxy, nitro, phosphate, oxo, thioxo, formyl or cyano;
- $R_C$ and $R_{C'}$ are each independently selected at each occurrence from hydrogen; halogen; hydroxy; mercapto; amino; carboxy; nitro; phosphate; oxo; thioxo; formyl; cyano; or $C_1-C_6$alkyl, $C_2-C_6$alkenyl, $C_2-C_6$alkynyl, or $C_3-C_6$carbocyclyl, each of which is independently optionally substituted at each occurrence with one or more substituents selected from halogen, hydroxy, mercapto, amino, carboxy, nitro, phosphate, oxo, thioxo, formyl or cyano;
- $R_D$, $R_{D'}$ and $R_{D''}$ are each independently selected at each occurrence from hydrogen or $R_A$
- $L_A$ is independently selected at each occurrence from $C_1-C_6$alkyl, $C_2-C_6$alkenyl, or $C_2-C_6$alkynyl, each of which is independently optionally substituted at each occurrence with one or more substituents selected from halogen, $-O-R_S$, $-S-R_S$, $-N(R_SR_{S'})$, $-OC(O)R_S$, $-C(O)OR_S$, nitro, phosphate, oxo, thioxo, formyl or cyano;
- $L_S$, $L_{S'}$ and $L_{S''}$ are each independently selected at each occurrence from a bond; or $C_1-C_6$alkylene, $C_2-C_6$alkenylene, or $C_2-C_6$alkynylene, each of which is independently optionally substituted at each occurrence with one or more substituents selected from halogen, $-O-R_S$, $-S-R_S$, $-N(R_SR_{S'})$, $-OC(O)R_S$, $-C(O)OR_S$, nitro, phosphate, oxo, thioxo, formyl or cyano;
- $R_E$ is independently selected at each occurrence from $-O-R_S$, $-S-R_S$, $-C(O)R_S$, $-OC(O)R_S$, $-C(O)OR_S$, $-N(R_SR_{S'})$, $-S(O)R_S$, $-SO_2R_S$, $-C(O)N(R_SR_{S'})$, $-N(R_S)C(O)R_{S'}$, $-N(R_S)C(O)N(R_SR_{S''})$, $-N(R_S)SO_2R_{S'}$, $-SO_2N(R_SR_{S'})$, $-N(R_S)SO_2N(R_SR_{S'})$, $-N(R_S)S(O)N(R_SR_{S''})$, $-OS(O)-R_S$, $-OS(O)_2-R_S$, $-S(O)_2OR_S$, $-S(O)OR_S$, $-OC(O)OR_S$, $-N(R_S)C(O)OR_{S'}$, $-OC(O)N(R_SR_{S'})$, $-N(R_S)S(O)-R_{S'}$, $-S(O)N(R_SR_{S'})$, $-C(O)N(R_S)C(O)-R_{S'}$, $C_3-C_{10}$carbocyclyl, or 3- to 10-membered heterocyclyl, wherein said $C_3-C_{10}$carbocyclyl and 3- to 10-membered heterocyclyl are each independently optionally substituted at each occurrence with one or more substituents selected from $C_1-C_6$alkyl, $C_2-C_6$alkenyl, $C_2-C_6$alkynyl, $R_S$ (except hydrogen), halogen, $-O-R_B$, $-S-R_B$, $-N(R_BR_{B'})$, $-OC(O)R_B$, $-C(O)OR_B$, nitro, phosphate, oxo, thioxo, formyl or cyano; and
- $R_S$, $R_{S'}$ and $R_{S''}$ are each independently selected at each occurrence from hydrogen; or $C_1-C_6$alkyl, $C_2$-$C_6$alkenyl, $C_2$-$C_6$alkynyl, $C_3$-$C_6$carbocyclyl, $C_3$-$C_6$carbocylclyl$C_1$-$C_6$alkyl, 3- to 6-membered heterocyclyl, or (3- or 6-membered heterocycyl)$C_1$-$C_6$alkyl, each of which is independently optionally substituted at each occurrence with one or more substituents selected from halogen, —O—$R_B$, —S—$R_B$, —N($R_B R_{B'}$), —OC(O)$R_B$, —C(O)O$R_B$, nitro, phosphate, oxo, thioxo, formyl or cyano.

$Z_1$ preferably is —N($R_B$)—, such as —NH— or —N($C_1$-$C_6$alkyl)-, $X_1$ preferably is —$CH_2$—, —O— or —S.

$R_7$ can be selected, without limitation, $C_5$-$C_6$carbocycle or 5- to 6-membered heterocycle, each of which is optionally substituted with one or more $R_A$. Preferably, $R_7$ is phenyl, and is optionally substituted with one or more $R_A$ (e.g., —N($R_S R_{S'}$) such as —$NH_2$).

$A_2$ can be selected, without limitation, from $C_5$-$C_{10}$carbocycles or 5- to 10-membered heterocycles, and is optionally submitted with one or more $R_A$. Preferably, $A_2$ is selected from $C_5$-$C_6$carbocycles or 5- to 6-membered heterocycles, and is optionally substituted with one or more $R_A$. Two adjacent $R_A$ on $A_2$, taken together with the ring atoms to which they are attached, may form a $C_5$-$C_6$carbocycle or a 5- to 6-membered heterocycle. Non-limiting examples of suitable $A_2$ include phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl, each of which is optionally substituted with one or more $R_A$. As a non-limiting, example, $A_2$ is

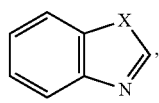

where X is O, S or N($R_B$). T and $R_2$ can be attached to $A_2$ via any two substitutable ring atoms on $A_2$. For instance, $A_2$ can be

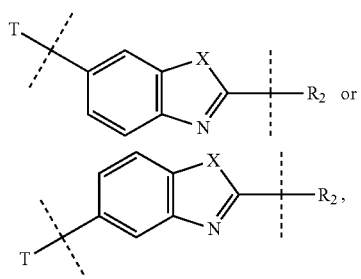

$R_2$ can be —N($R_B$)C(O)C($R_5 R_6$)N($R_8$)-T-$R_D$, where $R_5$ is $R_C$ (e.g., hydrogen) and $R_6$ and $R_8$, taken together with the atoms to which they are attached, form a 5- to 6-membered heterocyclic ring which is optionally substituted with one or more $R_A$. For instance, $R_6$ and $R_8$, taken together with the atoms to which they are attached, can form, without limitation,

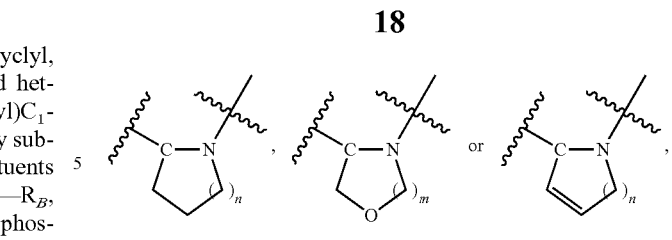

each of which is independently optionally substituted with one or more $R_A$, where n is 0, 1 or 2, and m is 1 or 2. Two adjacent $R_A$, taken together with the atoms to which they are attached, can form a $C_5$-$C_6$carbocycle or a 5- to 6-membered heterocycle.

-T-$R_D$ preferably is —C(O)-$L_S$-$R_{12}$ or —C(O)-$L_S$-M'-$L_{S''}$-$R_{12}$, where $R_{12}$ is (i) hydrogen, (ii) $C_1$-$C_6$alkyl, $C_2$-$C_6$alkenyl or $C_2$-$C_6$alkynyl, each of which is independently optionally substituted at each occurrence with one or more substituents selected from halogen, —O—$R_S$, —S—$R_S$, —N($R_S R_{S'}$), —OC(O)$R_S$, —C(O)O$R_S$, nitro, phosphate, oxo, thioxo, formyl or cyano, or (iii) $C_3$-$C_{10}$carbocyclyl or 3- to 10-membered heterocyclyl, each of which is independently optionally substituted at each occurrence with one or more substituents selected from $C_1$-$C_6$alkyl, $C_2$-$C_6$alkenyl, $C_2$-$C_6$alkynyl, $R_S$ (except hydrogen), halogen, —O—$R_B$, —S—$R_B$, —N($R_B R_{B'}$), —OC(O)$R_B$, —C(O)O$R_B$, nitro, phosphate, oxo, thioxo, formyl or cyano. -T-$R_D$ can also be, without limitation, -$L_S$-($C_3$-$C_6$carbocyclyl) or -$L_S$-(3- to 10-membered heterocyclyl), where said $C_3$-$C_{10}$carbocyclyl and 3- to 10-membered heterocyclyl are each independently optionally substituted with one or more substituents selected from $C_1$-$C_6$alkyl, $C_2$-$C_6$alkenyl, $C_2$-$C_6$alkynyl, $R_S$ (except hydrogen), halogen, —O—$R_B$, —S—$R_B$, —N($R_B R_{B'}$), —OC(O)$R_B$, —C(O)O$R_B$, nitro, phosphate, oxo, thioxo, formyl or cyano. In addition, -T-$R_D$ can be, without limitation, -$L_S$-$R_E$, —C(O)-$L_S$-$R_E$, —C(O)O-$L_S$-$R_E$.

Preferably, $R_2$ is

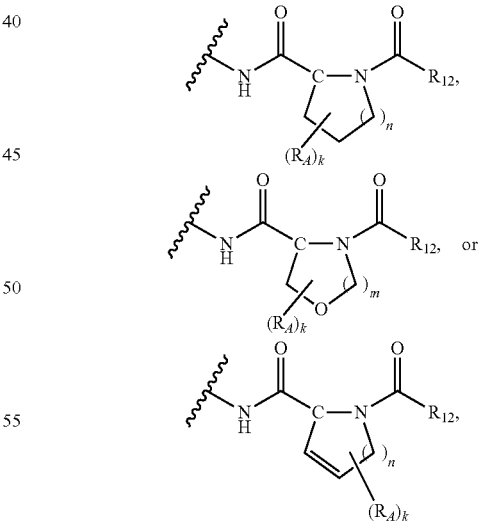

where n is 0, 1 or 2, m is 1 or 2, and k is 0, 1, 2, 3 or 4. Two adjacent $R_A$, taken together with the atoms to which they are attached, can form a $C_5$-$C_6$carbocycle or a 5- to 6-membered heterocycle. $R_{12}$ can be, without limitation, -$L_T$-N($R_B$)-$L_{TT}$-$R_E$, -$L_T$-N($R_B$)C(O)-$L_{TT}$-$R_E$, or -$L_T$-N($R_B$)C(O)-$L_{TT}$-$R_E$, wherein $L_T$ and $L_{TT}$ are each Independently selected from (i) a bond, or (ii) $C_1$-$C_6$alkylene, $C_2$-$C_6$alkenylene, or $C_2$-$C_6$alkynylene, each of which is independently optionally substituted at each occurrence with one or more substituents selected from halogen, $C_3$-$C_{10}$carbocyclyl, 3- to 10-membered heterocyclyl, —O—$R_B$, —S—$R_S$, —N($R_S R_{S'}$), —OC(O)$R_S$, —C(O)O$R_S$, nitro, phosphate, oxo, thioxo, formyl or cyano. Preferably, $R_{12}$ is -$L_T$-N($R_B$)-$L_{TT}$-$R_S$, -$L_T$-N($R_B$)C(O)-$L_{TT}$-$R_S$, or -$L_T$-N($R_B$)C(O)-$L_{TT}$-$R_S$, where $L_T$ and $L_{TT}$ are as defined immediately above. $R_{12}$ can also be, without limitation, -$L_S$-$R_E$, such as -$L_S$-O—$R_S$, -$L_S$-S—$R_S$, or -$L_S$-N($R_S R_{S'}$). In addition, $R_{12}$ can be, without limitation, -$L_S$-($C_5$-$C_{10}$ carbocyclyl) or -$L_S$-(3- to 10-membered heterocyclyl), where said $C_3$-$C_{10}$carbocyclyl and 3- to 10-membered heterocyclyl are each independently optionally substituted with one or more substituents selected from $C_1$-$C_6$alkyl, $C_2$-$C_6$alkenyl, $C_2$-$C_6$alkynyl, $R_S$ (except hydrogen), halogen, —O—$R_B$, —S—$R_B$, —N($R_B R_{B'}$), —OC(O)$R_B$, —C(O)O$R_B$, nitro, phosphate, oxo, thioxo, formyl or cyano.

$R_2$ can also be

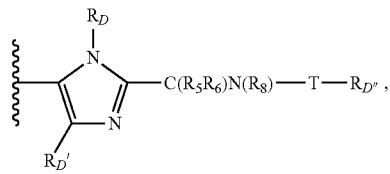

where $R_5$ is $R_C$ (e.g., hydrogen), and $R_6$ and $R_8$, taken together with the atoms to which they are attached, form a 5- to 6-membered heterocyclic ring which is optionally substituted with one or more $R_A$. For instance, $R_6$ and $R_8$, taken together with the atoms to which they are attached, can form, without limitation,

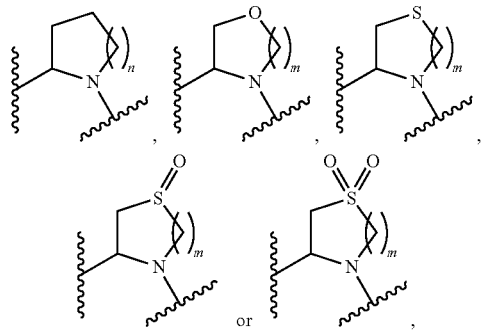

each of which is optionally substituted with one or more $R_A$, where n is 0, 1 or 2, and m is 1 or 2. Two adjacent $R_A$, taken together with the atoms to which they are attached, can form a $C_5$-$C_6$carbocycle or a 5- to 6-membered heterocycle.

-T-$R_{D''}$ can be, without limitation, —C(O)-$L_S$-$R_{12}$ or —C(O)-$L_{S'}$-M'-$L_{S''}$-$R_{12}$, where $R_{12}$ is (i) hydrogen, (ii) $C_1$-$C_6$alkyl, $C_2$-$C_6$alkenyl or $C_2$-$C_6$alkynyl, each of which is independently optionally substituted at each occurrence with one or more substituents selected from halogen, —O—$R_S$, —S—$R_S$, —N($R_S R_{S'}$), —OC(O)$R_S$, —C(O)O$R_S$, nitro, phosphate, oxo, thioxo, formyl or cyano, or (iii) $C_3$-$C_{10}$carbocyclyl or 3- to 10-membered heterocyclyl, each of which is independently optionally substituted at each occurrence with one or more substituents selected from $C_1$-$C_6$alkyl, $C_2$-$C_6$alkenyl, $C_2$-$C_6$alkynyl, $R_S$ (except hydrogen), halogen, —O—$R_B$, —S—$R_B$—N($R_B R_{B'}$), —OC(O)$R_B$, —C(O)O$R_B$, nitro, phosphate, oxo, thioxo, formyl or cyano, -T-$R_{D''}$ can also be, without limitation, -$L_S$-($C_3$-$C_{10}$carbocyclyl) or -$L_S$-(3- to 10-membered heterocyclyl), where said $C_3$-$C_{10}$carbocyclyl and 3- to 10-membered heterocyclyl are each independently optionally substituted with one or more substituents selected from $C_1$-$C_6$alkyl, $C_2$-$C_6$alkenyl, $C_2$-$C_6$alkynyl, $R_S$ (except hydrogen), halogen, —O—$R_B$, —S—$R_B$, —N($R_B R_{B'}$), —OC(O)$R_B$, —C(O)O$R_B$, nitro, phosphate, oxo, thioxo, formyl or cyano. In addition, -T-$R_{D''}$ can be, without limitation, -$L_S$-$R_E$, —C(O)-$L_S$-$R_E$, —C(O)O-$L_S$-$R_E$.

Preferably, $R_2$ is

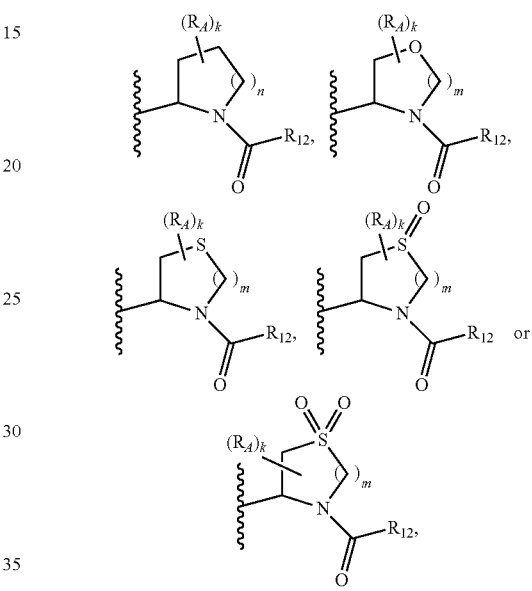

where n is 0, 1 or 2, m is 1 or 2, k is 0, 1, 2, 3 or 4. Two adjacent $R_A$, taken together with the atoms to which they are attached, can form a $C_5$-$C_6$carbocycle or a 5- to 6-membered heterocycle. $R_{12}$ can be, without limitation, -$L_T$-N($R_B$)-$L_{TT}$-$R_E$, -$L_T$-N($R_B$)C(O)-$L_{TT}$-$R_E$, or -$L_T$-N($R_B$)C(O)-$L_{TT}$-$R_E$, wherein $L_T$ and $L_{TT}$ are each independently selected from (i) a bond, or (ii) $C_1$-$C_6$alkylene, $C_2$-$C_6$alkenylene, or $C_2$-$C_6$alkynylene, each of which is independently optionally substituted at each occurrence with one or more substituents selected from halogen, $C_3$-$C_{10}$carbocyclyl, 3- to 10-membered heterocyclyl, —O—$R_S$, —S—$R_S$, —N($R_S R_{S'}$), —OC(O)$R_S$, —C(O)O$R_S$, nitro, phosphate, oxo, thioxo, formyl or cyano. Preferably, $R_{12}$ is -$L_T$-N($R_B$)-$L_{TT}$-$R_S$, -$L_T$-N($R_B$)C(O)-$L_{TT}$-$R_S$, or -$L_T$-N($R_B$)C(O)-$L_{TT}$-$R_S$, where $L_T$ and $L_{TT}$ are as defined immediately above, $R_{12}$ can also be, without limitation, -$L_S$-$R_E$, such as -$L_S$-O—$R_S$, -$L_S$-S—$R_S$, or -$L_S$-N($R_S R_{S'}$). In addition, $R_{12}$ can be, without limitation, -$L_S$-($C_3$-$C_{10}$carbocyclyl) or -$L_S$-(3- to 10-membered heterocyclyl), where said $C_3$-$C_{10}$carbocyclyl and 3- to 10-membered heterocyclyl are each independently optionally substituted with one or more substituents selected from $C_1$-$C_6$alkyl, $C_2$-$C_6$alkenyl, $C_2$-$C_6$alkynyl, $R_S$ (except hydrogen), halogen, —O—$R_B$, —S—$R_B$, —N($R_B R_{B'}$), —OC(O)$R_B$, —C(O)O$R_B$, nitro, phosphate, oxo, thioxo, formyl or cyano.

Furthermore, $R_2$ can be, without limitation, -$L_K$-B, where B is $C_3$-$C_{10}$carbocycle or 3- to 10-membered heterocycle, and is optionally substituted with one or more $R_A$. Non-limiting examples of suitable B include

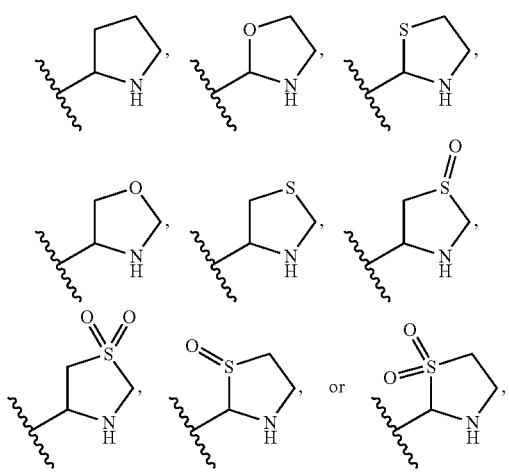

each of which is optionally substituted with one or more $R_A$. Two adjacent $R_A$, taken together with the atoms to which they are attached, can form a $C_5$-$C_6$carbocycle or a 5- to 6-membered heterocycle. Preferred examples of suitable B include

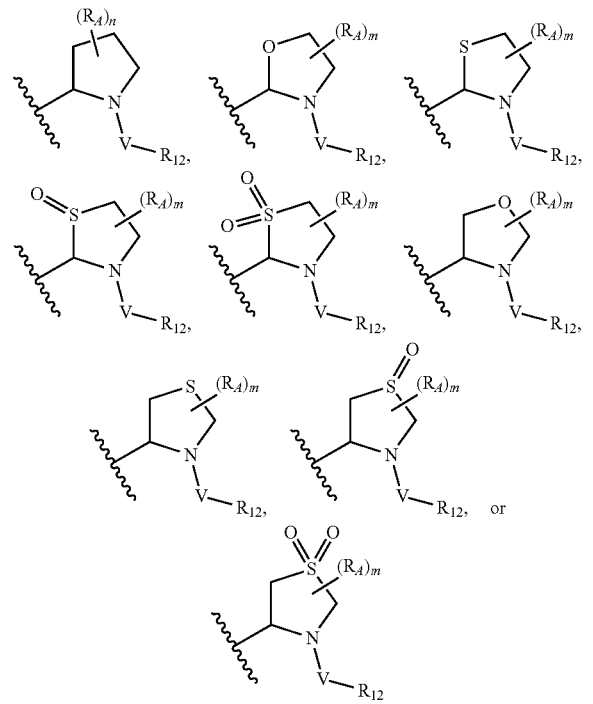

where n is 0, 1, 2, 3 or 4, m is 0, 1, 2 or 3, V is —C(O)— or —S(O)$_2$—, and $R_{12}$ is —$R_S$, —$OR_S$ or —N($R_S R_{S'}$). In one example, $R_2$ is

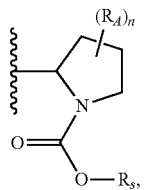

where n is 0, 1, 2, 3 or 4, and two adjacent $R_A$, taken together with the atoms to which they axe attached, can form a $C_5$-$C_6$carbocycle or a 5- to 6-membered heterocycle.

$R_2$ can also be, without limitation,

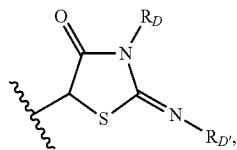

where $R_D$ and $R_{D'}$ are independently selected from (i) $C_1$-$C_6$alkyl, $C_2$-$C_6$alkenyl or $C_2$-$C_6$alkynyl, each of which is independently optionally substituted at each occurrence with one or more substituents selected from halogen, —O—$R_S$, —S—$R_S$, —N($R_S R_{S'}$), —OC(O)$R_S$, —C(O)O$R_S$, nitro, phosphate, oxo, thioxo, formyl or cyano; (ii) -$L_S$-$C_3$-$C_{10}$carbocyclyl or -$L_S$-(3- to 10-membered heterocyclyl), each of which is optionally substituted with one or more substituents selected from $C_1$-$C_6$alkyl $C_2$-$C_6$alkenyl, $C_2$-$C_6$alkynyl, $R_S$ (except hydrogen), halogen, —O—$R_B$, —S—$R_B$, —N($R_B R_{B'}$), —OC(O)$R_B$, —C(O)O$R_B$, nitro, phosphate, oxo, thioxo, formyl or cyano; or (iii) -$L_S$-O—$R_S$, -$L_S$-S—$R_S$, or -$L_S$-N($R_S R_{S'}$). Alternatively, $R_D$ and $R_{D'}$ can join to form a 5- to 6-membered heterocycle.

T can be selected, without limitation, from the following moieties:

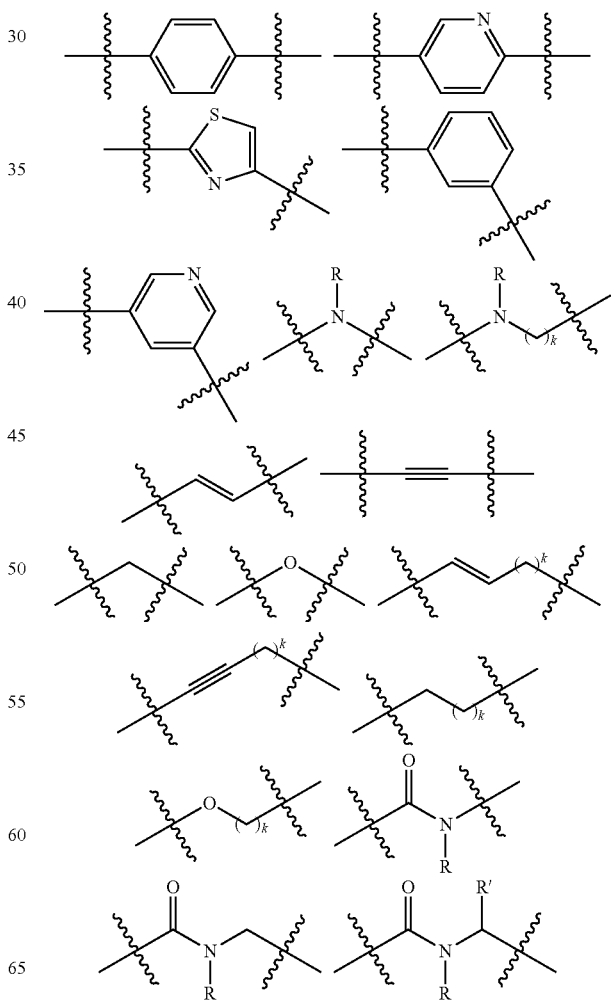

-continued

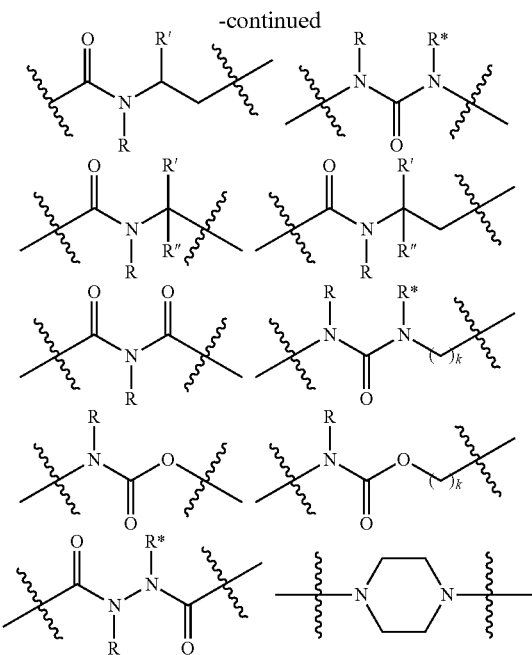

where k is 1 or 2, R and R* are independently hydrogen or $C_1$-$C_6$alkyl, and R' and R" are independently $C_1$-$C_6$alkyl or $C_6$-$C_{10}$aryl.

Preferably, T is selected from Table 4 described below.

More preferably, T is -$L_S$-N($R_T$)-$L_{S'}$- (e.g., —$CH_2$—N($R_T$)—$CH_S$—), or -$L_S$-C($R_T R_{T'}$)-$L_{S'}$- (e.g., —$CH_2$—C($R_T R_{T'}$)—$CH_2$—). $R_T$ is $C_2$-$C_6$alkyl, $C_2$-$C_6$alkenyl, or $C_2$-$C_6$alkynyl, each of which is independently optionally substituted at each occurrence with one or more substituents selected from halogen, —O—$R_S$, —S—$R_S$, —N($R_S R_{S'}$), —OC(O)$R_S$, —C(O)O$R_S$, nitro, phosphate, oxo, thioxo, formyl or cyano; or $R_T$ is $C_3$-$C_6$carbocyclyl, $C_3$-$C_6$carbocyclyl$C_1$-$C_6$alkyl, 3- to 6-membered heterocyclyl, or (3- or 6-membered heterocyclyl)$C_1$-$C_6$alkyl, each of which is independently optionally substituted at each occurrence with one or more substituents selected from $C_1$-$C_6$alkyl, $C_2$-$C_6$alkenyl, $C_2$-$C_6$alkynyl, $R_S$ (except hydrogen), halogen, —O—$R_B$, —S—$R_B$, —N($R_B R_{B'}$), —OC(O)$R_B$, —C(O)O$R_B$, nitro, phosphate, oxo, thioxo, formyl or cyano. $R_{T'}$ is $R_A$, and preferably $R_{T'}$ is hydrogen. $L_S$, $L_{S'}$, $R_A$, $R_B$, $R_{B'}$, $R_S$, and $R_{S'}$ are as defined above.

In one embodiment, $A_2$ is 5- to 10-membered carbocycle or heterocycle (e.g., phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl) and is optionally substituted with one or more $R_A$. Preferably, $A_2$ is 5- to 6-membered carbocycle or heterocycle (e.g., phenyl), and is optionally substituted with one or more $R_A$; $X_1$ is selected from —$CH_2$—, —O—, or —S—; $R_7$ is selected from 5- to 6-membered carbocycles or heterocycles, and is optionally substituted with one or more $R_A$; and $Z_1$ is —N($R_B$)— (e.g., —NH— or —N($C_1$-$C_6$alkyl)-).

In another embodiment, $W_1$, $W_2$, and $W_5$ are N, and $W_6$ is C($R_F$); $R_1$ is hydrogen; $R_7$ is phenyl, and is optionally substituted with one or more $R_A$; and $R_9$, $R_{11}$, and $R_F$ are each independently selected at each occurrence from hydrogen; halogen; $C_1$-$C_6$alkyl, $C_2$-$C_6$alkenyl, $C_2$-$C_6$alkynyl, $C_3$-$C_6$carbocyclyl, or $C_3$-$C_6$carbocyclyl$C_1$-$C_6$alkyl, each of which is independently optionally substituted at each occurrence with one or more substituents selected front halogen, hydroxy, mercapto, amino, carboxy, nitro, phosphate, oxo, thioxo, formyl or cyano. Preferably, $R_9$ is $C_1$-$C_6$alkyl, $C_2$-$C_6$alkenyl, $C_2$-$C_6$alkynyl, $C_3$-$C_6$carbocyclyl (e.g., $C_3$-$C_6$cycloalkyl), or $C_3$-$C_6$carbocyclyl$C_3$-$C_6$alkyl, (e.g., $C_3$-$C_6$cycloalkyl$C_1$-$C_6$alkyl), each of which is independently optionally substituted at each occurrence with one or more substituents selected from halogen, hydroxy, mercapto, amino, carboxy, nitro, phosphate, oxo, thioxo, formyl or cyano; and $R_{11}$ and $R_F$ are hydrogen. $Z_1$ can be —N($R_B$)— (e.g., —NH— or —N($C_1$-$C_6$alkyl)-); $C_1$ is —$CH_2$—, —O—, or —S—; and $A_2$ can be 5- to 10-membered carbocycle or heterocycle (e.g., phenyl, pyrazinyl, pyridinyl, pyrimidinyl, pyridazinyl, oxazolyl, thiazolyl, thienyl, furanyl, imidazolyl, pyrazolyl, triazolyl, benzoxazolyl, benzothienyl, benzimidazolyl, benzofuranyl, benzothiazolyl, indolyl, indenyl, naphthalenyl, quinolinyl, isoquinolinyl, quinoxalinyl, cinnolinyl, quinazolinyl, or phthalazinyl), and is optionally substituted with one or more $R_A$. Preferably, $A_2$ is 5- to 6-membered carbocycle or heterocycle (e.g., phenyl), and is optionally substituted with one or more $R_A$.

In yet another embodiment, where

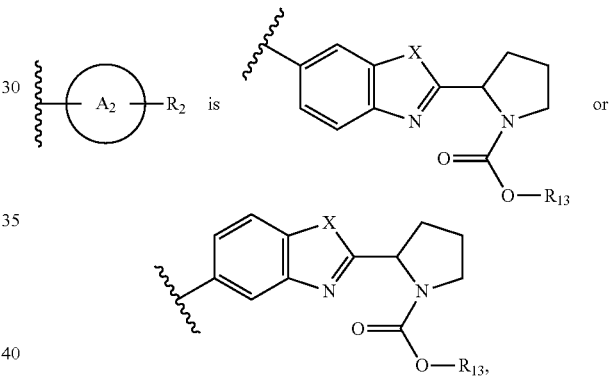

X is O, S or N($R_B$), and $R_{13}$ is $R_S$. Preferably, $R_{13}$ is $C_1$-$C_6$alkyl, $C_2$-$C_6$alkenyl, $C_2$-$C_6$alkynyl, $C_3$-$C_6$carbocyclyl, $C_3$-$C_6$carbocyclyl$C_1$-$C_6$alkyl, 3- to 6-membered heterocyclyl, or (3- or 6-membered heterocyclyl)$C_1$-$C_6$alkyl, each of which is independently optionally substituted at each occurrence with one or more substituents selected from halogen, —O—$R_B$, —S—$R_B$, —N($R_B R_{B'}$), —OC(O)$R_B$, —C(O)O$R_B$, nitro, phosphate, oxo, thioxo, formyl or cyano; and X is O, S, NH or N($C_1$-$C_6$alkyl).

The compounds of the present invention can be used in the form of salts. Depending on the particular compound, a salt of a compound may be advantageous due to one or more of the salt's physical properties, such as enhanced pharmaceutical stability under certain conditions or desired solubility in water or oil. In some instances, a salt of a compound may be useful for the isolation or purification of the compound.

Where a salt is intended to be administered to a patient, the salt preferably is pharmaceutically acceptable. Pharmaceutically acceptable salts include, but are not limited to, acid addition salts, base addition salts, and alkali metal salts.

Pharmaceutically acceptable acid addition salts may be prepared from inorganic or organic acids. Examples of suitable inorganic acids include, but are not limited to, hydrochloric, hydrobromic acid, hydroionic, nitric, carbonic, sulfuric, and phosphoric acid. Examples of suitable organic acids include, but are not limited to, aliphatic, cycloaliphatic, aromatic, araliphatic, heterocyclyl, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesolfonate, 2-hydroxyethanesulfonate, sufanilate, cyclohexylaminosulfonate, algenic acid, b-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, hemisulfate, heptanoate, hexanoate, nicotinate, 2-napthalesulfonate, oxalate, palmoate, pectinate, persulfate, 3-phenylpropionate, picrate, pivalate, thiocyanate, tosylate, and undecanoate.

Pharmaceutically acceptable base addition salts include, but are not limited to, metallic salts and organic salts. Non-limiting examples of suitable metallic salts include alkali metal (group Ia) salts, alkaline earth metal (group IIa) salts, and other pharmaceutically acceptable metal salts. Such salts may be made, without limitation, from aluminum, calcium, lithium, magnesium, potassium, sodium, or zinc. Non-limiting examples of suitable organic salts can be made from tertiary amines and quaternary amine, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as alkyl halides (e.g., methyl, ethyl, propyl, butyl, decyl, lauryl, myristyl, and stearyl chlorides/bromides/iodides), dialkyl sulfates (e.g., dimethyl, diethyl, dibuytl, and diamyl sulfates), aralkyl halides (e.g., benzyl and phenethyl bromides), and others.

The compounds or salts of the present invention may exist in the form of solvates, such as with water (i.e., hydrates), or with organic solvents (e.g., with methanol, ethanol or acetonitrile to form, respectively, methanolate, ethanolate or acetonitrilate).

The compounds or salts of the present invention may also be used in the form of prodrugs. Some prodrugs are aliphatic or aromatic esters derived from acidic groups on the compounds of the invention. Others are aliphatic or aromatic esters of hydroxyl or amino groups on the compounds of the invention. Phosphate prodrugs of hydroxyl groups are preferred prodrugs.

The compounds of the invention may comprise asymmetrically substituted carbon atoms known as chiral centers. These compounds may exist, without limitation, as single stereoisomers (e.g., single enantiomers or single diastereomers), mixtures of stereoisomers (e.g. a mixture of enantiomers or diastereomers), or racemic mixtures. Compounds identified herein as single stereoisomers are meant to describe compounds that are present in a form that is substantially free from other stereoisomers (e.g., substantially free from other enantiomers or diastereomers). By "substantially free," it means that at least 80% of the compound in a composition is the described stereoisomer; preferably, at least 90% of the compound in a composition is the described stereoisomer; and more preferably, at least 95%, 96%, 97%, 98% or 99% of the compound in a composition is the described stereoisomer. Where the stereochemistry of a chiral carbon is not specified in the chemical structure of a compound, the chemical structure is intended to encompass compounds containing either stereoisomer of the chiral center.

Individual stereoisomers of the compounds of this invention can be prepared using a variety of methods known in the art. These methods include, but are not limited to, stereospecific synthesis, chromatographic separation of diastereomers, chromatographic resolution of enantiomers, conversion of enantiomers is an enantiomeric mixture to diastereomers followed by chromatographically separation of the diastereomers and regeneration of the individual enantiomers, and enzymatic resolution.

Stereospecific synthesis typically involves the use of appropriate optically pure (enantiomerically pure) or substantial optically pure materials and synthetic reactions that do not cause racemization or inversion of stereochemistry at the chiral centers. Mixtures of stereoisomers of compounds, including racemic mixtures, resulting from a synthetic reaction may be separated, for example, by chromatographic techniques as appreciated by those of ordinary skill in the art. Chromatographic resolution of enantiomers can be accomplished by using chiral chromatography resins, many of which are commercially available. In a non-limiting example, racemate is placed in solution and loaded onto the column containing a chiral stationary phase. Enantiomers can then be separated by HPLC.

Resolution of enantiomers can also be accomplished by converting enantiomers in a mixture to diastereomers by reaction with chiral auxiliaries. The resulting diastereomers can be separated by column chromatography or crystallization/re-crystallization. This technique is useful when the compounds to be separated contain a carboxyl, amino or hydroxyl group that will form a salt or covalent bond with the chiral auxiliary. Non-limiting examples of suitable chiral auxiliaries include chirally pure amino acids, organic carboxylic acids or organosulfonic acids. Once the diastereomers are separated by chromatography, the individual enantiomers can be regenerated. Frequently, the chiral auxiliary can be recovered and used again.

Enzymes, such as esterases, phosphatases or lipases, can be useful for the resolution of derivatives of enantiomers in an enantiomeric mixture. For example, an ester derivative of a carboxyl group in the compounds to be separated can be treated with an enzyme which selectively hydrolyzes only one of the enantiomers in the mixture. The resulting enantiomerically pure acid can then be separated from the unhydrolyzed ester.

Alternatively, salts of enantiomers in a mixture can be prepared using any method known in the art, including treatment of the carboxylic acid with a suitable optically pure base such as alkaloids or phenethylamine, followed by precipitation or crystallization/re-crystallization of the enantiomerically pure salts. Methods suitable for the resolution/separation of a mixture of stereoisomers. Including racemic mixtures, can be found in ENANTIOMERS, RACEMATES, AND RESOLUTIONS (Jacques et al., 1981, John Wiley and Sons, New York, N.Y.).

A compound of this invention may possess one or more unsaturated carbon-carbon double bonds. All double bond isomers, such as the cis (Z) and trans (E) isomers, and mixtures thereof are intended to be encompassed within the scope of a recited compound unless otherwise specified. In addition, where a compound exists in various tautomeric forms, a recited compound is not limited to any one specific tautomer, but rather is intended to encompass all tautomeric forms.

Certain compounds of the invention may exist in different stable conformational forms which may be separable. Torsional asymmetry due to restricted rotations about an asymmetric single bond, for example because of steric hindrance or ring strain, may permit separation of different conformers. The compounds of the invention includes each conformational isomer of these compounds and mixtures thereof.

Certain compounds of the invention may also exist in zwitterionic form and the invention includes each zwitterionic form of these compounds and mixtures thereof.

The compounds of the present invention are generally described herein using standard nomenclature. For a recited compound having asymmetric center(s), it should be understood that all of the stereoisomers of the compound and mixtures thereof are encompassed in the present invention unless otherwise specified. Non-limiting examples of stereoisomers include enantiomers, diastereomers, and cis-transisomers. Where a recited compound exists in various tautomeric forms, the compound is intended to encompass all tautomeric forms. Certain compounds are described herein using general formulas that include variables (e.g., $A_1$, $A_2$, $Z_1$, T, $R_B$, or $R_A$). Unless otherwise specified, each variable within such a formula is defined independently of any other variable, and any variable that occurs more than one time in a formula is defined independently at each occurrence. If moieties are described as being "independently" selected from a group, each moiety is selected independently from the other, Each moiety therefore can be identical to or different from the other moiety or moieties.

The number of carbon atoms in it hydrocarbyl moiety can be indicated by the prefix "$C_x$-$C_y$," where x is the minimum and y is the maximum number of carbon atoms in the moiety. Thus, for example, "$C_1$-$C_6$alkyl" refers to an alkyl substituent containing from 1 to 6 carbon atoms. Illustrating further, $C_3$-$C_6$cycloalkyl means a saturated hydrocarbyl ring containing from 3 to 6 carbon ring atoms. A prefix attached to a multiple-component substituent only applies to the first component that immediately follows the prefix. To illustrate, the term "carbocyclylalkyl" contains two components: carbocyclyl and alkyl. Thus, for example, $C_3$-$C_6$carbocyelyl$C_1$-$C_6$alkyl refers to a $C_3$-$C_6$carbocyclyl appended to the parent molecular moiety through a $C_1$-$C_6$alkyl group.

When words are used to describe a linking element between two other demerits of a depicted chemical structure, the leftmost-described component of the linking element is the component that is bound to the left element in the depicted structure. To illustrate, if the chemical structure is $A_1$-T-$A_2$ and T is described as —N($R_B$)S(O)—, then the chemical will $A_1$-N($R_B$)—S(O)-$A_2$.

If a linking element in a depicted structure is a bond, then the left element in the depicted structure is joined directly to the right element in the depicted structure. For example, if a chemical structure is depicted as -$L_S$-M-$L_{S'}$-, where M is selected as a bond, then the chemical structure will be -$L_S$-$L_{S'}$-. For another example, if a chemical moiety is depicted as -$L_S$-$R_E$ where $L_S$ is selected as a bond, then die chemical moiety will be —$R_E$.

When a chemical formula is used to describe a moiety, the dash(s) indicates the portion of the moiety that has the free valence(s).

If a moiety is described as being "optionally substituted", the moiety may be either substituted or unsubstituted. If a moiety is described as being optionally substituted with up to a particular number of non-hydrogen radicals, that moiety may be either unsubstituted, or substituted by up to that particular number of non-hydrogen radicals or by up to the maximum number of substitutable positions on the moiety, whichever is less. Thus, for example, if a moiety is described as a heterocycle optionally substituted with up to three non-hydrogen radicals, then any heterocycle with less than three substitutable positions will be optionally substituted by up to only as many non-hydrogen radicals as the heterocycle has substitutable positions. To illustrate, tetrazolyl (which has only one substitutable position) will be optionally substituted with up to one non-hydrogen radical. To illustrate further, if an amino nitrogen is described as being optionally substituted with up to two non-hydrogen radicals, then a primary amino nitrogen will be optionally substituted with up to two non-hydrogen radicals, whereas a secondary amino nitrogen will be optionally substituted with up to only one non-hydrogen radical.

The term "alkenyl" means a straight or branched hydrocarbyl chain containing one or more double bonds. Each carbon-carbon double bond may have either cis or trans geometry within the alkenyl moiety, relative to groups substituted on the double bond carbons. Non-limiting examples of alkenyl groups include ethenyl (vinyl), 2-propenyl, 3-propenyl, 1,4-pentadienyl, 1,4-butadienyl, 1-butenyl, 2-butenyl, and 3-butenyl.

The term "alkenylene" refers to a divalent unsaturated hydrocarbyl chain which may be linear or branched and which has at least one carbon-carbon double bond. Non-limiting examples of alkenylene groups include —C(H)═C(H)—, —C(H)═C(H)—CH—, —C(H)═C(H)—$CH_2$—$CH_2$—, —$CH_2$—C(H)═C(H)—$CH_2$—, —C(H)═C(H)—CH($CH_3$)—, and —$CH_2$—C(H)═C(H)—CH($CH_2CH_3$)—.

The term "alkyl" means a straight or branched saturated hydrocarbyl chain. Non-limiting examples of alkyl groups include methyl, ethyl, n-propyl, isopropyl, n-butyl, isobutyl, sec-butyl, t-butyl, pentyl, iso-amyl, and hexyl.

The term "alkylene" denotes a divalent saturated hydrocarbyl chain which may be linear or branched. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkynyl" means a straight or branched hydrocarbyl chain containing one or more triple bonds. Non-limiting examples of alkynyl include ethynyl, 1-propynyl, 2-propynyl, 3-propynyl, decynyl, 1-butynyl, 2-butynyl, and 3-butynyl.

The term "alkynylene" refers to a divalent unsaturated hydrocarbon group which may be linear or branched and which has at least one carbon-carbon triple beards. Representative alkynylene groups include, by way of example, —C≡C—, —C≡C—$CH_2$—, —C≡C—$CH_2$—$CH_2$—, —$CH_2$—C≡C—$CH_2$—, —C≡C—CH($CH_3$)—, and —$CH_2$—C≡C—CH($CH_2CH_3$)—.

The term "carbocycle" or "carbocyclic" or "carbocyclyl" refers to a saturated (e.g., "cycloalkyl"), partially saturated (e.g., "cycloalkenyl" or "cycloalkynyl") or completely unsaturated (e.g., "aryl") ring system containing zero heteroatom ring atom. "Ring atoms" or "ring members" are the atoms bound together to form the ring or rings. A carbocyclyl may be, without limitation, a single ring, two fused rings, or bridged or spiro rings. A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydro-indenyl, cyclohexenyl, phenyl, naphthyl, indanyl, 1,2,3,4-tetrahydro-naphthyl, indenyl, isoindenyl, decalinyl, and norpinanyl. A carbocyclyl group can be attached to the parent molecular moiety through any substitutable carbon ring atom. Where a carbocyclyl group is a divalent moiety, such as $A_1$ and $A_2$ in Formula I, it can be attached to the remaining molecular moiety through any two substitutable ring atoms.

The term "carbocyclylalkyl" refers to a carbocyclyl group appended to the parent molecular moiety through an alkylene group. For instance, $C_3$-$C_6$carbocyclyl$C_1$-$C_6$alkyl refers to a $C_3$-$C_6$carbocyclyl group appended to the parent molecular moiety through $C_1$-$C_6$alkylene.

The term "cycloalkenyl" refers to a non-aromatic, partially unsaturated carbocyclyl moiety having zero heteroatom ring member. Representative examples of cycloalkenyl groups include, but are not limited to, cyclobutenyl, cyclopentenyl, cyclohexenyl, and octahydronaphthalenyl.

The term "cycloalkyl" refers to a saturated carbocyclyl group containing zero heteroatom ring member. Non-limiting examples of cycloalkyls include cyclopropyl, cyclobutyl, cyclopentyl, cyclohexyl, cycloheptyl, cyclooctyl, decalinyl and norpinanyl.

The prefix "halo" indicates that the substituent to which the prefix is attached is substituted with one or more independently selected halogen radicals. For example, "$C_1$-$C_6$haloalkyl" means a $C_1$-$C_6$alkyl substituent wherein one or more hydrogen atoms are replaced with independently selected halogen radicals. Non-limiting examples of $C_1$-$C_6$haloalkyl include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The term "heterocycle" or "heterocyclo" or "heterocyclyl" refers to a saturated (e.g., "heterocycloalkyl"), partially unsaturated (e.g., "heterocycloalkenyl" or "heterocycloalkynyl") or completely unsaturated (e.g., "heteroaryl") ring system where at least one of the ring atoms is a heteroatom (i.e., nitrogen, oxygen or sulfur), with the remaining ring atoms being independently selected from the group consisting of carbon, nitrogen, oxygen and sulfur. A heterocyclyl group can be linked to the parent molecular moiety via any substitutable carbon or nitrogen atom(s) in the group. Where a heterocyclyl group is a divalent moiety, such as $A_1$ and $A_2$ in Formula I, it can be attached to the remaining molecular moiety through any two substitutable ring atoms.

A heterocyclyl may be, without limitation, a monocycle which contains a single ring. Non-limiting examples of monocycles include furanyl, dihydrofuranyl, tetrahydrofuranyl, pyrrolyl, isopyrrolyl, pyrrolinyl, pyrrolidinyl, imidazolyl, isoimidazolyl, isoimidazolinyl, imidazolidinyl, pyrazolyl, pyrazolinyl, pyrazolidinyl, triazolyl, tetrazolyl, dithiolyl, oxathlolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl, oxatriazolyl (including 1,2,3,4-oxatriazolyl and 1,2,3,5-oxatriazolyl), dioxazolyl (including 1,2,3-dioxazolyl, 1,2,4-dioxazolyl, 1,3,2-dioxazolyl, and 1,3,4-dioxazolyl), oxathiolanyl, pyranyl (including 1,2-pyranyl and 1,4-pyranyl), dihydropyranyl, pyridinyl, piperidinyl, diazinyl (including pyridazinyl (also known as "1,2-diazinyl"), pyrimidinyl (also known as "1,3-diazinyl"), and pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl), oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxazolidinyl, isoxazolidinyl, oxathlazinyl (including 1,2,5-oxathiazinyl or 1,2,6-oxathiazinyl), oxadiazinyl (including 1,4,2-oxadiazinyl and 1,3,5,2-oxadiazinyl), morpholinyl, azepinyl, oxepinyl, thiepinyl, and diazepinyl.

A heterocyclyl may also be, without limitation, a bicycle containing two fused rings, such as, for example, naphthyridinyl (including [1,8]naphthyridinyl, and [1,6]naphthyridinyl), thiazolpyrimidinyl, thienopyrimidinyl, pyrimidopyrimidinyl, pyridopyrimidinyl, pyrazolopyrimidinyl, indolizinyl, pyrindinyl, pyranopyrrolyl, 4H-quinolizinyl, purinyl, pyridopyridinyl (including pyrido[3,4-b]-pyridinyl, pyrido[3,2-b]-pyridinyl, and pyrido[4,3-b]-pyridinyl), pyridopyrimidine, and pteridinyl. Other non-limiting examples of fused-ring heterocycles include benzo-fused heterocyclyls, such as indolyl, isoindolyl, indoleninyl (also known as "pseudoindolyl"), isoindazolyl (also known as "benzpyrazolyl"), benzazinyl (including quinolinyl (also known as "1-benzazinyl") and isoquinolinyl (also known as "2-benzazinyl")), phthalazinyl, quinoxalinyl, benzodiazinyl (including cinnolinyl (also known as "1,2-benzodiazinyl") and quinazolinyl (also known as "1,3-benzodiazinyl")), benzopyranyl (including "chromenyl" and "isochromenyl"), benzothiopyranyl (also known as "thiochromenyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl", "thionaphthenyl", and "benzothiofuranyl"), isobenzothienyl (also known as "isobenzothiophenyl", "isothionaphthenyl", and "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, and 3,1,4-benzoxazinyl), benzoxazinyl (including 1,2-benzisoxazinyl and 1,4-benzisoxazinyl), and tetrahydroisoquinolinyl.

A heterocyclyl may comprise one or mote sulfur atoms as ring members; and in some cases, the sulfur atom(s) is oxidized to SO or $SO_2$. The nitrogen heteroatom(s) is a heterocyclyl may or may not be quaternized, and may or may not be oxidized to N-oxide. In addition, the nitrogen heteroatom(s) may or may not be N-protected.

The term "pharmaceutically acceptable" is used adjectivally to mean that the modified noun is appropriate for use as a pharmaceutical product or as apart of a pharmaceutical product.

The term "therapeutically effective amount" refers to the total amount of each active substance that is sufficient to show a meaningful patient benefit, e.g. a reduction in viral load.

The term "prodrug" refers to derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner by reaction of a functional group of the compound (such as an amino, hydroxy or carboxy group). Prodrugs often offer advantages of solubility, tissue compatibility, or delayed release in mammals (see, Bungard, H., DESIGN OF PRODRUGS, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Examples of prodrugs include, but are not limited to, acetate, formate, benzoate or other acylated derivatives of alcohol or amine functional groups within the compounds of the invention.

The term "solvate" refers to the physical association of a compound of this invention with one or more solvent molecules, whether organic or inorganic. This physical association often includes hydrogen bonding. In certain instances the solvate will be capable of isolation, for example when one or more solvent molecules are incorporated in the crystal lattice of the crystalline solid, "Solvate" encompasses both solution-phase and isolable solvates. Exemplary solvates include, but are not limited to, hydrates, ethanolates, and methanolates.

The term "N-protecting group" or "N-protected" refers to those groups capable of protecting an amino group against undesirable reactions. Commonly used N-protecting groups are described in Greene and Wuts, PROTECTING GROUPS IN CHEMICAL SYNTHESIS (3$^{rd}$ ed., John Wiley & Sons, NY (1999). Non-limiting examples of N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, or 4-nitrobenzoyl; sulfonyl groups such as benzenesulfonyl or p-toluenesulfonyl; sulfenyl groups such as phenylsulfenyl (phenyl-S(O)—) or triphenylmethylsulfenyl (trityl-S—); sulfinyl groups such as p-methylphenylsulfinyl (p-methylphenyl-S(O)—) or t-butylsulfinyl (t-Bu-S(O)—); carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimedioxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl-1-methylethoxycarbonyl, dimethyl-3,3-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloro-ethoxy-carbonyl, phenoxycarbonyl, 4-nitro-phenoxycarbonyl, cyclopentyloxycarbonyl, adamantyloxycarbonyl, cyclohexyloxycarbonyl, or phenylthiocarbonyl; alkyl groups such as benzyl, p-methoxybenzyl, triphenylmethyl, or benzyloxymethyl; p-methoxyphenyl; and silyl groups such as trimethylsilyl. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

The compounds of the present invention can be prepared by coupling a compound of Formula IV to a compound of Formula V as showed in Scheme I, where $A_1, A_2, Z_1, W_1, W_2, R_1, R_2, R_3, R_4$, and T are as defined hereinabove. Compounds of Formula IV can be prepared according to the processes described in U.S. Patent Application Publication Nos. 20070232627, 20070197558 and 20070232645 and WO2008/133753, while compounds of Formula V can be prepared according to the procedures described in WO2004014313, WO2004014852, WO2006133326, WO2007070556, WO2007070600, WO2008021927, WO2008021928, WO2008021936, WO2008064218, and WO2008070447.

Scheme I

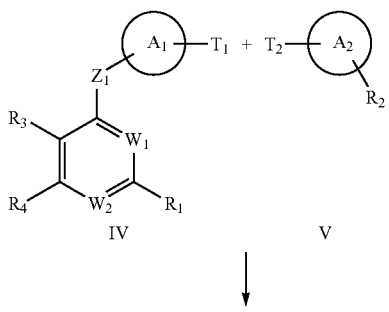

As a non-limiting example, the compounds of the present invention can be prepared by coupling a compound of Formula IV to a compound of Formula V as shown in Scheme II, where $T_1$ is a carboxylic acid as shown or an activated derivative such as an acid chloride or an activated ester (e.g., N-hydroxysuccinimide or pentafluorophenyl esters), and $T_2$ is an amine or substituted amine. Amide bond coupling reagents such as DCC, EDAC, PyBOP, and HATU may be employed with the option of adding an amine base such as triethylamine or Hunig's base in a solvent such as DMF, DMSO, THF, or dichloromethane.

Scheme II

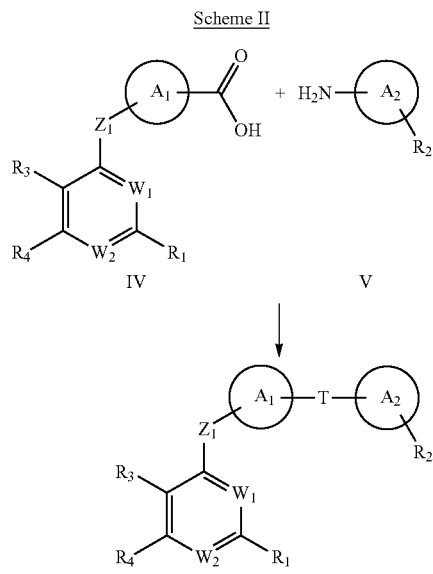

As another non-limiting example, the compounds of the present invention can be prepared by coupling a compound of Formula IV to a compound of Formula V as shown in Scheme III, where $T_1$ and $T_2$ are carboxylic acids or activated derivatives such as acid chlorides or activated esters (e.g., N-hydroxysuccinimide or pentafluorophenyl esters) by reaction with an amine or substituted amine as shown. Amide bond coupling reagents such as DCC, EDAC, PyBOP, and HATU may be employed with the option of adding an amine base such as triethylamine or Hunig's base in a solvent such as DMF, DMSO, THF, or dichloromethane. Couplings may be conducted concurrently to give symmetric products or sequentially to give non-symmetric products. $R_B$ and $R_{B'}$ are as defined hereinabove, and —C(O)N($R_B$)-T'-N($R_{B'}$)C(O)— is T.

Scheme III

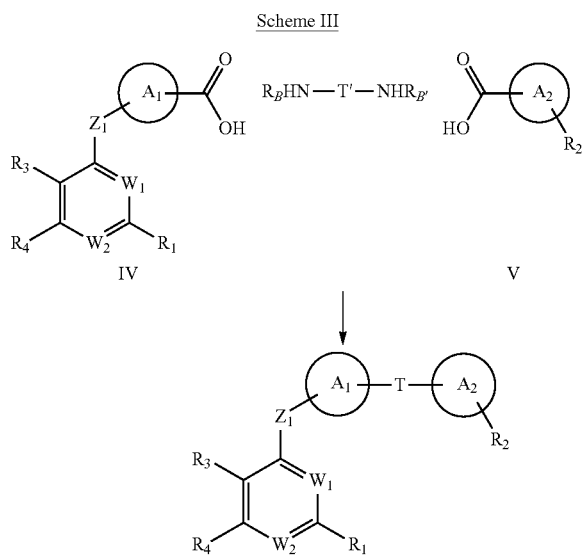

As yet another non-limiting example, the compounds of the present invention can be prepared by coupling a compound of Formula IV to a compound of Formula V as shown in Scheme IV, where $T_1$ and $T_2$ are independently boronic acids or esters as shown by reaction with heterocyclic or carbocyclic halides (iodide shown in Scheme IV) or triflates and a transition metal catalyst. T' is a heterocyclic or carbocyclic, and R can be, without limitation, independently selected at each occurrence from hydrogen or $L_A$, and $L_A$ is as defined hereinabove. Alternatively, alkyl stannanes (such a tributyl- or trimethylstannanes) may be employed in place of the boronates and coupled with halides or inflates under analogous conditions. Pd catalysts such as $Pd(PPh_3)_4$ or $Pd(dppf)Cl_2$ may be employed or generated in situ using a Pd (II) catalyst such $Pd(OAc)_2$ or $Pd_2(dba)_3$ and organophosphorous ligands, such as $PPh_3$ or $P(t\text{-}Bu)_3$. Reactions may be conducted with addition of a base such $K_2CO_3$ or $K_3PO_4$ in a solvent such as THF or DMF. Couplings may be conducted concurrently to give symmetric products or sequentially to give non-symmetric products.

Scheme IV

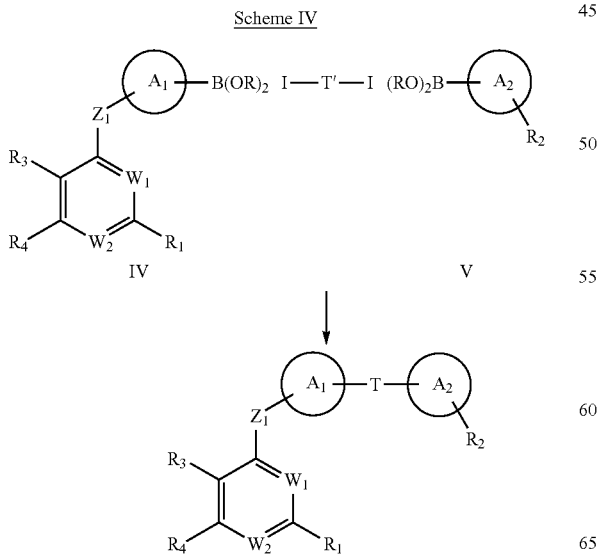

As still another non-limiting example, the compounds of the present invention can be prepared by coupling a compound of Formula IV to a compound of Formula V as shown in Scheme V, where $T_1$ and $T_2$ are halides (iodide as shown) by reaction with an alkyne, where R may be trimethylsilyl (TMS) or another suitable protecting group, by Sonogashira reaction using a suitable catalyst. Pd catalysts such as $Pd(PPh_3)_4$ or $Pd(dppf)Cl_2$ may be employed or generated in situ using a Pd (II) catalyst such $Pd(OAc)_2$ or $Pd_2(dba)_3$ and organophosphorous ligands, such as $PPh_3$ or $P(t\text{-}Bu)_3$. Alternatively, a Cu (I) catalyst may be employed, such as Cu (I) iodide. Reactions may be conducted with addition of a base such $K_2CO_3$ or $K_3PO_4$ or an amine base such as triethylamine or Hunig's base in a solvent such as THF or DMF. The TMS protecting group may be removed using a base such as $K_2CO_3$ in a solvent such as methanol or THF. A second Sonogashira reaction with V may be conducted under the analogous conditions to the first coupling. Couplings may be conducted concurrently to give symmetric products or sequentially to give non-symmetric products.

Scheme V

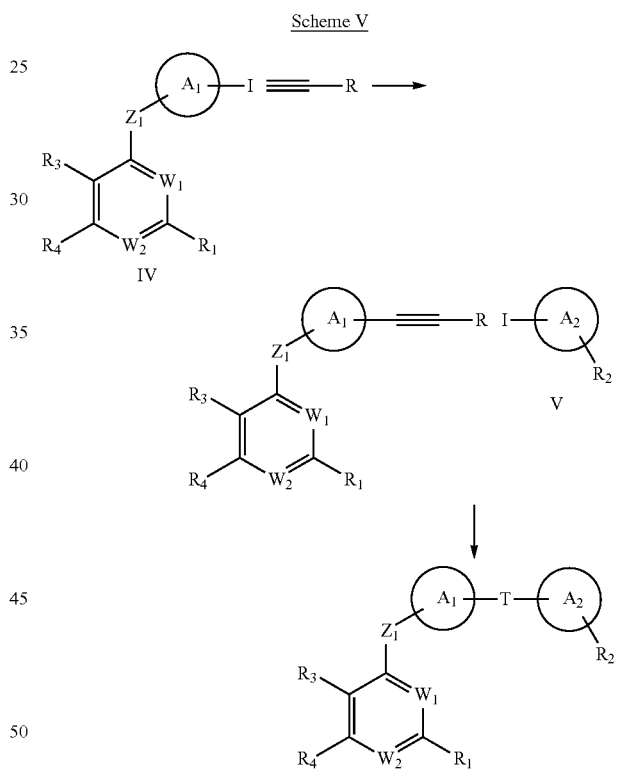

As a further non-limiting example, the compounds of the present Invention can be prepared by coupling a compound of Formula IV to a compound of Formula V as shown in Scheme VI. Formula IV and V are both aldehydes, and can be reacted with an amine to form Formula VI (step 1) by reductive animation using a suitable reducing agent such as $NaCNBH_3$ or $NaBH(OAc)_3$, in a solvent such as THF or ethanol with or without the addition of acetic acid. R may be, without limitation, $C_1\text{-}C_6$alkyl such as tert-butyl or isopropyl, $C_6\text{-}C_{10}$carbocycle such as phenyl, or 6- to 10-membered heterocycle. Alternatively, R may be a protecting group, such as benzyl or 2,4-dimethoxy benzyl, which may be removed from VI using hydrogenolysis or by treatment with an acid, such as TFA or HCl. Alternatively, V may contain an alkyl halide, such as the bromide shown, and reacted with the product of reductive animation (step 2) of aldehyde IV with the amine to form VI (step 3). The alkylation using halide V may be conducted in the presence of a base, such as NaH, NaOH, Hunig's base, or NaHMDS in a solvent such as THF or DMF. The halide and nitro substituted compounds VI may be reacted with alkyl, aryl, or heteroaryl alcohols, thiols, phenols, or thiophenols using a base such as $K_2CO_3$ or Hunig's base in a solvent such as THF or DMF. Nitro groups may be reduced to amino groups, using Pd or Raney Ni catalyzed hydrogenation or using Fe in the presence of $NH_5Cl$, HCl or acetic acid, and further functionalized to compounds I using the processes described in U.S. Patent Application Publication Nos. 20070232627, 20070197558 and 20070232645, and WO2008/133753, as well as those described in WO2004014313, WO2004014852, WO2006133326, WO2007070556, WO2007070600, WO2008021927, WO2008021928, WO2008021936, WO2008064218, and WO2008070447, T is —$CH_2$—N(R)—$CH_2$— or –$CH_2$—NH—$CH_2$—.

In addition, the compounds of Formula I can be directly prepared from

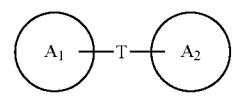

or an activated derivative thereof. For example, the compounds of the present invention can be prepared from a compound of Formula VI as shown in Scheme VII, which can be prepared through Schemes I-V by substituting chloro and/or nitro for IV and V. The halide and nitro substituted compounds VI may be reacted with alkyl, aryl, or heteroaryl alcohols, thiols, phenols, or thiophenols using a base such as $K_2CO_3$ or Hunig's base in a solvent such as THF or DMF. Nitro groups may be reduced to amino groups, using Pd or Raney Ni catalyzed hydrogenation or using Fe in the presence of $NH_4Cl$, HCl, or acetic acid, and further functionalized to compounds I using the processes described in U.S. Patent Application Publication Nos. 20070232627, 20070197558

Scheme VI

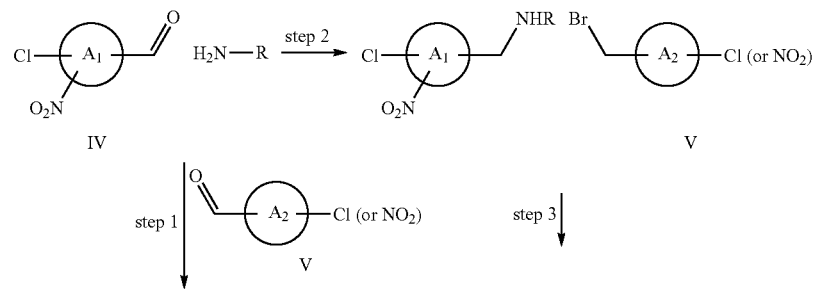

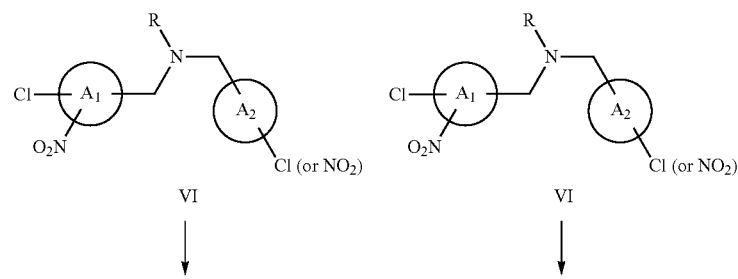

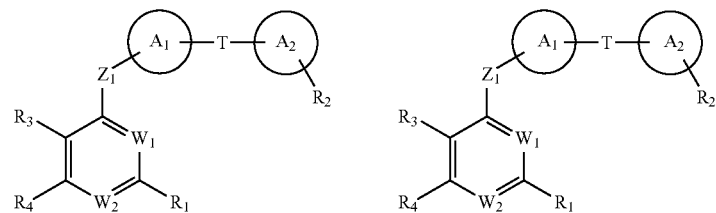

and 20070232645, and WO2008/133753, as well as those described in WO2004014313, WO2004014852, WO2006133326, WO2007070556, WO2007070600, WO2008021927, WO2008021928, WO2008021936, WO2008064218, and WO2008070447.

Scheme VII

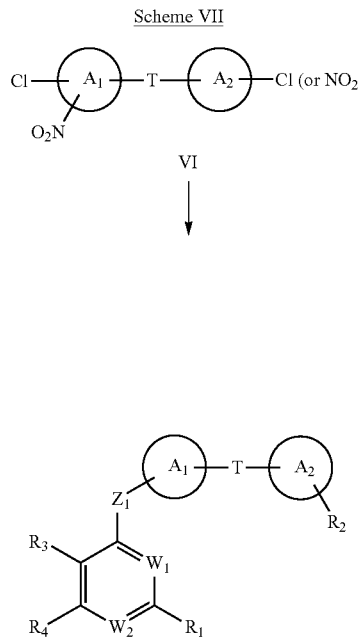

The compounds having Formulae II and III can be similarly prepared according to the above schemes, as appreciated by those skilled in the art.

If a moiety described herein (e.g., —NH₂ or —OH) is not compatible wills the synthetic methods, the moiety may be protected with a suitable protecting group that is stable to the reaction conditions used in the methods. The protecting group may be removed at a suitable point in the reaction sequence to provide a desired intermediate or target compound. Suitable protecting groups and methods for protecting or deprotecting moieties are well know in the art, examples of which can be found in Greene and Wuts, supra. Optimum reaction conditions and reaction times for each individual step may vary depending on the particular reactants employed and substituents present in the reactants used. Solvents, temperatures and other reaction conditions may be readily selected by one of ordinary skill in the art based on the present invention.

It should be understood that the above-described embodiments and schemes and the following examples are given by way of illustration, not limitation. Various changes and modifications within the scope of the present invention will become apparent to those skilled in the art from the present description.

Example 1

S)-4-(4-aminophenylthio)-3-(7-isopropylpyrido[2,3-d]pyrimidin-4-ylamino)-N-(4-(2-(2-(2-phenylacetyl)pyrrolidin-2-yl)-1H-imidazol-4-yl)phenyl)benzamide

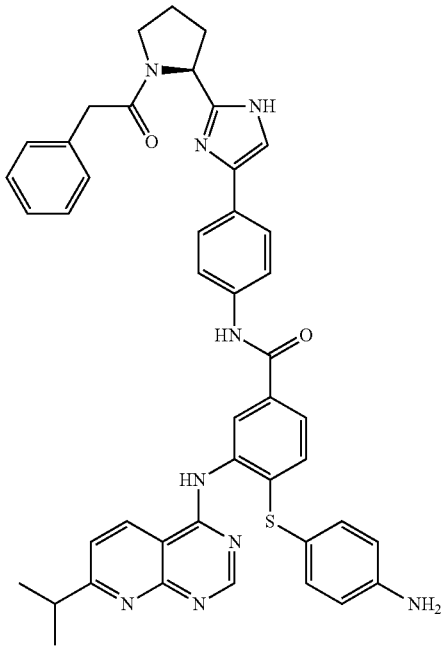 [SMILES: CC(C)c1ccc2c(Nc3cc(C(=O)Nc4ccc(-c5c[nH]c([C@@H]6CCCN6C(=O)Cc6ccccc6)n5)cc4)ccc3Sc3ccc(N)cc3)ncnc2n1]

Example 1A 4-(4-Amino-phenylsulfanyl)-3-nitro-benzoic acid methyl ester

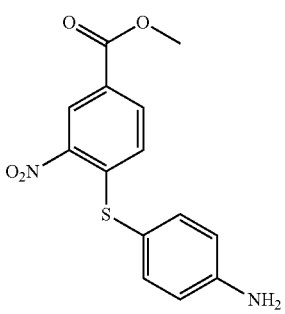 [SMILES: COC(=O)c1ccc(Sc2ccc(N)cc2)c([N+](=O)[O-])c1]

A mixture of 4-chloro-3-nitrobenzoic acid methyl ester (15.0 g, 68 mmol), 4-aminothiophenol (8.8 g, 68 mmol) and K₂CO₃ (11.8 g, 85 mmol) in DMF (150 mL) was heated at 90° C. for 1.5 hours, cooled to room temperature, and then poured into H₂O (450 mL) under stirring. The aqueous mixture was extracted with ethyl acetate (400 mL). The extract was washed with H₂O (3 times) and brine, dried over MgSO₄, and evaporated to give the crude product as orange crystal. The crude product was suspended in 150 mL of i-Pr₂O and stirred at room temperature for 1 hour. The crystal was collected by filtration, washed with i-Pr₂O and dried at 60° C. for 3 days under reduced pressure gave purified title compound as orange crystal (18.6 g, 90% yield).

Example 1B 4-(4-tert-Butoxycarbonylamino-phenylsulfanyl)-3-nitro-benzoic acid methyl ester

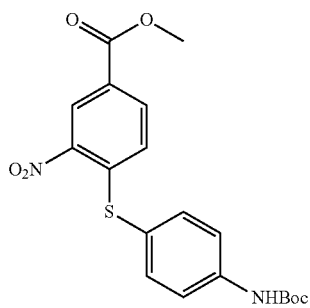

A solution of the product from Example 1A (18.5 g, 61 mmol) and di-tert-butyl dicarbonate (26.8 g, 122 mmol) in p-dioxane (280 mL) was heated at 90° C. for 3 hours. An additional di-tert-butyl dicarbonate (26.8 g, 122 mmol) was added and the mixture was heated at 90° C. for 3 hours. A second additional di-tert-butyl dicarbonate (13.4 g, 61 mmol) was added and the mixture was heated at 90° C. for 4 hours. The reaction mixture was cooled to room temperature, and then evaporated. The residue was diluted with i-$Pr_2O$ (250 mL) and the mixture was stirred at room temperature for 1 hour. The resulting crystal was collected by filtration, washed with i-$Pr_2O$ and dried at 60° C. overnight under reduced pressure gave the title compound as yellow crystal (22.8 g, 93% yield).

Example 1C

3-Amino-4-(4-tert-butoxycarbonylamino-phenylsulfanyl)-benzoic acid methyl ester

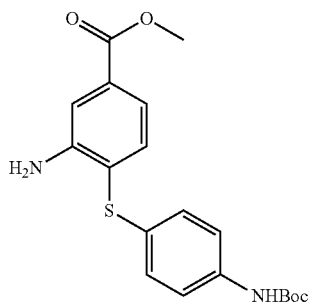 [SMILES: COC(=O)c1ccc(Sc2ccc(NC(=O)OC(C)(C)C)cc2)c([N+](=O)[O-])c1]

A suspension of the product from Example 1B (22.8 g, 56 mmol), Fe powder (16.4 g, 282 mmol) and $NH_4Cl$ (15.1 g, 282 mmol) in aqueous EtOH [prepared from EtOH (228 mL) and $H_2O$ (228 mL)] was gradually heated to reflux and gently refluxed for 2 hours. The reaction mixture was cooled to room temperature and filtered through celite pad. The filtrate was evaporated. The aqueous residue was portioned between Ethyl acetate and H2O, made basic to pH 9 with $K_2CO_3$, and then filtered through celite pad. The organic layer was separated, washed with H2O and brine, dried over $MgSO_4$ and evaporated. The oily residue was crystallized in the treatment with i-$Pr_2O$ (200 mL) and stirred at room temperature for 30 minutes. The resulting crystal was collected by filtration, washed with i-$Pr_2O$ and dried at 60° C. overnight under reduced pressure gave the title compound as colorless crystal (13.9 g, 66% yield).

Example 1D 4-(4-tert-Butoxycarbonylamino-phenylsulfanyl)-3-(7-isopropyl-pyrido[2,3-d]pyrimidin-4-ylamino)-benzoic acid methyl ester

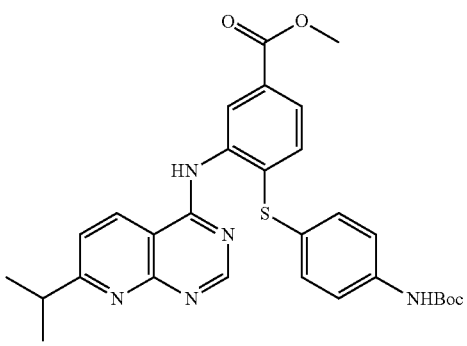 [SMILES: COC(=O)c1ccc(Sc2ccc(NC(=O)OC(C)(C)C)cc2)c(Nc2ncnc3nc(C(C)C)ccc23)c1]

A suspension of N'-(3-cyano-6-isopropyl-pyridin-2-yl)-N,N-dimethyl-formamidine (2.00 g, 9.3 mmol) and the product from Example 1C (3.46 g, 9.3 mmol) in Acetic acid (40 mL) was heated at 120° C. for 20 minutes under $N_2$. After cooling to room temperature, the reaction mixture was portioned between ethyl acetate (150 mL) and $H_2$ (200 mL), and then made basic to pH 9 with $K_2CO_3$ under stirring. The organic layer was separated, washed with 10% $NaHCO_3$, $H_2O$ and brine, dried over $MgSO_4$, and evaporated to give a pale brown oil. The oily residue was separated by silica gel column chromatography (ethyl acetate/n-hexane=5/1) gave yellow crystal. Further purification by washing with cold ethyl acetate (15 mL) gave the title compound as slightly yellow crystal (3.27 g, 65% yield).

Example 1E 4-(4-tert-Butoxycarbonylamino-phenylsulfanyl)-3-(7-isopropyl-pyrido[2,3-2]pyrimidin-4-ylamino)-benzoic acid

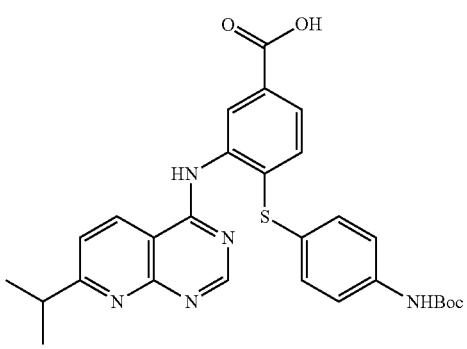 [SMILES: CC(C)c1ccc2c(Nc3cc(C(=O)O)ccc3Sc3ccc(NC(=O)OC(C)(C)C)cc3)ncnc2n1]

To a solution of the product from Example 1D (3.25 g, 6.0 mmol) in THF (32.5 mL) was added aqueous LiOH [prepared from LiOH monohydrate (1.02 g, 24 mmol) and $H_2O$ (10 mL)] dropwise at room temperature. The mixture was stirred at room temperature for 26 hours, and then evaporated. The aqueous mixture was diluted with 100 ml, of H$_2$O, washed with ethyl acetate (50 mL), and then carefully acidified to pH 4-5 with 10% HCl at 5° C. under stirring. The resulting solid was collected by filtration, washed with H$_2$O, and dried at 60° C. overnight under reduced pressure gave the title compound as pale yellow crystal (3.09 g, 98% yield).

Example 1F (S)-1-tert-butyl 2-(2-(4-nitrophenyl)-2-oxoethyl) pyrrolidine-1,2-dicarboxylate

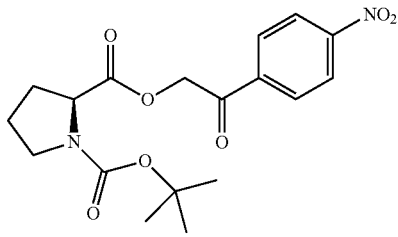 [SMILES: CC(C)(C)OC(=O)N1CCC[C@H]1C(=O)OCC(=O)c1ccc([N+](=O)[O-])cc1]

To a solution of BOC-L-Proline (0.485 g, 2.25 mmol) and 2-Bromo-4'-nitro acetophenone (0.500 g, 2.05 mmol) in acetonitrile (20 mL) was added diisopropylethylamine (0.39 mL, 2.25 mmol) dropwise at ambient temperature. After stirred for four hours, the solution was poured into brine and extracted into ethyl acetate, dried over sodium sulfate, filtered, and the filtrate was concentrated to give a crude material that was used without purification (100% yield).

Example 1G (S)-tert-butyl 2-(4-(4-nitrophenyl)-1H-imidazol-2-yl) pyrrolidine-1-carboxylate

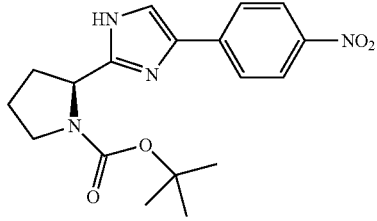 [SMILES: CC(C)(C)OC(=O)N1CCC[C@H]1c1nc(-c2ccc([N+](=O)[O-])cc2)c[nH]1]

To a solution of the Product from Example 1F (0.775 g, 2.05 mmol) in toluene (10 mL) was added ammonium acetate (3.16 g, 41.0 mmol) in one portion. The mixture was heated at 100° C. for 16 hours. The dark red solution was poured into brine, extracted into ethyl acetate, concentrated, and purified by combi-flash 12 g column, eluting with 0-30% ethyl acetate in dichloromethane to give a waxy solid (0.545 g, 74%).

Example 1H (S)-4-(4-nitrophenyl)-2-(pyrrolidin-2-yl)-1H-imidazole

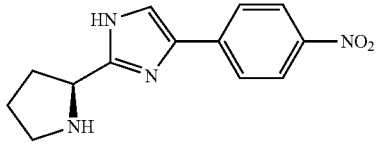 [SMILES: O=[N+]([O-])c1ccc(-c2c[nH]c([C@@H]3CCCN3)n2)cc1]

To a solution of the Product form Example 1G (0.545 g, 1.52 mmol) in dichloromethane (15 mL) was added trifluoroacetic acid (2.34 mL, 30.4 mmol) dropwise at ambient temperature. The solution was stirred for 16 hours then concentrated and azeotroped with toluene twice to give an orange waxy solid TFA salt (0.367 g, 65%).

Example 1I (S)-1-(2-(4-(4-nitrophenyl)-1H-imidazol-2-yl)pyrrolidin-1-yl)-2-phenylethanone

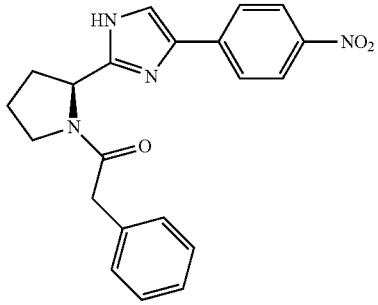

To a solution of the Product from Example 1H (0.18 g, 0.48 mmol) and HATU (0.202 g, 0.53 mmol) in DMSO (5 mL) was added diisopropylethylamine (0.253 mL, 1.45 mmol) followed by Phenyl acetic acid (0.066 mL, 0.53 mmol). The solution was stirred for 16 hours, then diluted with water and the product was filtered off and purified by combi-flash 12 g column, eluting with 0-5% methanol in dichloromethane to give a solid (0.137 g, 75%).

Example 1J (S)-1-(2-(4-(4-aminophenyl)-1H-imidazol-2-yl)pyrrolidin-1-yl)-2-phenylethanone

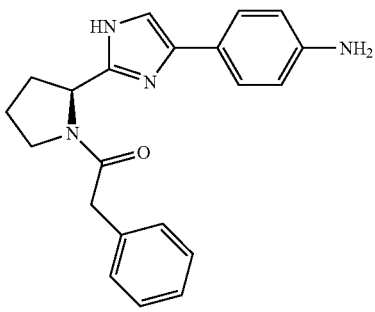 [SMILES: O=C(Cc1ccccc1)N1CCC[C@H]1c1nc(-c2ccc([N+](=O)[O-])cc2)c[nH]1]

To a solution of the Product from Example 1I (0.137 g, 0.36 mmol) in a mixture of water (0.75 mL), methanol (1.5 mL) and tetrahydrofuran (1.5 mL) was added iron (0.102 g, 1.82 mmol) and ammonium chloride (0.030 g, 0.54 mmol) and the resulting mixture was heated with vigorous stirred at 75° C. for one hour. The warm reaction mixture was filtered through celite and rinsed well with methanol and tetrahydrofuran. The filtrate was concentrated and partitioned between 10% NaHCO3 solution and ethyl acetate. The organic layer was dried over sodium sulfate, filtered, and concentrated to give a waxy solid that was used without purification (97%).

Example 1K (S)-tert-butyl-4-(2-(7-isopropylpyrido[2,3-d]pyrimidin-4-ylamino)-4-(4-(2-(1-(2-phenylacetyl)pyrrolidin-2-yl)-1H-imidazol-4-yl)phenylcarbamoyl)phenylthio)phenylcarbamate

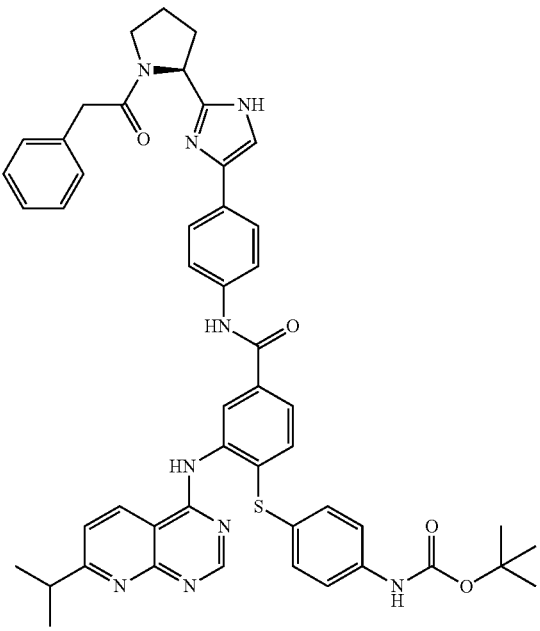 [SMILES: CC(C)c1ccc2c(Nc3cc(C(=O)Nc4ccc(-c5c[nH]c([C@@H]6CCCN6C(=O)Cc6ccccc6)n5)cc4)ccc3Sc3ccc(NC(=O)OC(C)(C)C)cc3)ncnc2n1]

To a solution of the Product from Example 1E (0.16 g, 0.30 mmol) and HATU (0.12 g, 0.316 mmol) in DMSO (5 mL) was added diisopropylethylamine (0.184 mL, 1.05 mmol) followed by the Product from Example 1J (0.115 g, 0.33 mmol). The solution was stirred at ambient temperature for 18 hours, then diluted with water and the crude product was filtered off an purified by combi-flash 12 g column, eluting with 0-10% Methanol in dichloromethane to give a solid (0.092 g, 36%).

Example 1L (S)-4-(4-aminophenylthio)-3-(7-isopropylpyrido[2,3-2]pyrimidin-4-ylamino)-N-(4-(2-(1-(2-phenylacetyl)pyrrolidin-2-yl)-1H-imidazol-4-yl)phenyl)benzamide

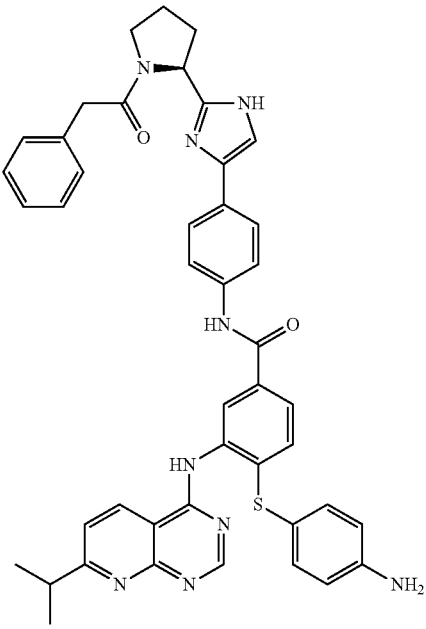 [SMILES: CC(C)c1ccc2c(Nc3cc(C(=O)Nc4ccc(-c5c[nH]c([C@@H]6CCCN6C(=O)Cc6ccccc6)n5)cc4)ccc3Sc3ccc(N)cc3)ncnc2n1]

To a solution of the Product of Example 1K (0.092 g 0.11 mmol) in tetrahydrofuran (1 mL) was added 4 M HCl in dioxane (1 mL, 4.2 mmol) at ambient temperature. After stirred for four hours, the solid HCl salt of the product was filtered off and taken up in a small amount of methanol and added to a NaHCO3 solution. Use free amine was extracted into ethyl acetate, concentrated and purified by combi-flash 12 g column, eluting with 0-10% Methanol in dichloromethane to give a yellow solid (0.03 g, 43%). 1H NMR (400 MHz, Solvent) d ppm 1.36 (d, J=7.02 Hz, 6H) 1.89-2.36 (m, 4H) 3.24 (dd, J=13.89, 6.87 Hz, 1H) 3.50-3.81 (m, 4H) 5.09-5.20 (m, 1H) 6.66 (d, J=8.54 Hz, 2H) 6.98-7.10 (m, 2H) 7.12-7.35 (m, 7H) 7.55 (d, J=8.54 Hz, 1H) 7.66-7.79 (m, 5H) 7.96 (s, 1H) 8.49 (s, 1H) 8.76 (d, J=8.24 Hz, 1H)

Example 2

4-(4-aminophenylthio)-N-(4-(2-((S)-1-((R)-2-(dimethylamino)-2-phenylacetyl)pyrrolidin-2-yl)-1H-imidazol-4-yl)phenyl-3-(7-isopropylpyrido[2,3-d]pyrimidin-4-ylamino)benzamide

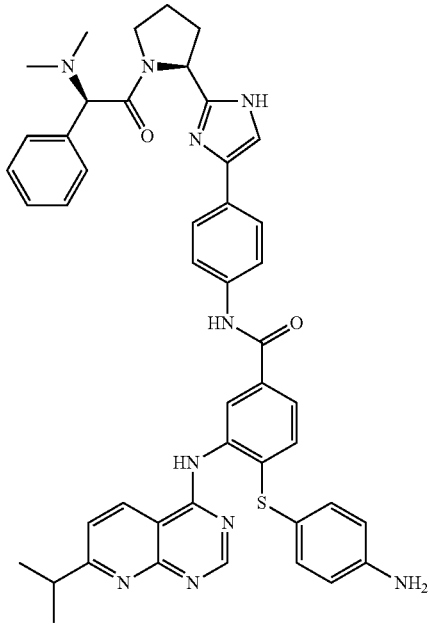 [SMILES: CC(C)c1ccc2c(Nc3cc(C(=O)Nc4ccc(-c5c[nH]c([C@@H]6CCCN6C(=O)[C@@H](c6ccccc6)N(C)C)n5)cc4)ccc3Sc3ccc(N)cc3)ncnc2n1]

Example 2A (R)-2-(dimethylamino)-2-phenylacetic acid

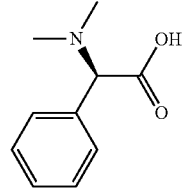

A solution of (R)-2-amino-2-phenylacetic acid (1.0 g, 6.62 mmol) and 37% aqueous formaldehyde (3.22 mL, 39.7 mmol) in methanol (22 mL) was treated with 20% Palladium on Carbon (0.35 g, 0.66 mmol) under a hydrogen atmosphere for 5 hours. After purging with nitrogen, then solution was filtered and concentrated. The residue was taken up in a small amount of methanol and ether was added. The resulting solid was filtered and dried to give a white solid.

Example 2B (R)-2-(dimethylamino)-1-((S)-2-(4-(4-nitrophenyl)-1H-imidazol-2-yl)pyrrolidin-1-yl-2-phenylethanone

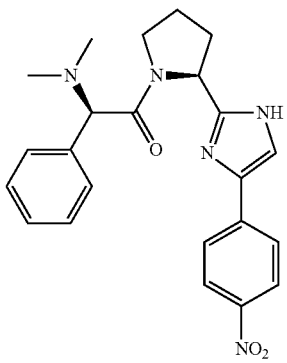 [SMILES: CN(C)[C@@H](C(=O)N1CCC[C@H]1c1nc(-c2ccc([N+](=O)[O-])cc2)c[nH]1)c1ccccc1]

The Product of Example 1H (0.185 g, 0.49 mmol) and the Product of Example 2B (0.098 g, 0.54 mmol) was processed in the same manner as in Example 1L.

Example 2C (R)-1-((S)-2-(4-(4-aminophenyl)-1H-imidazol-2-yl)pyrrolidin-1-yl)-2-(dimethylamino)-2-phenylethanone

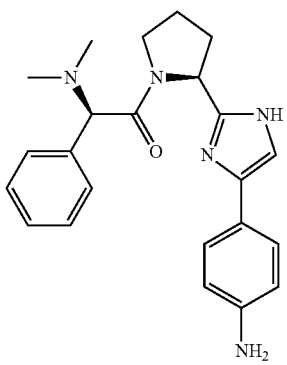 [SMILES: CN(C)[C@@H](C(=O)N1CCC[C@H]1c1nc(-c2ccc(N)cc2)c[nH]1)c1ccccc1]

The Product of Example 2B (0.21 g, 0.50 mmol) was processed in the same manner as in Example 1J to give a waxy solid (0.085 g, 44%).

Example 2D tert-butyl 4-(4-(4-(2-((S)-1-((R)-2-(dimethylamino)-2-phenylacetyl)pyrrolidin-2-yl-1H-imidazol-4-yl)phenylcarbamoyl-2-(7-isopropylpyrido[2,3-d]pyrimidin-4-ylamino)phenylthio)phenylcarbamate

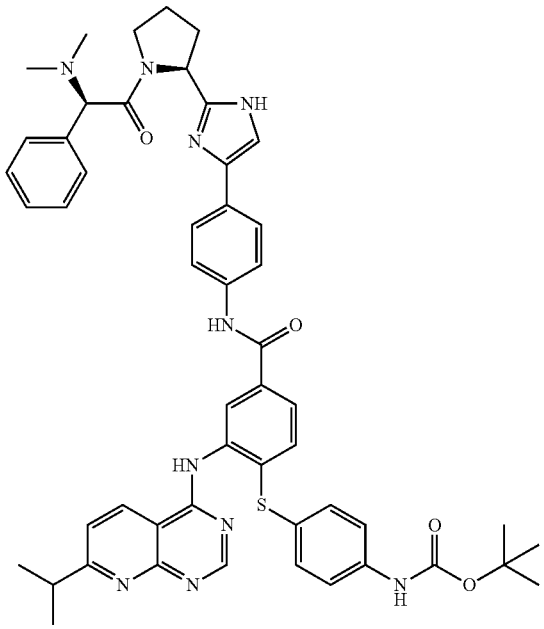 [SMILES: CC(C)c1ccc2c(Nc3cc(C(=O)Nc4ccc(-c5c[nH]c([C@@H]6CCCN6C(=O)[C@@H](c6ccccc6)N(C)C)n5)cc4)ccc3Sc3ccc(NC(=O)OC(C)(C)C)cc3)ncnc2n1]

A solution of the Product of Example 2C (0.081 g, 0.21 mmol) and the product from Example 1E (0.10 g, 0.188 mmol) was processed in the same manner as in Example 1K to give a sold (0.094 g, 55%).

Example 2E 4-(4-aminophenylthio)-N-(4-(2-((S)-1-((R)-2-(dimethylamino)-2-phenylacetyl)pyrrolidin-2-yl)-1H-imidazol-4-yl)phenyl-3-(7-isopropylpyrido[2,3-2]pyrimidin-4-ylamino)benzamide

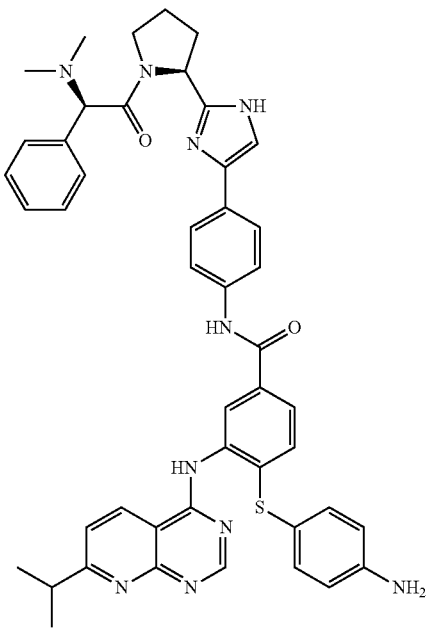 [SMILES: CC(C)c1ccc2c(Nc3cc(C(=O)Nc4ccc(-c5c[nH]c([C@@H]6CCCN6C(=O)[C@@H](c6ccccc6)N(C)C)n5)cc4)ccc3Sc3ccc(N)cc3)ncnc2n1]

The Product of Example 2D (0.094 g, 0.10 mmol) was processed in the same manner as in Example 1L to give a yellow solid (0.016 g, 19%). 1H NMR (400 MHz, Solvent) d ppm 1.36 (d, J=6.71 Hz, 6H) 1.80-2.12 (m, 4H) 2.17 (s, 6H) 3.19-3.26 (m, 1H) 3.38 (s, 1H) 3.88 (s, 1H) 4.25 (s, 1H) 5.06 (s, 1H) 6.66 (d, J=8.54 Hz, 2H) 7.02 (d, J=6.10 Hz, 1H) 7.15 (d, J=8.54 Hz, 2H) 7.23-7.50 (m, 5H) 7.55 (d, J=7.63 Hz, 1H) 7.62-7.80 (m, 5H) 7.99 (s, 1H) 8.56 (s, 1H) 8.77 (d, J=7.02 Hz, 1H)

Example 3

(S)-benzyl-2-(4-(4-(4-aminophenylthio-3-(7-isopropylpyrido[2,3-3]pyrimidin-4-ylamino)benzamido)phenylcarbamoyl)pyrrolidine-1-carboxylate

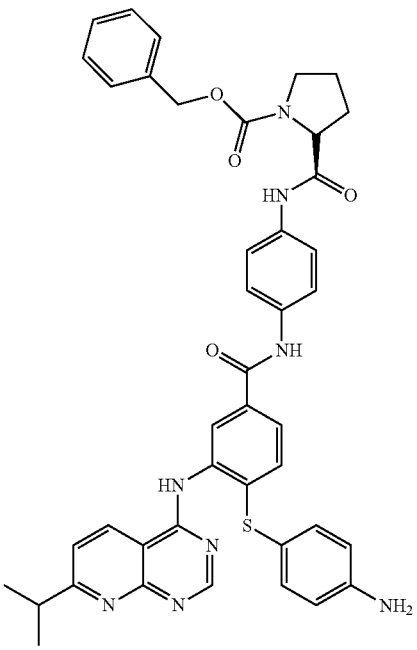

Example 3A (S)-benzyl 2-(4-(tert-butoxycarbonylamino)phenylcarbamoyl)pyrrolidine-1carboxylate

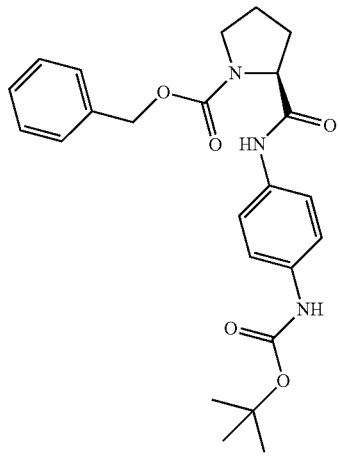 [SMILES: CC(C)(C)OC(=O)Nc1ccc(NC(=O)[C@@H]2CCCN2C(=O)OCc2ccccc2)cc1]

To a solution of Carbobenzyloxy-L-proline (0.20 g, 0.80 mmol) and HATU (0.32 g, 0.84 mmol) in DMSO (6 mL) was added diisopropylethylamine (0.42 mL, 2.41 mmol) followed by tert-buty-4-aminophenylcarbamate (0.715 g, 082 mmol). The solution was stirred at ambient temperature for two hours, then diluted with water and the solid product was filtered off and purified by combi-flash 12 g column, eluting with 0-20% ethyl acetate in dichloromethane to give a sold (0.245 g, 70%).

Example 3B (S)-benzyl 2-(4-aminophenylcarbamoyl)pyrrolidine-1-carboxylate

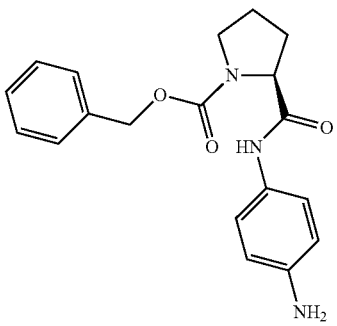 [SMILES: Nc1ccc(NC(=O)[C@@H]2CCCN2C(=O)OCc2ccccc2)cc1]

To a solution of the Product from Example 3A (0.245 g, 0.56 mmol) in dioxane (5 mL) was added 4M HCl dioxane (2.8 mL, 11.2 mol) and the mixture was stirred at ambient temperature for 17 hours. The mixture was concentrated and azeotroped with toluene to five a tan solid (0.18 g, 86%).

Example 3C (S)-benzyl 2-(4-(4-(4-(tert-butoxycarbonylamino)phenylthio)-3-(7-isoproplpyrido[2,3-d]pyrimidin-4-ylamino)benzamido)phenylcarbamoyl)pyrrolidine-1-carboxylate

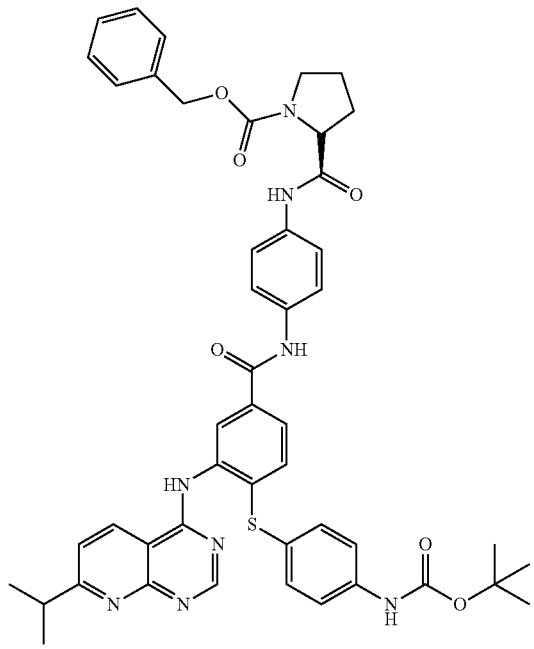

The product from Example 1E (0.15 g, 0.28 mmol) and the Product from Example 3B (0.134 g, 0.395 mmol) were processed in the same manner as Example 1K to give a solid (0.155 g, 64%).

Example 3D (S)-benzyl 2-(4-(4-(4-aminophenylthio)-3-(7-isopropylpyrido[2,3-d]pyrimidin-4-ylamino)benzamido)phenylcarbamoyl)pyrrolidine-1-carboxylate

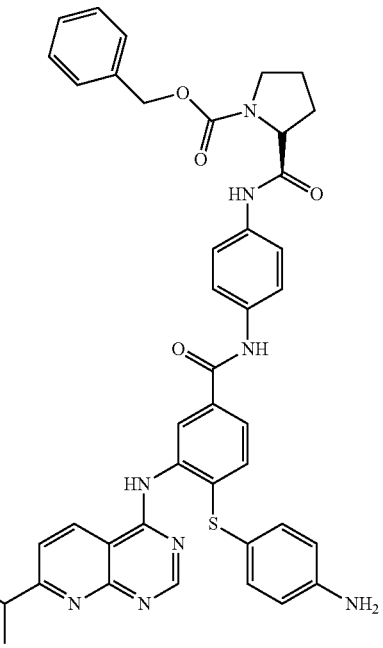

The product of Example 3C (0.094 g, 0.10 mmol) was processed in the same manner as in Example 1L to give a yellow solid (0.045 g, 33%). 1H NMR (300 MHz, DMSO-D6) d ppm 1.34 (d, J=6.62 Hz, 6H) 1.81-2.00 (m, 3H) 2.16-2.31 (m, 1H) 3.15-3.27 (m, 1 h) 3.41-3.56 (m, 2H) 4.29-4.40 (m, 1H) 4.92-5.14 (m, 2H) 5.59 (s, 2H) 6.64 (d, J=8.46 Hz, 2H) 6.87 (d, J=8.82 Hz, 1H) 7.15 (d, J=8.46 Hz, 2H) 7.18-7.27 (m, 1H) 7.34-7.42 (m, 2H) 7.54 (J=8.09 Hz, 2H) 7.62-7.72 (m, 3H) 7.78 (d, J=7.35 Hz, 1H) 7.95 (s, 1H) 8.59 (z, 1H) 8.89 (d, J=7.72 Hz, 1H) 10.01 (d, J=5.52 Hz, 1H) 10.14 (d, J=5.88 Hz, 2H)

Example 4

(S)—N-(4-(4-(4-aminophenylthio)-3-(7-isopropylpyrido[2,3-3]pyrimidin-4-ylamino)benzamido)phenyl)pyrrolidine-2-carboxamide

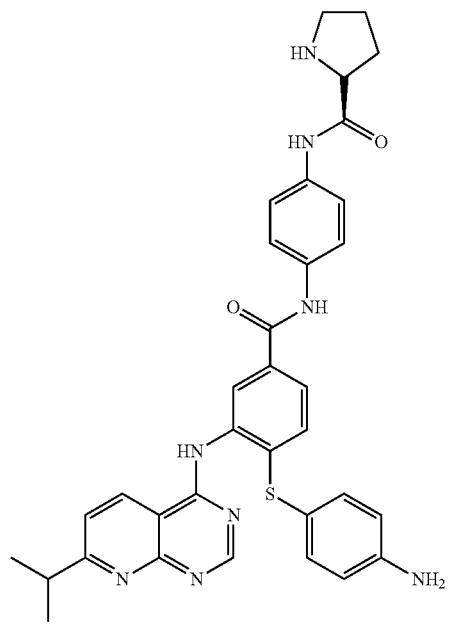

The product of Example 3C (0.094 g, 0.10 mmol) was processed in the same manner as in Example 1L to give this product as a yellow solid (0.014 g, 12%). 1H NMR (300 MHz, DMSO-D6) d ppm 1.34 (d, J=6.99 Hz, 6H) 1.58-1.70 (m, 2H) 1.70-1.85 (m, 1H) 1.95-2.12 (m, 1H) 2.88 (t, J=6.62 Hz, 2H) 3.13-3.26 (m, 1H) 3.66 (dd, J=8.64, 533 Hz, 1H) 5.519 (s, 2H) 6.63 (D, J=8.46 Hz, 2H) 6.86 (d, J=8.46 Hz, 1H) 7.14 (d, J=8.46 Hz, 2H) 7.63 (q, J=8.95 Hz, 5H) 7.77 (d, J=9.19 Hz, 1H) 7.94 (s, 1H) 8.58 (s, 1H) 8.88 (d, J=6.99 Hz, 1H) 9.90 (s, 1H) 10.13 (d, J=10.66 Hz, 2H)

The following compounds were also prepared according to the processes described herein:

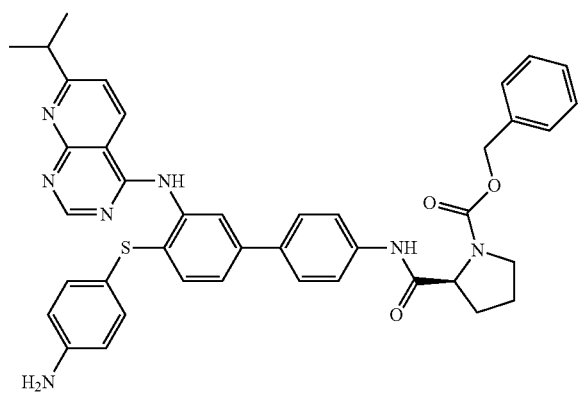 [SMILES: CC(C)c1ccc2c(Nc3cc(-c4ccc(NC(=O)[C@@H]5CCCN5C(=O)OCc5ccccc5)cc4)ccc3Sc3ccc(N)cc3)ncnc2n1]

Example 5

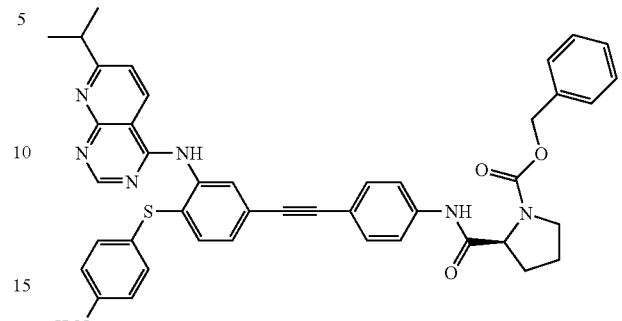

Example 6

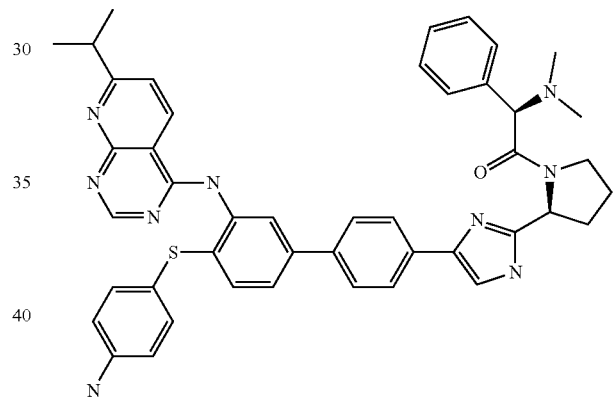

Example 7

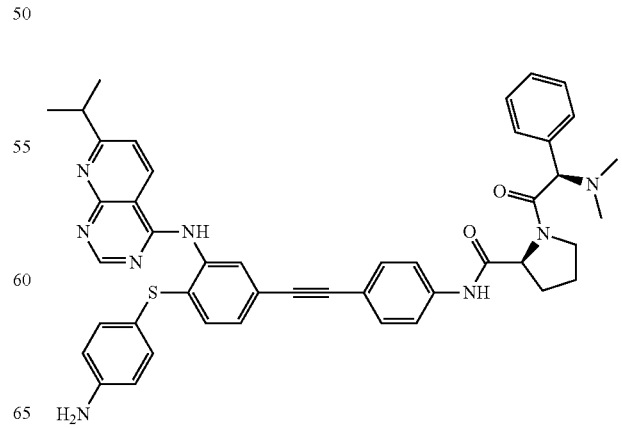

53
Example 8
54
Example 11
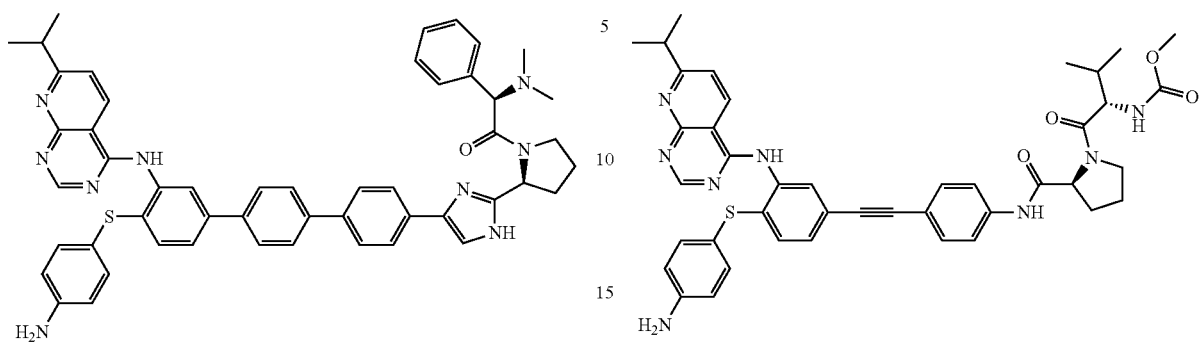
Example 9
Example 12
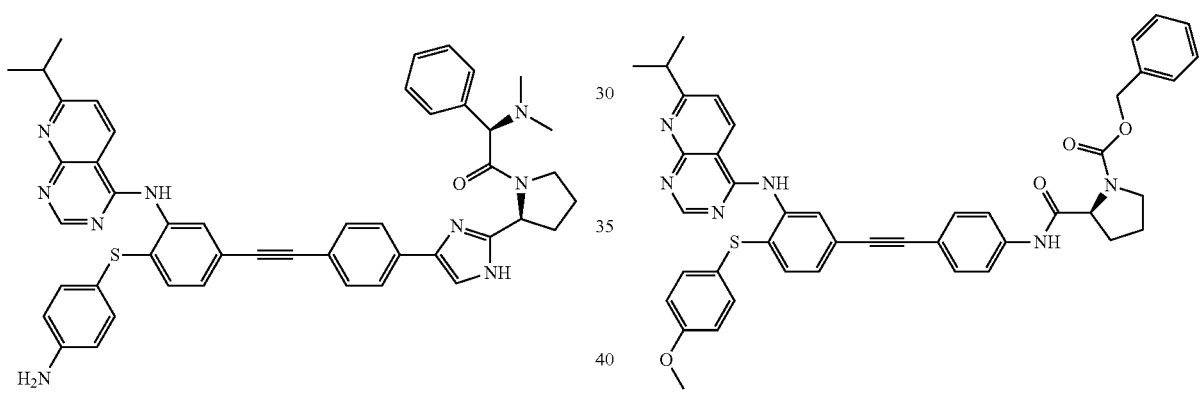
Example 10
Example 13
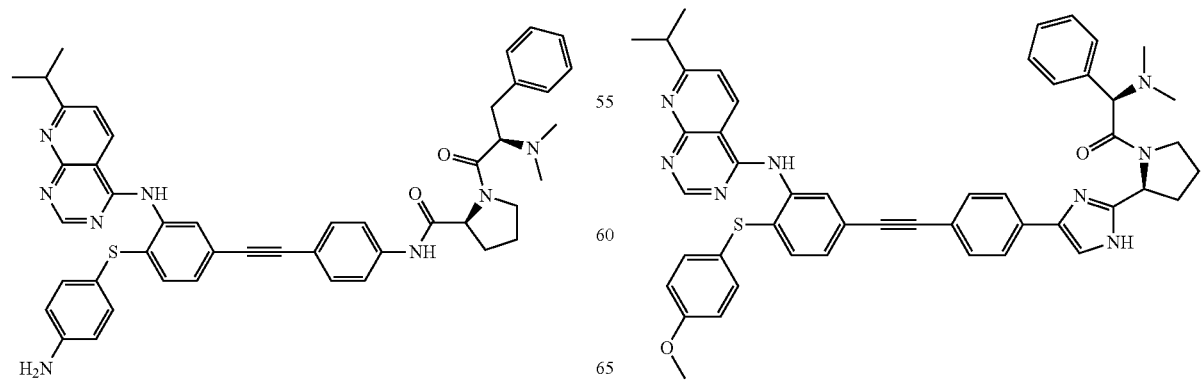

Example 14
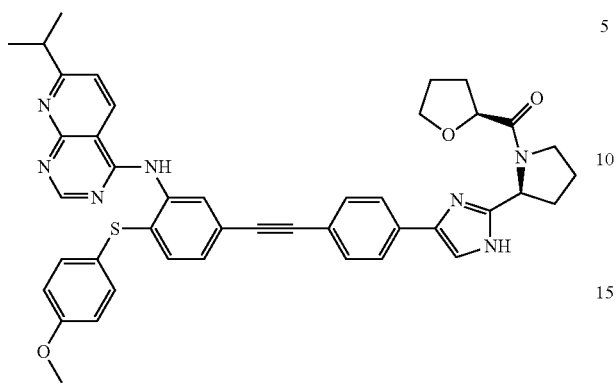
Example 15
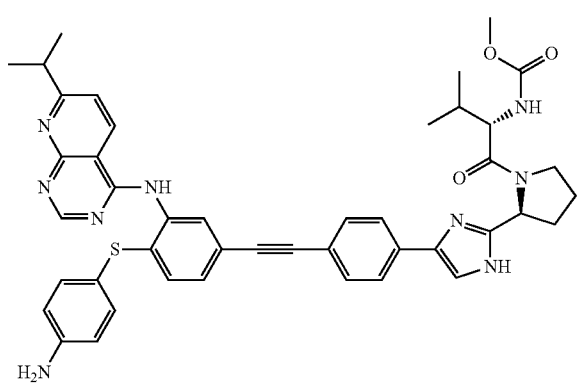 [SMILES: COC(=O)N[C@H](C(=O)N1CCC[C@H]1c1nc(-c2ccc(C#Cc3ccc(Sc4ccc(N)cc4)c(Nc4ncnc5nc(C(C)C)ccc45)c3)cc2)c[nH]1)C(C)C]
Example 16
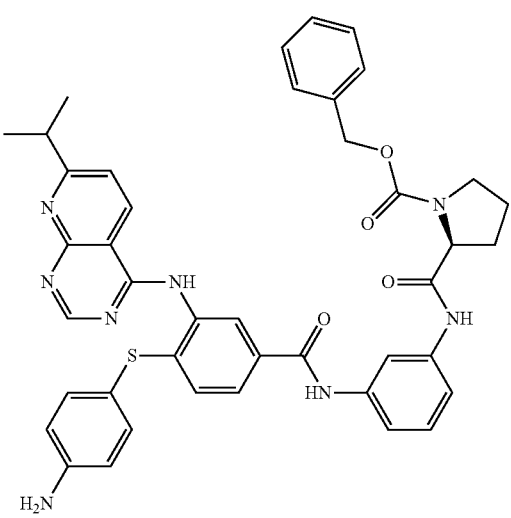 [SMILES: CC(C)c1ccc2c(Nc3cc(C(=O)Nc4cccc(NC(=O)[C@@H]5CCCN5C(=O)OCc5ccccc5)c4)ccc3Sc3ccc(N)cc3)ncnc2n1]
Example 17
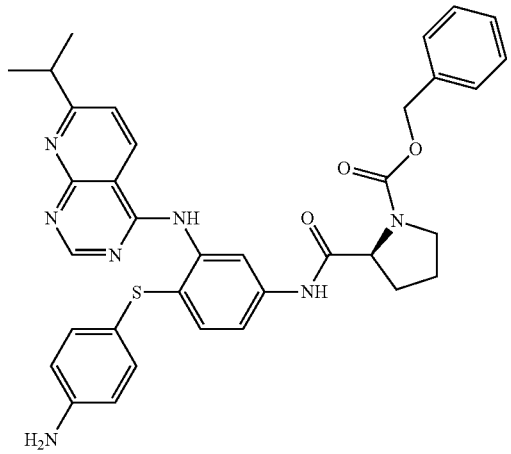 [SMILES: CC(C)c1ccc2c(Nc3cc(NC(=O)[C@@H]4CCCN4C(=O)OCc4ccccc4)ccc3Sc3ccc(N)cc3)ncnc2n1]
Example 18
The following compounds of Formula I can be similarly prepared according to the present invention,
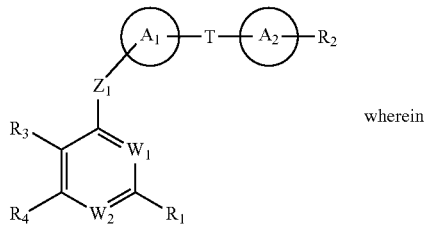
wherein
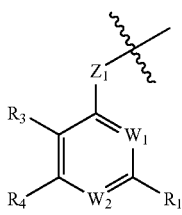
is selected from Table 1; —$X_1$—$R_7$ is selected from Tablet 2; $A_1$ and $A_2$ are selected from Table 3a and Table 3b, respectively; and T is selected from Table 4.
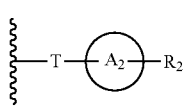
may also be selected from Table 5.

TABLE 1
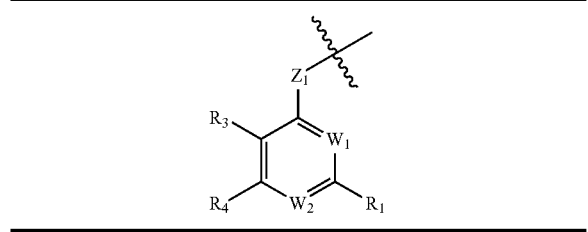
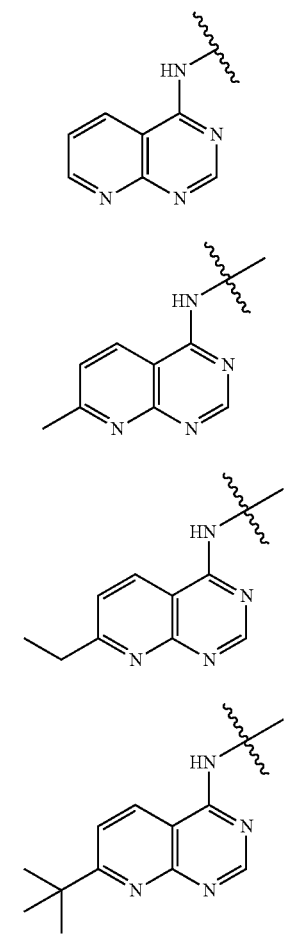
TABLE 1-continued
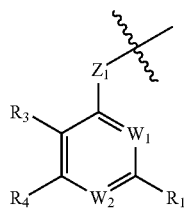
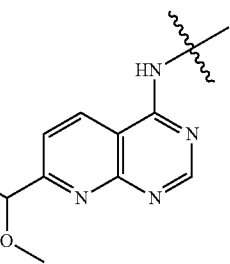
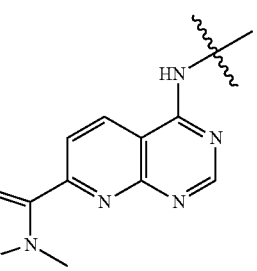
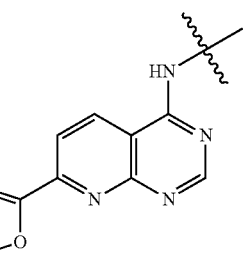
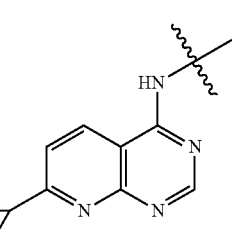
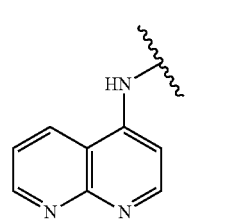

TABLE 1-continued
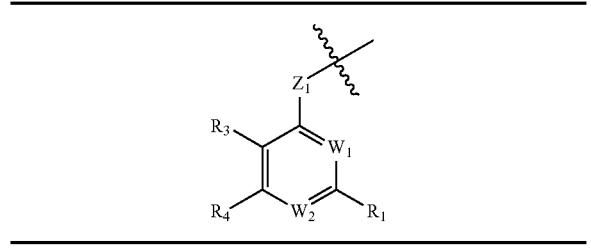
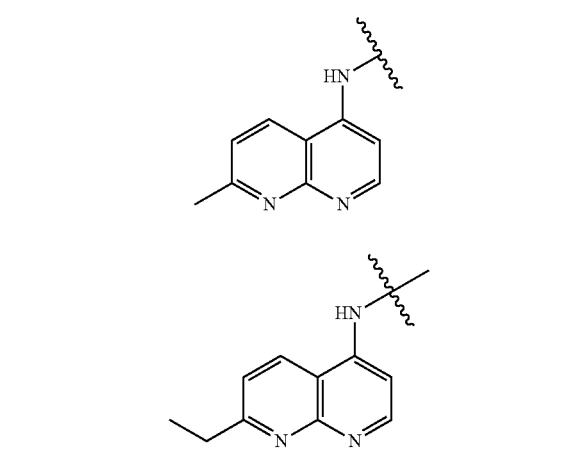
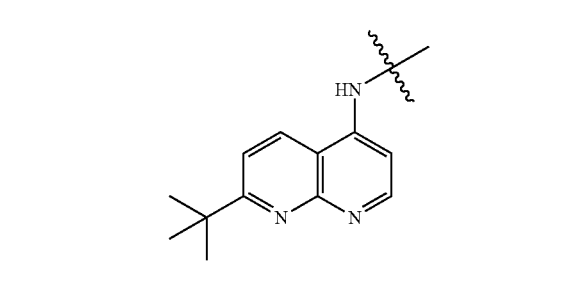 [SMILES: *Nc1ncnc2nc(C(C)(C)C)ccc12]
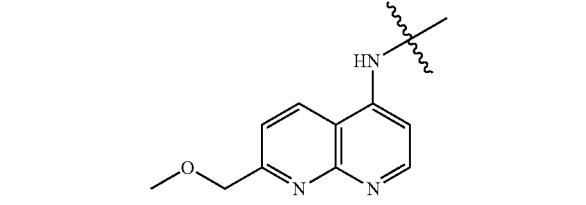 [SMILES: *Nc1ccnc2nc(COC)ccc12]
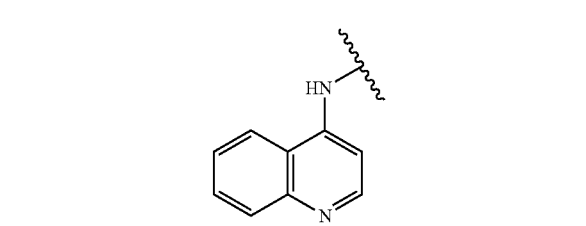 [SMILES: *Nc1ccnc2ccccc12]
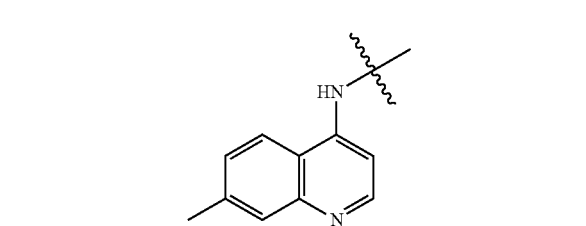 [SMILES: *Nc1ccnc2cc(C)ccc12]
TABLE 1-continued
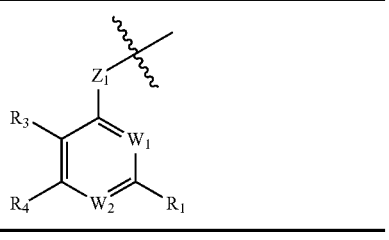
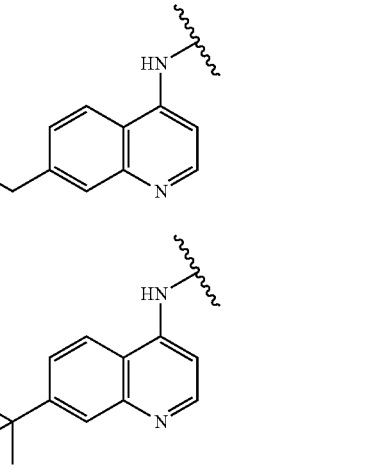
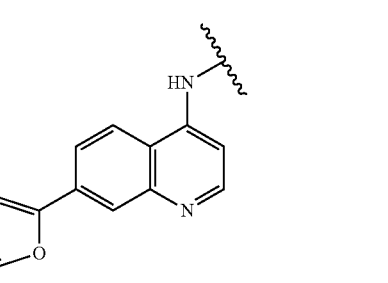
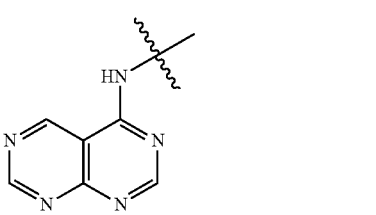 [SMILES: *Nc1ncnc2ncncc12]
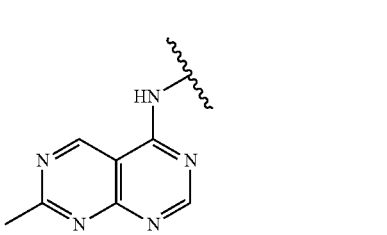 [SMILES: *Nc1ncnc2nc(C)ncc12]
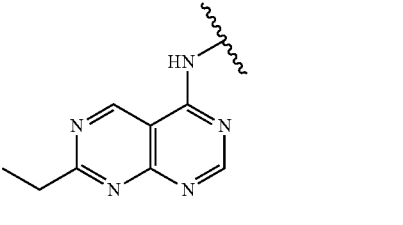 [SMILES: *Nc1ncnc2nc(CC)ncc12]

TABLE 1-continued
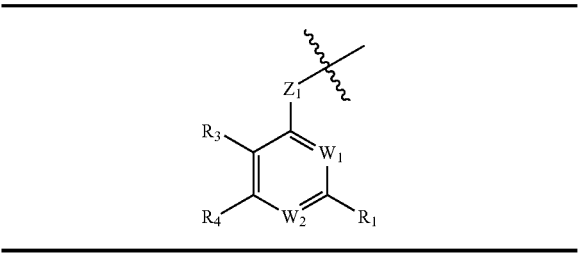
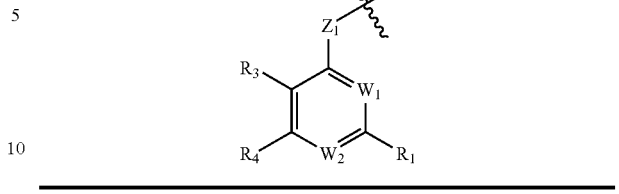
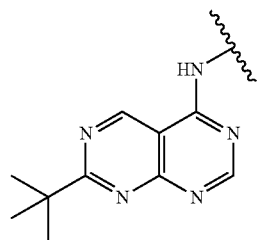 [SMILES: *Nc1ncnc2nc(C(C)(C)C)ncc12]
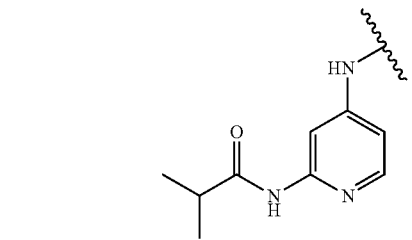
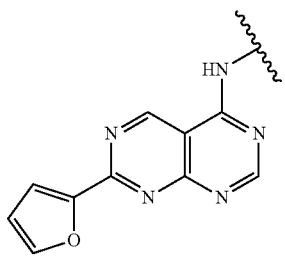 [SMILES: *Nc1ncnc2nc(-c3ccco3)ncc12]
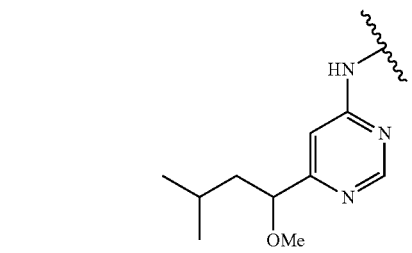
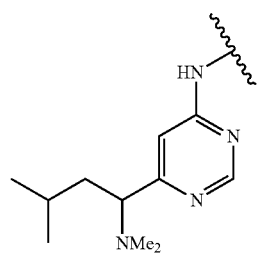 [SMILES: *Nc1ccnc(C(CC(C)C)N(C)C)c1]
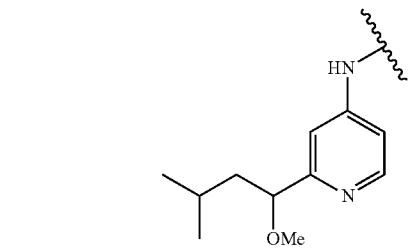 [SMILES: *Nc1ccnc(C(CC(C)C)OC)c1]
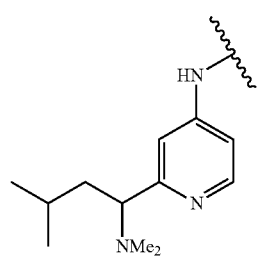
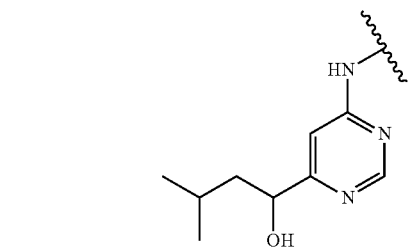 [SMILES: *Nc1cc(C(O)CC(C)C)ncn1]
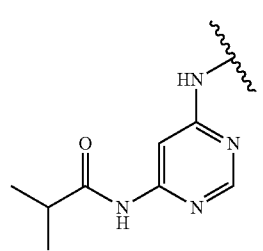
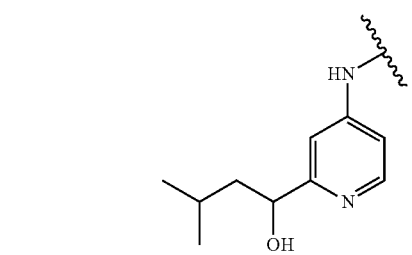 [SMILES: *Nc1ccnc(C(O)CC(C)C)c1]

TABLE 1-continued
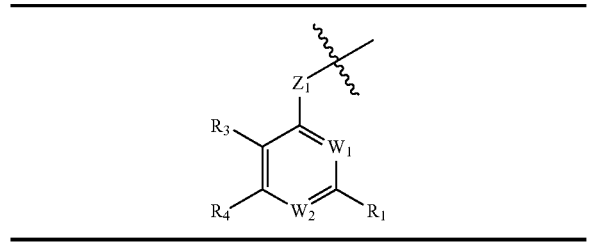
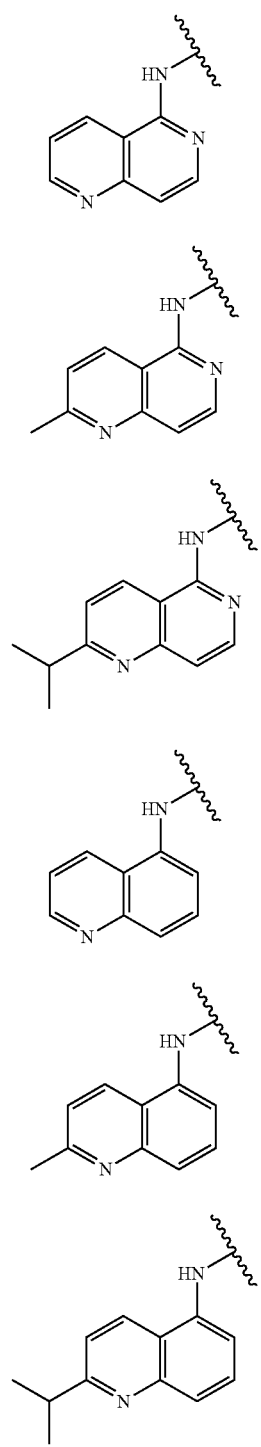
TABLE 1-continued
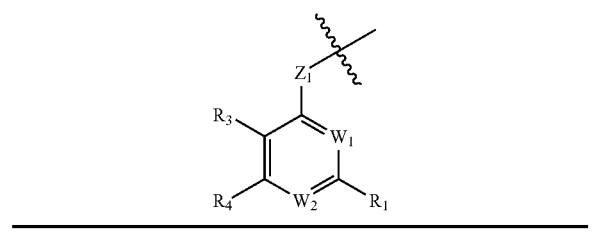
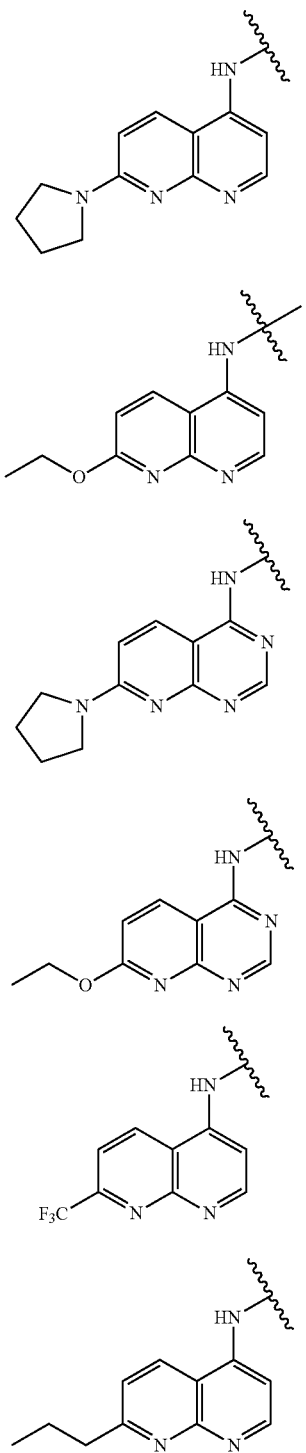

TABLE 1-continued
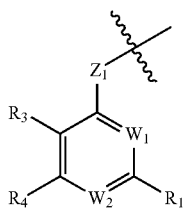
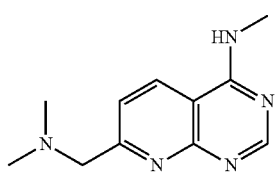
TABLE 2
—X₁—R₇
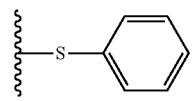
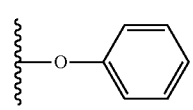 [SMILES: *Sc1ccccc1]
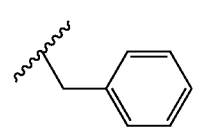 [SMILES: *Cc1ccccc1]
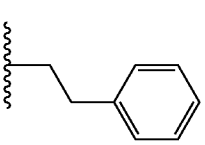 [SMILES: *CCc1ccccc1]
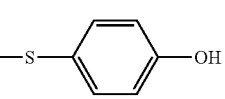
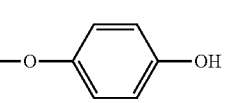
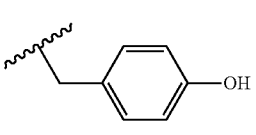 [SMILES: *Cc1ccc(O)cc1]
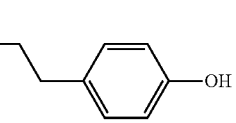
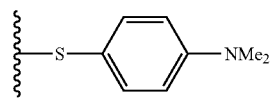
TABLE 2-continued
—X₁—R₇
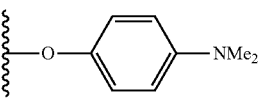
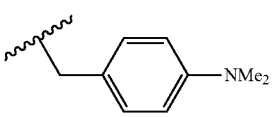 [SMILES: *Cc1ccc(N(C)C)cc1]
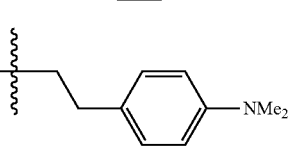
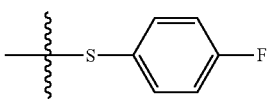
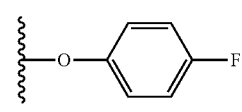
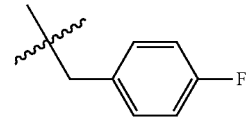 [SMILES: *Cc1ccc(F)cc1]
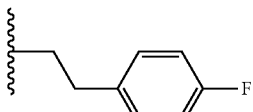
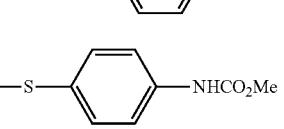
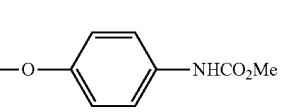
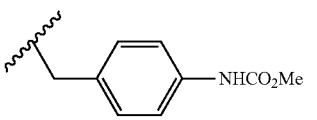

TABLE 2-continued
—X$_1$—R$_7$
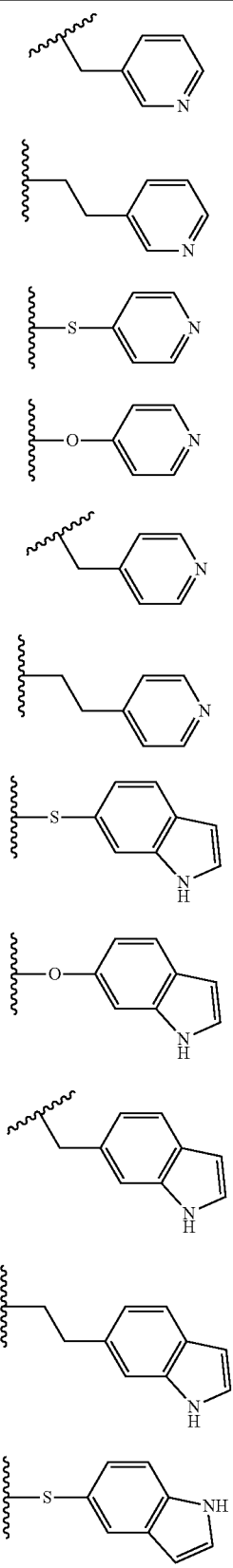
TABLE 2-continued
—X$_1$—R$_7$
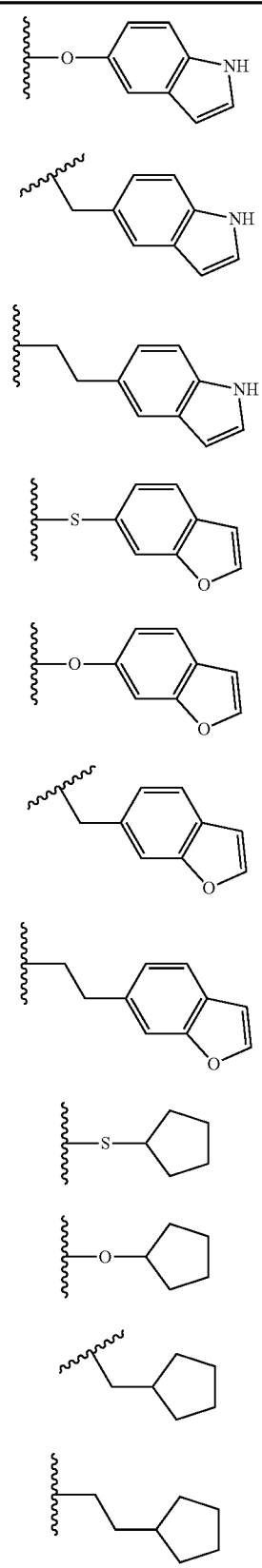

TABLE 2-continued

—X$_1$—R$_7$

TABLE 3a

A$_1$

TABLE 3a-continued

A$_1$

TABLE 3a-continued

A₁ (structures shown)

TABLE 3b

A₂ (structures shown)

TABLE 3b-continued

A₂ (structures shown)

TABLE 3b-continued
A₂
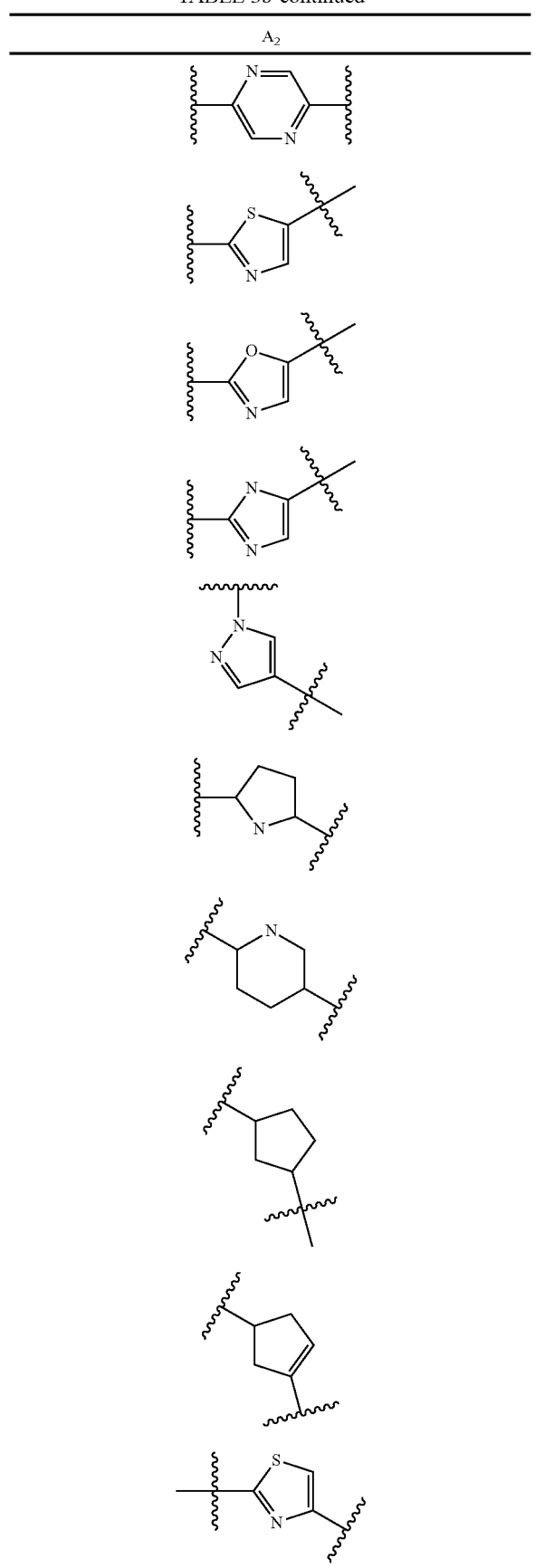
TABLE 3b-continued
A₂
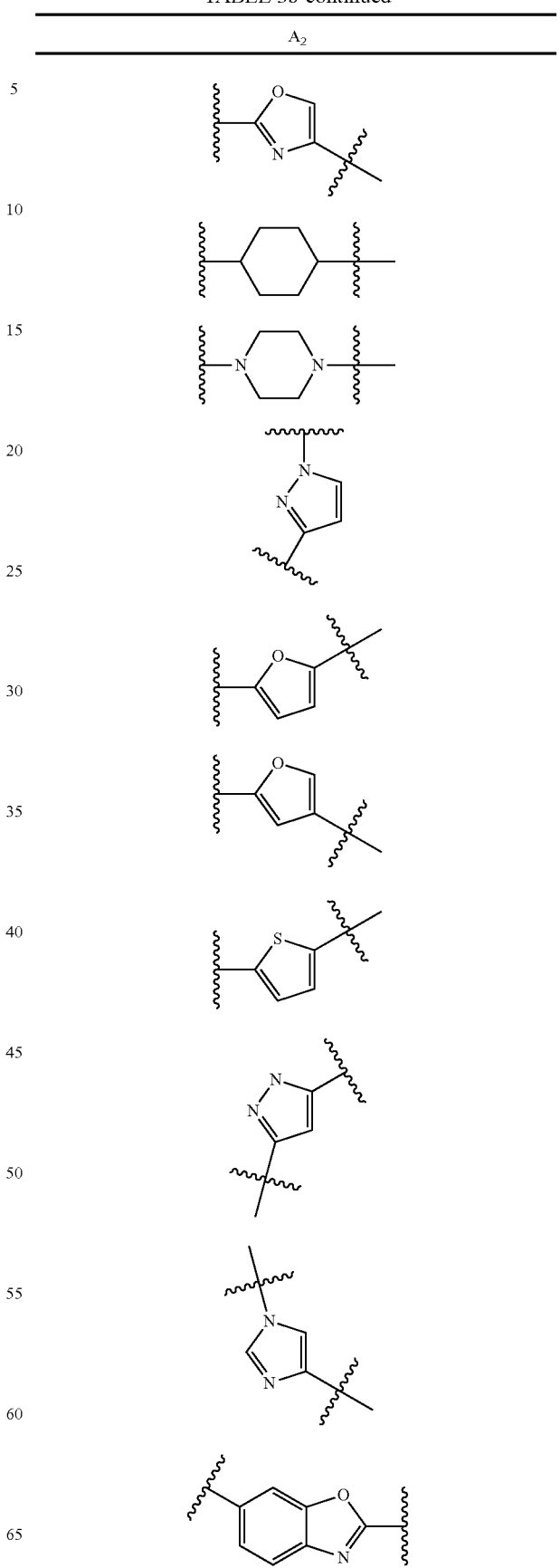

TABLE 3b-continued
A$_2$
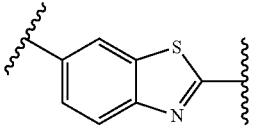 [SMILES: *c1ccc2nc(*)sc2c1]
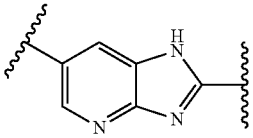 [SMILES: *c1cnc2nc(*)[nH]c2c1]
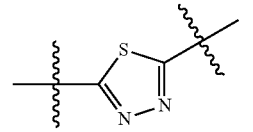 [SMILES: *c1nnc(*)s1]
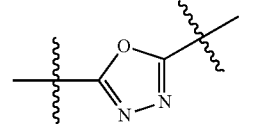
TABLE 4
—T—
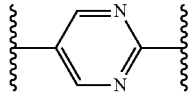 [SMILES: *c1cnc(*)nc1]
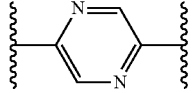
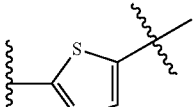
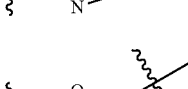
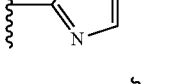
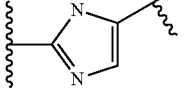
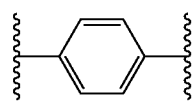
TABLE 4-continued
—T—
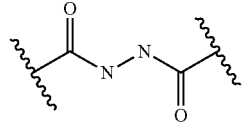 [SMILES: *C(=O)NNC(*)=O]
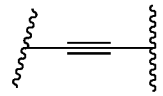 [SMILES: *C#C*]
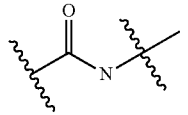 [SMILES: *NC(*)=O]
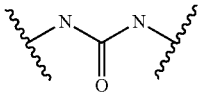 [SMILES: *NC(=O)N*]
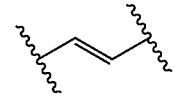 [SMILES: */C=C/*]
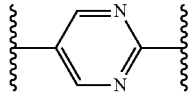 [SMILES: *c1cnc(*)nc1]

TABLE 4-continued
—T—
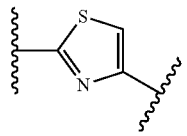 [SMILES: *c1csc(*)n1]
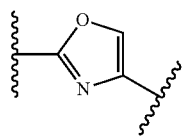 [SMILES: *c1coc(*)n1]
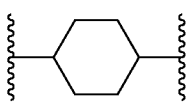
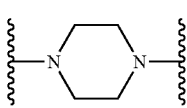
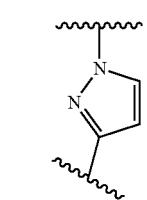
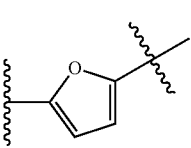 [SMILES: *c1ccc(*)o1]
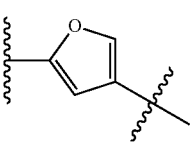 [SMILES: *c1coc(*)c1]
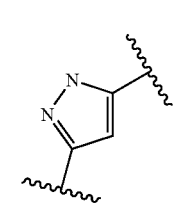 [SMILES: *c1cc(*)[nH]n1]
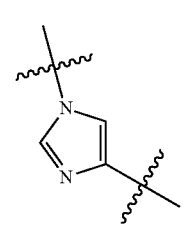 [SMILES: *c1cn(*)cn1]
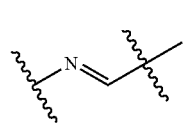 [SMILES: */C=N/*]
TABLE 4-continued
—T—
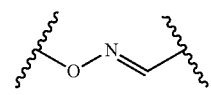 [SMILES: */C=N/O*]
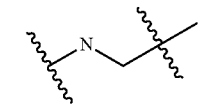
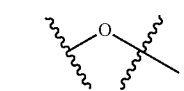
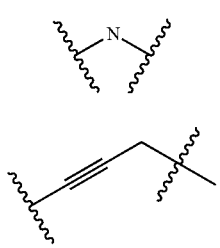
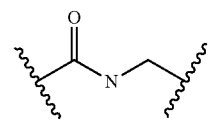 [SMILES: *CNC(*)=O]
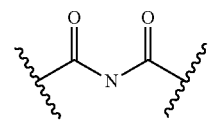 [SMILES: *C(=O)NC(*)=O]
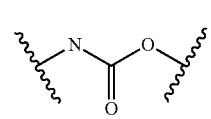 [SMILES: *NC(=O)O*]
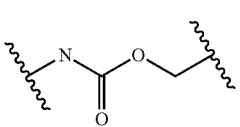 [SMILES: *COC(=O)N*]
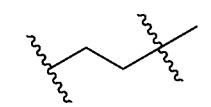 [SMILES: *CC*]
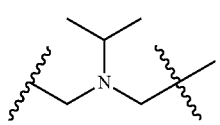 [SMILES: *CN(C*)C(C)C]
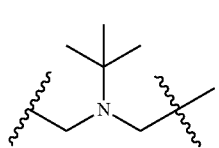 [SMILES: *CN(C*)C(C)(C)C]

TABLE 4-continued
| —T— |
|---|
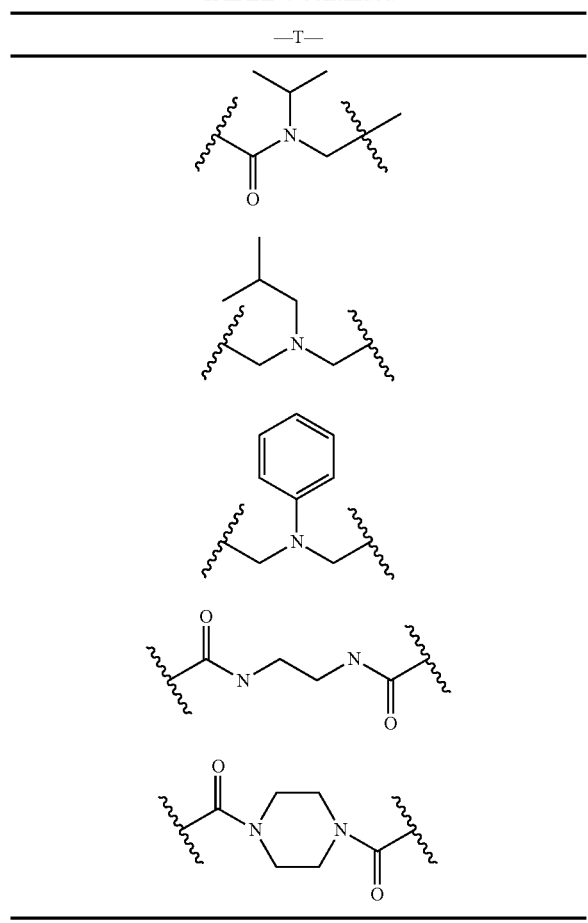
TABLE 5
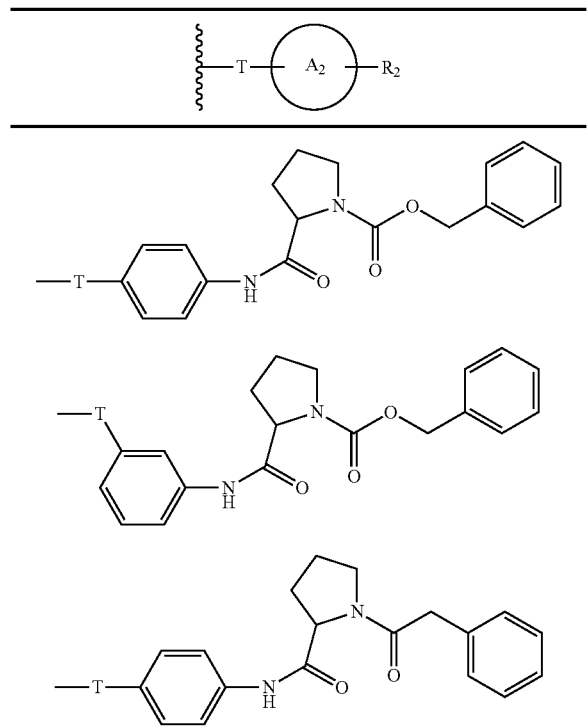
TABLE 5-continued
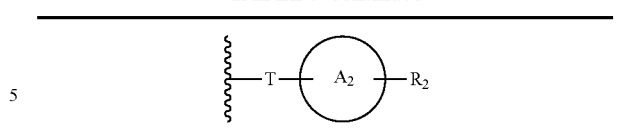
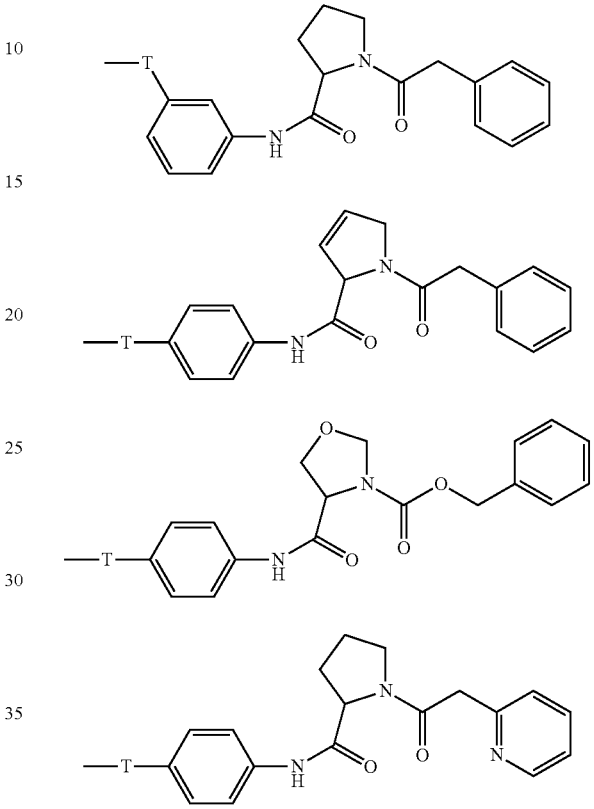

TABLE 5-continued
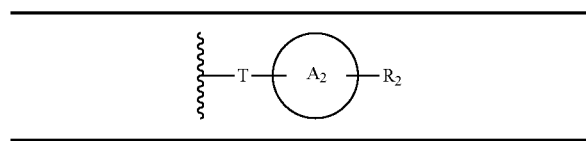
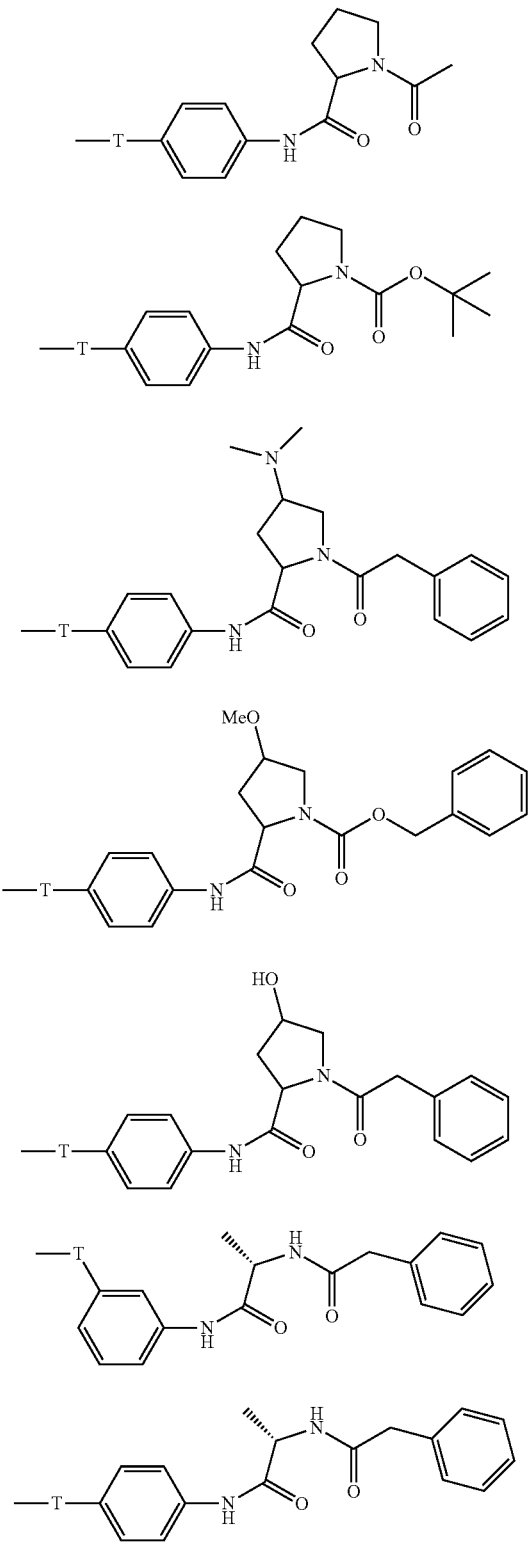
TABLE 5-continued
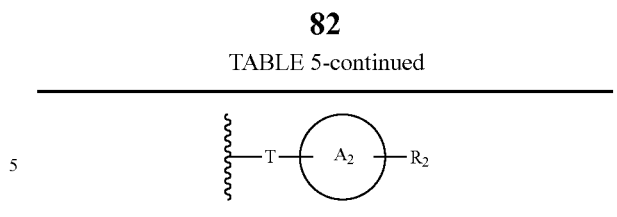
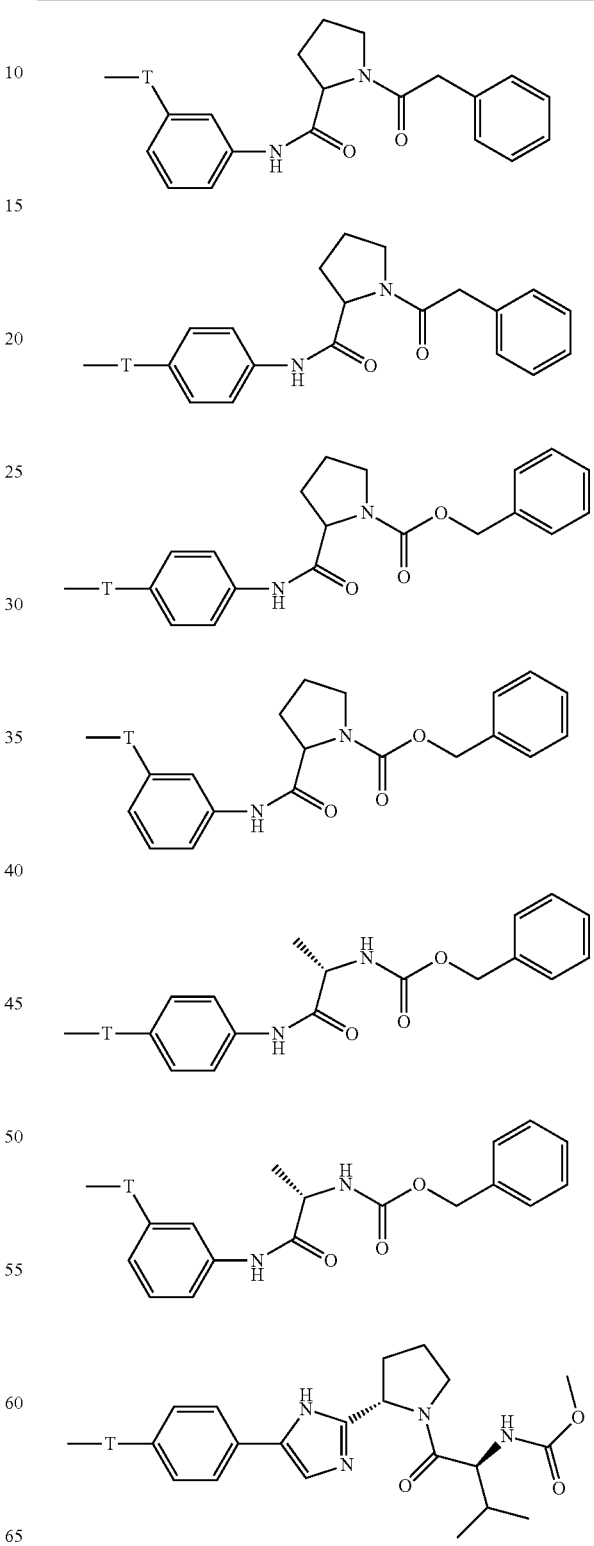

TABLE 5-continued
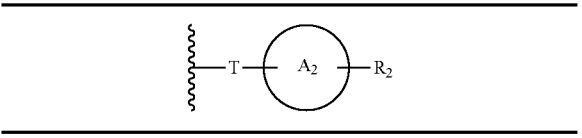
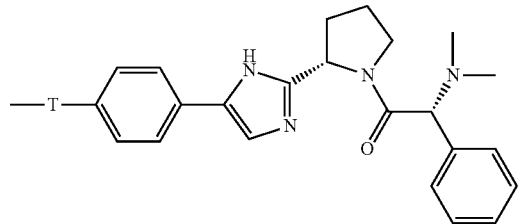
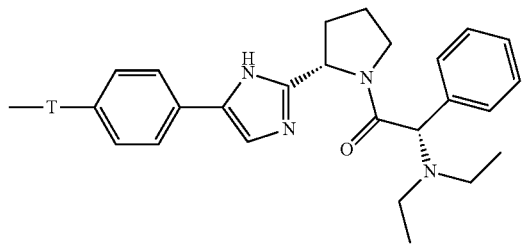
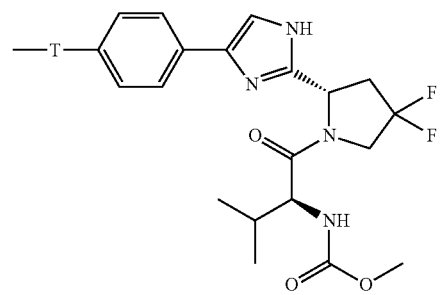
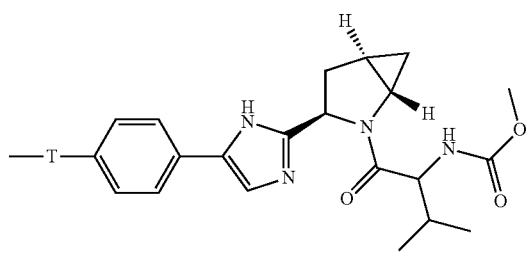
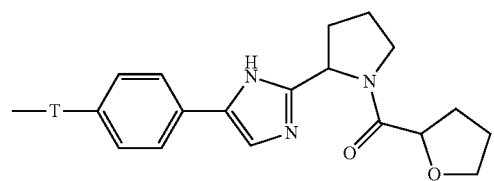
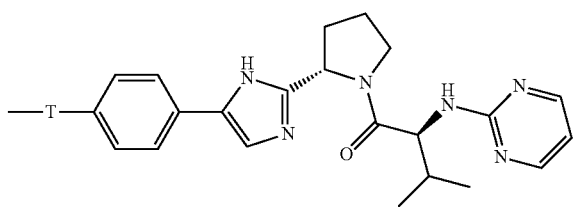
TABLE 5-continued
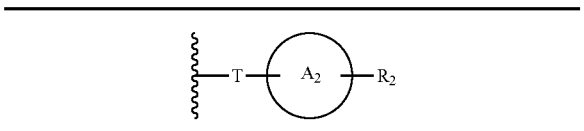
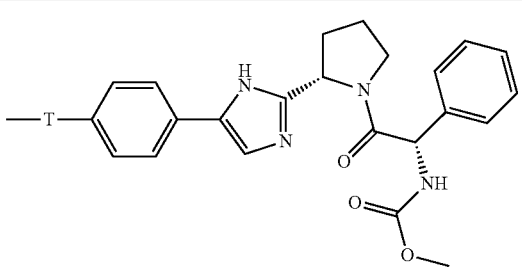
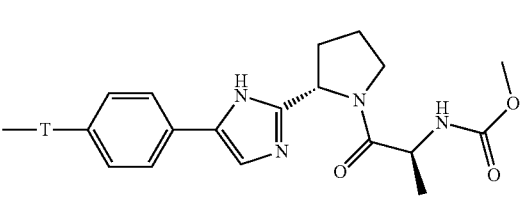
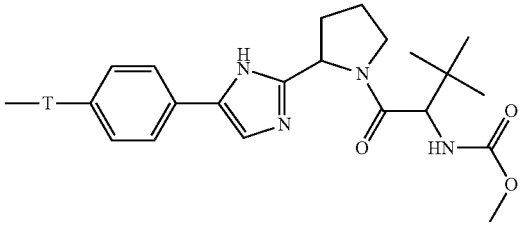
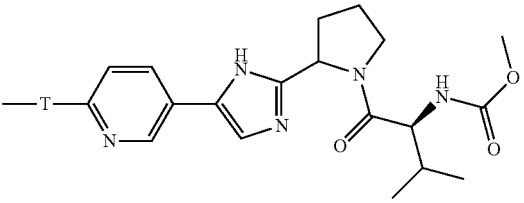
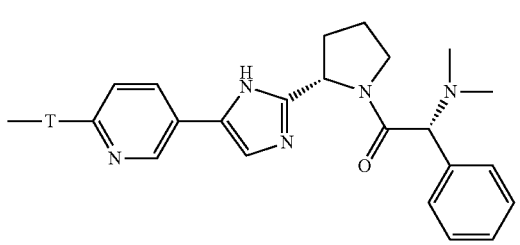
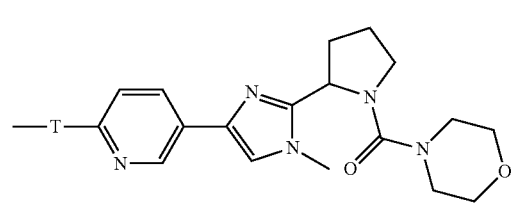

TABLE 5-continued
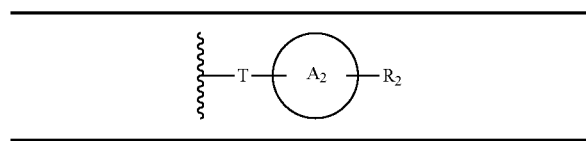
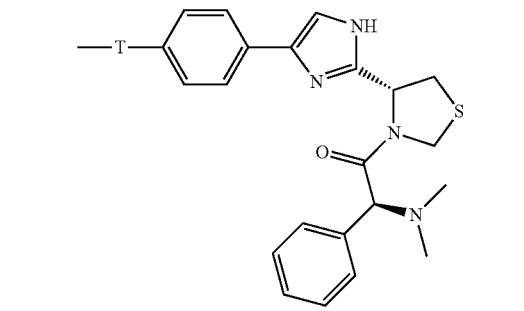
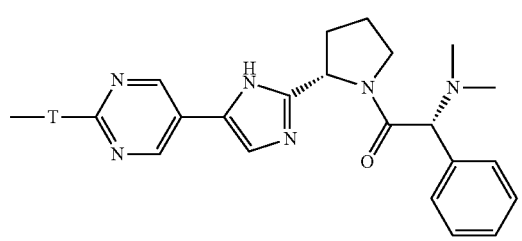
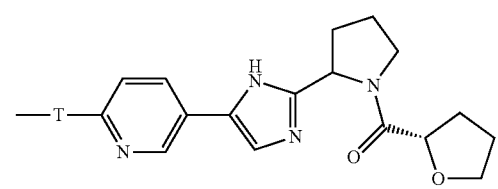
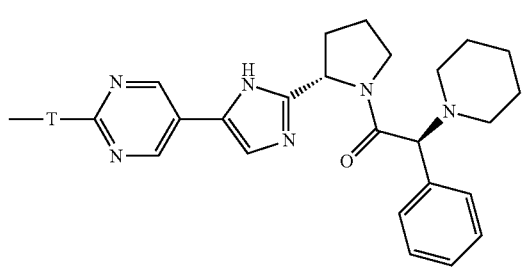
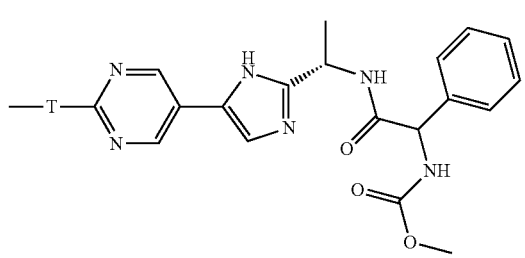
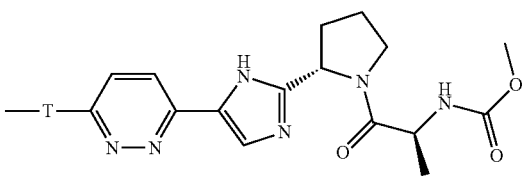
TABLE 5-continued
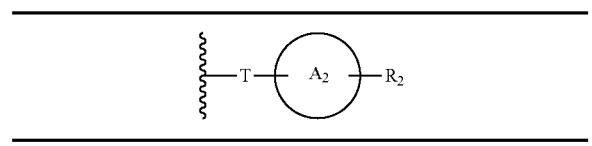
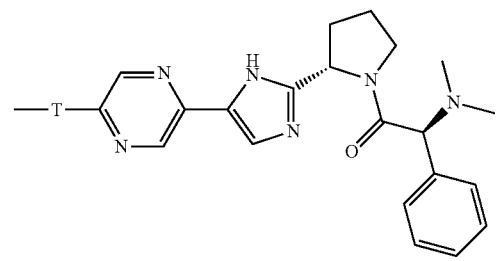
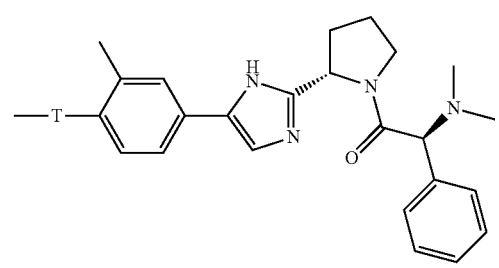
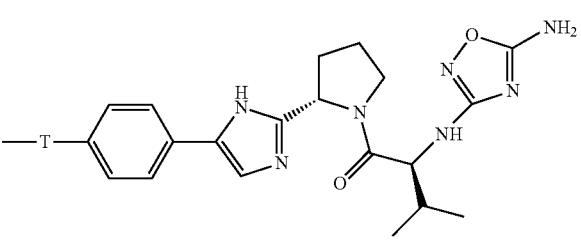
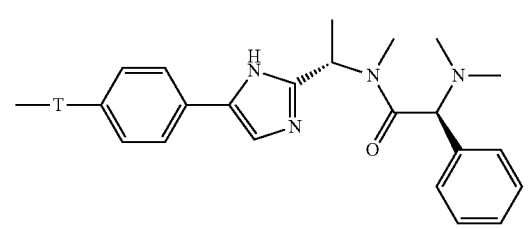
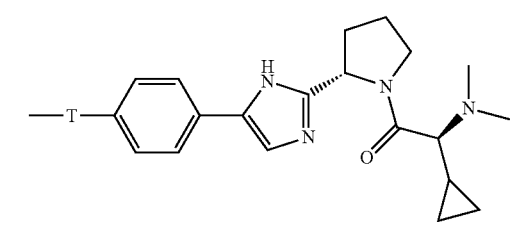
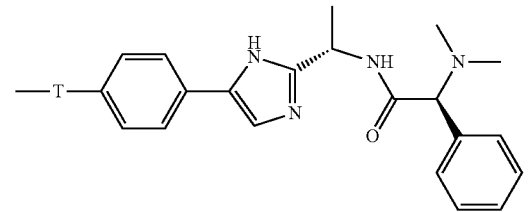

TABLE 5-continued
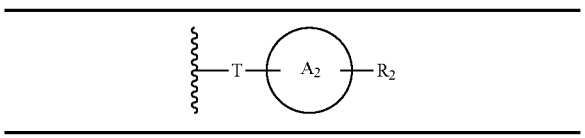
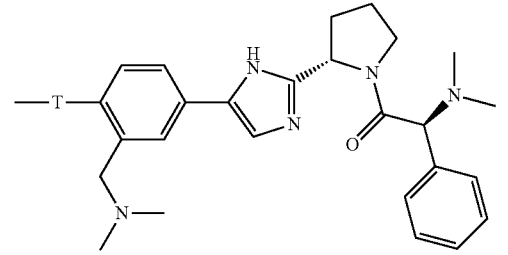
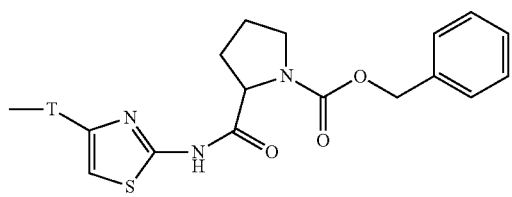
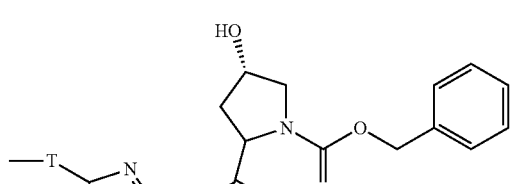
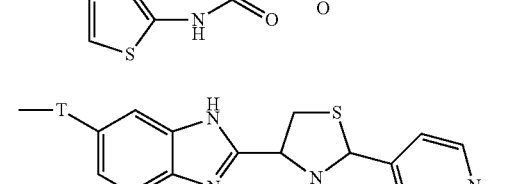
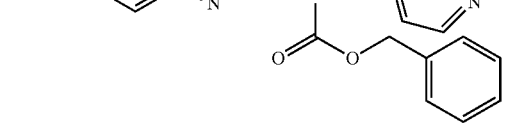
TABLE 5-continued
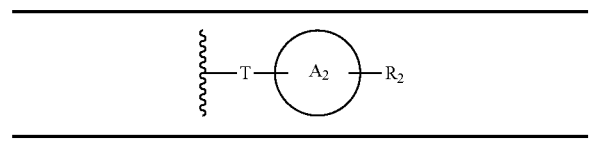
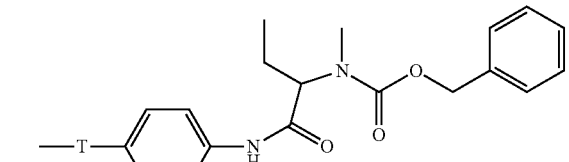
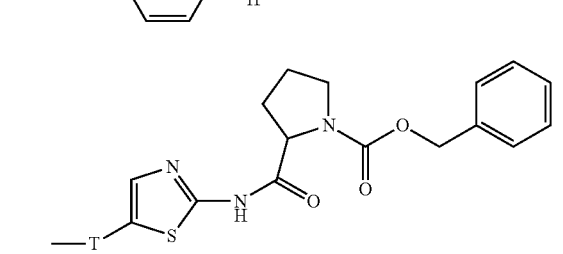
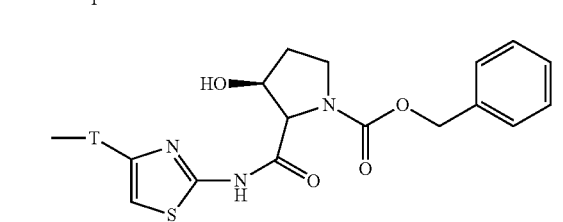
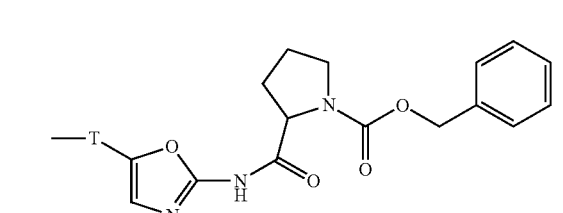
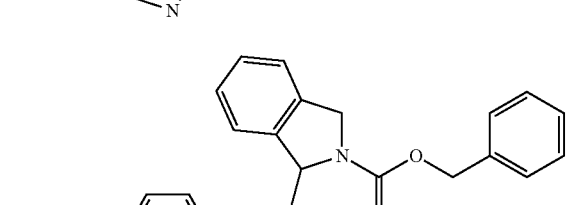
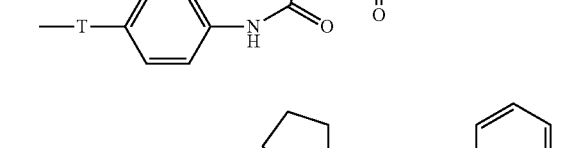
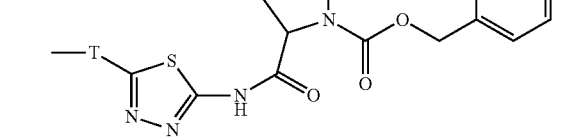
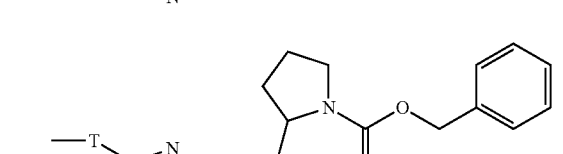
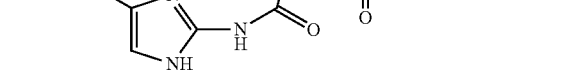

TABLE 5-continued
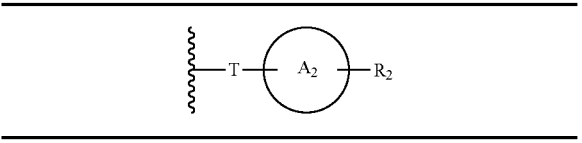
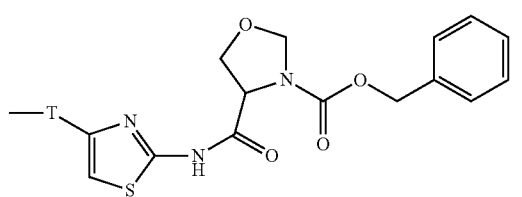
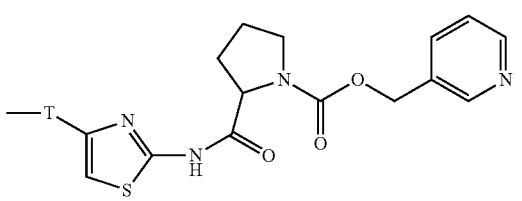
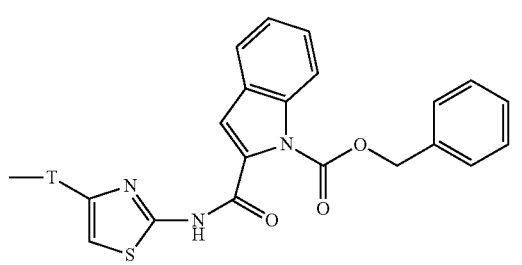
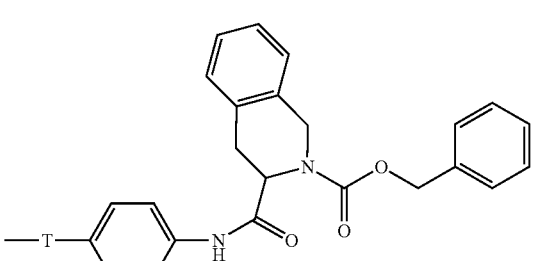
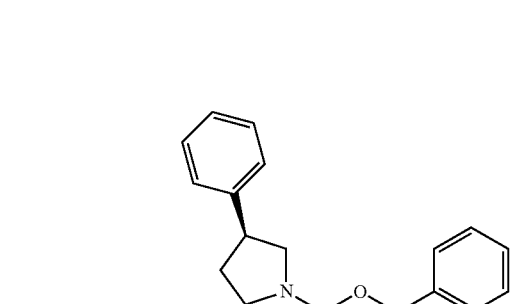
TABLE 5-continued
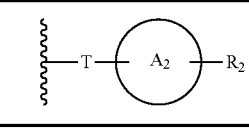
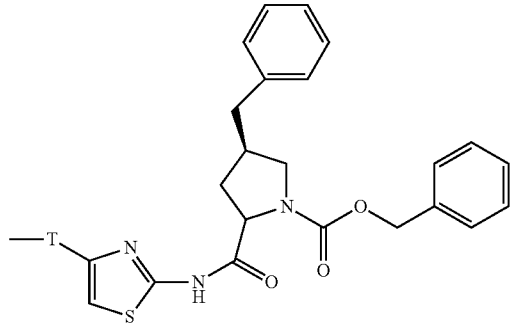
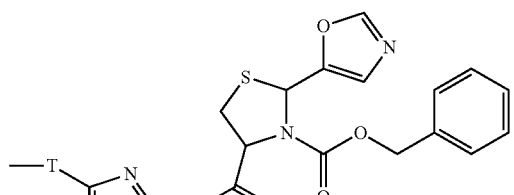
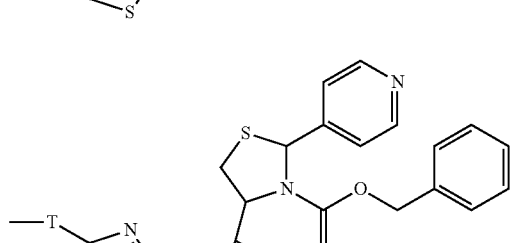
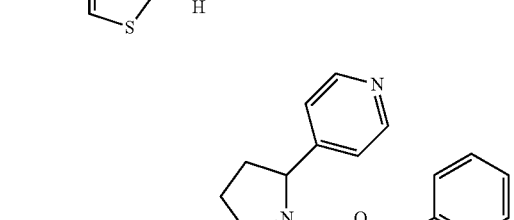
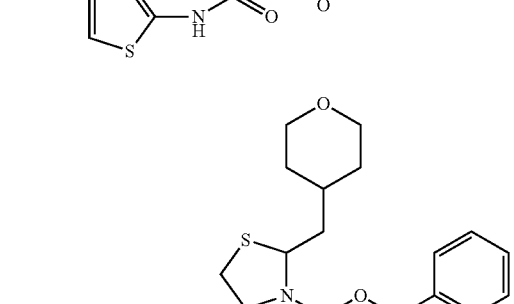

TABLE 5-continued

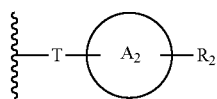

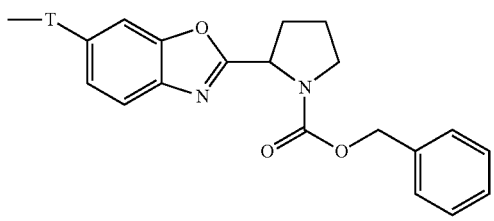

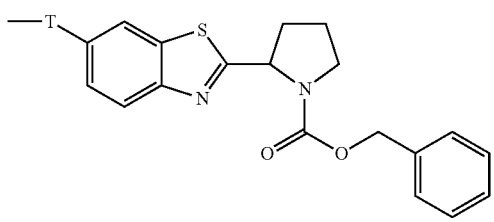

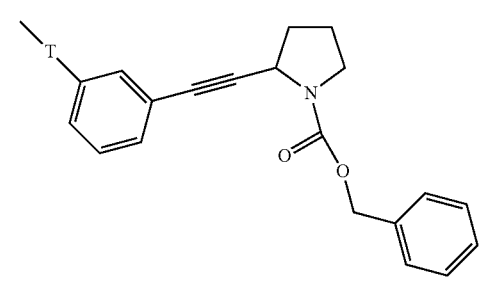

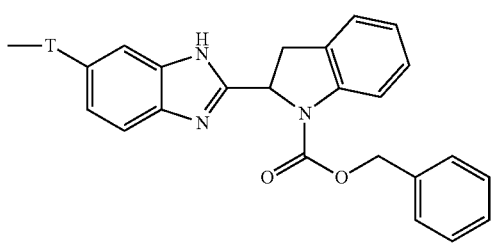

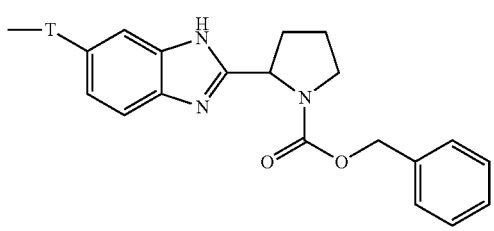

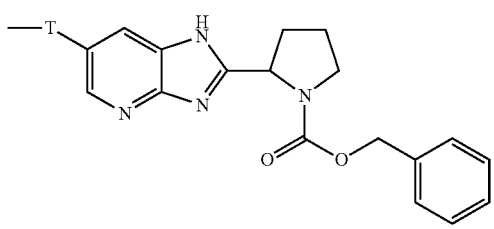

TABLE 5-continued

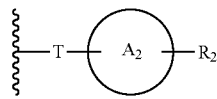

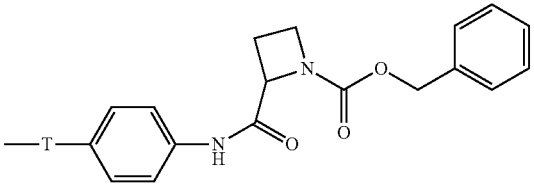

The inhibitory activities of the compounds of the present invention can be evaluated using a variety of assays known in the art. For instance, two stable subgenomic replicon cell lines can be used for compound characterization in cell culture: one derived from genotype 1a-H77 and the other derived from genotype 1b-Con1. The replicon constructs can be bicistronic subgenomic replicons. The genotype 1a replicon construct contains NS3-NS5B coding region derived from the H77 strain of HCV (1a-H77). The replicon also has a firefly luciferase reporter and a neomycin phosphotransferase (Neo) selectable marker. These two coding regions, separated by the FMDV 2a protease, comprise the first cistron of the bicistronic replicon construct, with the second cistron containing the NS3-NS5B coding region with addition of adaptive mutations. The 1b-Con1 replicon construct is identical to the 1a-H77 replicon, except that the NS3-NS5B coding region is derived from the 1b-Con1 strain, and that the replicon contains different adaptive mutations. Replicon cell lines can be maintained in Dulbecco's modified Eagles medium (DMEM) containing 10% (v/v) fetal bovine serum (FBS), 100 IU/ml penicillin, 100 mg/ml streptomycin (Invitrogen), and 200 mg/ml G418 (Invitrogen).

The inhibitory effects of the compounds of the invention on HCV replication can be determined by measuring activity of the luciferase reporter gene. For example, replicon-containing cells can be seeded into 96 well plates at a density of 5000 cells per well in 100 µl DMEM containing 5% FBS. The following day compounds can be diluted in dimethyl sulfoxide (DMSO) to generate a 200× stock in a series of eight half-log dilutions. The dilution series can then be further diluted 100-fold in the medium containing 5% FBS. Medium with the inhibitor is added to the overnight cell culture plates already containing 100 µl of DMEM with 5% FBS. In assays measuring inhibitory activity in the presence of human plasma, the medium from the overnight cell culture plates can be replaced with DMEM containing 40% human plasma and 5% FBS. The cells can be incubated for three days in the tissue culture incubators and are then lysed for RNA extraction. For the luciferase assay, 30 µl of Passive Lysis buffer (Promega) can be added to each well, and then the plates are incubated for 15 minutes with rocking to lyse the cells. Luciferin solution (100 µl Promega) can be added to each well, and luciferase activity can be measured with a Victor II luminometer (Perkin-Elmer). The percent Inhibition of HCV RNA replication can be calculated for each compound concentration and the $IC_{50}$ and/or $EC_{50}$ value can be calculated using nonlinear regression curve fitting to the 4-parameter logistic equation and GraphPad Prism 4 software.

When evaluated using the above method, representative compounds of the present invention inhibited HCV replicon replication with $IC_{50}$ values in the range of from about 0.1 nM to about 100 µM. $IC_{50}$ refers to 50% inhibitory concentration.

Cytotoxicity of the compounds of the present invention cart also be evaluated using methods known in the art. When tested, the $TC_{50}$ values of representative compounds of the present invention were often greater than the corresponding $IC_{50}$ values of the compounds. $TC_{50}$ refers to 50% toxicity concentration. Table 6 lists the $IC_{50}$ values of the compounds of Examples 1-18 when tested using HCV replicons.

TABLE 6

| Example | $IC_{50}$ for replicon 1b-Con1 |
|---|---|
| 1 | 10 nM-100 nM |
| 2 | 0.1 nM-10 nM |
| 3 | 0.1 nM-10 nM |
| 4 | 10 nM-100 nM |
| 5 | 0.1 nM-10 nM |
| 6 | 0.1 nM-10 nM |
| 7 | 0.1 nM-10 nM |
| 8 | 0.1 nM-10 nM |
| 9 | 0.1 nM-10 nM |
| 10 | 0.1 nM-10 nM |
| 11 | 0.1 nM-10 nM |
| 12 | 0.1 nM-10 nM |
| 13 | 0.1 nM-10 nM |
| 14 | 10 nM-100 nM |
| 15 | 10 nM-100 nM |
| 16 | 0.1 nM-10 nM |
| 17 | 0.1 nM-10 nM |
| 18 | 100 nM-10 μM |

The present invention also features pharmaceutical compositions comprising the compounds of the invention. A pharmaceutical composition of the present invention can comprise one or more compounds of the invention, each of which has a formula independently selected from selected from Formulae I, II or III.

In addition, the present invention features pharmaceutical compositions comprising pharmaceutically acceptable salts, solvates, or prodrugs of the compounds of the invention. Without limitation, pharmaceutically acceptable salts can be zwitterions or derived from pharmaceutically acceptable inorganic or organic acids or bases. Preferably, a pharmaceutically acceptable salt retains the biological effectiveness of the free acid or base of the compound without undue toxicity, irritation, or allergic response, has a reasonable benefit/risk ratio, is effective for the intended use, and is not biologically or otherwise undesirable.

The present invention further features pharmaceutical compositions comprising a compound of the invention (or a salt, solvate or prodrug thereof) and another therapeutic agent. By way of illustration not limitation, these other therapeutic agents can be selected from antiviral agents (e.g., anti-HIV agents, anti-HBV agents, or other anti-HCV agents such as HCV protease inhibitors, HCV polymerase inhibitors, HCV helicase inhibitors, IRES inhibitors or NS5A inhibitors), anti-bacterial agents, anti-fungal agents, immunomodulators, anti-cancer or chemotherapeutic agents, anti-inflammation agents, antisense RNA, siRNA, antibodies, or agents for treating cirrhosis or inflammation of the liver. Specific examples of these other therapeutic agents include, but are not limited to, ribavirin, α-interferon, β-interferon, pegylated interferon-α, pegylated interferon-lambda, ribavirin, viramidine, R-5158, nitazoxanide, amantadine, Debio-025, NIM-811, R7128, R1626, R4048, T-1106, PSI-7851, PF-00868554, ANA-598, IDX184, IDX102, IDX375, GS-9190, VCH-759, VCH-916, MK-3281, BCX-4678, MK-3281, VBY708, ANA598, GL59728, GL60667, BMS-790052, BMS-791325, BMS-650032, GS-9132, ACH-1095, AP-H005, A-831, A-689, AZD2836, telaprevir, boceprevir, ITMN-191, BI-201335, VBY-376, VX-500 (Vertex), PHX-B, ACH-1625, IDX136, IDX316, VX-813 (Vertex), SCH 900518 (Schering-Plough), TMC-435 (Tibotec), ITMN-191 (Intermune, Roche), MK-7009 (Merck), IDX-P1 (Novartis), BI-201335 (Boehringer Ingelheim), R7128 (Roche), PSI-7851 (Pharmasset), MK-3281 (Merck), PF-868554 (Pfizer), IDX-184 (Novartis), IDX-375 (Pharmasset), BILB-1944 (Boehringer Ingelheim), GS-9190 (Gilead), BMS-790052 (BMS), Albuferon (Novartis), ritonavir, another cytochrome P450 monooxygenase inhibitor, or any combination thereof.

In one embodiment, a pharmaceutical composition of the present invention comprises one or more compounds of the present invention (or salts, solvates or prodrugs thereof), and one or more other antiviral agents.

In another embodiment, a pharmaceutical composition of the present invention comprises one or more compounds of the present invention (or salts, solvates or prodrugs thereof), and one or more other anti-HCV agents. For example, a pharmaceutical composition of the present invention can comprise a compounds of the present Invention having Formula I, II or III (or (or a salts, solvate or prodrug thereof), and an agent selected from HCV polymerase inhibitors (including nucleoside or non-nucleoside type of polymerase inhibitors), HCV protease inhibitors, HCV helicase inhibitors, CD81 inhibitors, cyclophilin inhibitors, IRES inhibitors, or NS5A inhibitors.

In yet another embodiment, a pharmaceutical composition of the present invention comprises one or more compounds of the present invention (or salts, solvates or prodrugs thereof), and one or more other antiviral agents, such as anti-HBV, anti-HIV agents, or anti-hepatitis A, anti-hepatitis D, anti-hepatitis E or anti-hepatitis G agents. Non-limiting examples of anti-HBV agents include adefovir, lamivudine, and tenofovir. Non-limiting examples of anti-HIV drugs include ritonavir, lopinavir, Indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide, T-1249, or other HIV protease, reverse transcriptase, integrase or fusion inhibitors. Any other desirable antiviral agents can also be included in a pharmaceutical composition of the present invention, as appreciated by those skilled in the art.

A pharmaceutical composition of the present invention typically includes a pharmaceutically acceptable carrier or excipient. Non-limiting examples of suitable pharmaceutically acceptable carriers/excipients include sugars (e.g., lactose, glucose or sucrose), starches (e.g., corn starch or potato starch), cellulose or its derivatives (e.g., sodium carboxymethyl cellulose, ethyl cellulose or cellulose acetate), oils (e.g., peanut oil, cottonseed oil, safflower oil, sesame oil, olive oil, corn oil or soybean oil), glycols (e.g., propylene glycol), buffering agents (e.g., magnesium hydroxide or aluminum hydroxide), agar, alginic acid, powdered tragacanth, malt, gelatin, talc, cocoa butter, pyrogen-free water, isotonic salute, Ringer's solution, ethanol, or phosphate buffer solutions. Lubricants, coloring agents, releasing agents, coating agents, sweetening, flavoring or perfuming agents, preservatives, or antioxidants can also be included in a pharmaceutical composition of the present invention.

The pharmaceutical compositions of the present invention can be formulated based on their routes of administration using methods well known in the art. For example, a sterile injectable preparation can be prepared as a sterile injectable aqueous or oleagenous suspension using suitable dispersing or wetting agents and suspending agents. Suppositories for rectal administration can be prepared by mixing drugs with a suitable nonirritating excipient such as cocoa butter or polyethylene glycols which are solid at ordinary temperatures but liquid at the rectal temperature and will therefore melt in the rectum and release the drugs. Solid dosage forms for oral administration can be capsules, tablets, pills, powders or granules. In such solid dosage forms, the active compounds can be admixed with at least one Inert diluent such as sucrose lactose or starch. Solid dosage forms may also comprise other substances in addition to inert diluents, such as lubricating agents. In the case of capsules, tablets and pills, the dosage forms may also comprise buffering agents. Tablets and pills can additionally be prepared with enteric coatings. Liquid dosage forms for oral administration can include pharmaceutically acceptable emulsions, solutions, suspensions, syrups or elixirs containing inert diluents commonly used in the art. Liquid dosage forms may also comprise wetting, emulsifying, suspending, sweetening, flavoring, or perfuming agents. The pharmaceutical compositions of the present invention can also be administered in the form of liposomes, as described in U.S. Pat. No. 6,703,403. Formulation of drugs that are applicable to the present invention is generally discussed in, for example, Hoover, John E., REMINGTONS'S PHARMACEUTICAL SCIENCES (Mack Publishing Co., Easton, Pa.: 1975), and Lachman, L., eds., PHARMACEUTICAL DOSAGE FORMS (Marcel Decker, New York, N.Y., 1980).

Any compound described herein, or a pharmaceutically acceptable salt thereof, can be used to prepared pharmaceutical compositions of the present invention.

The present invention further features methods of using the compounds of the present invention (or salts, solvates or prodrugs thereof) to inhibit HCV replication. The methods comprise contacting cells infected with HCV virus with an effective amount of a compound of the present invention (or a salt, solvate or prodrug thereof), thereby inhibiting the replication of HCV virus in the cells. As used herein, "inhibiting" means significantly reducing, or abolishing, the activity being inhibited (e.g., viral replication). In many cases, representative compounds of the present invention can reduce the replication of HCV virus (e.g., in an HCV replicon assay as described above) by at least 10%, 20%, 30%, 40%, 50%, 60%, 70%, 80%, 90%, 95% or more.

The compounds of the present invention may Inhibit all HCV subtypes. Examples of HCV subtypes that are amenable to the present invention include, but are not be limited to, HCV genotypes 1, 2, 3, 4, 5 and 6, including HCV genotypes 1a, 1b, 2a, 2b, 2c or 3a. In one embodiment, a compound or compounds of the present invention (or salts, solvates or prodrugs thereof) are used to inhibit the replication of HCV genotype 1a. In another embodiment, a compound or compounds of the present invention (or salts, solvates or prodrugs thereof) are used to inhibit the replication of HCV genotype 1b. In still another embodiment, a compound or compounds of the present invention (or salts, solvates or prodrugs thereof) are used to inhibit the replication of both HCV genotypes 1a and 1b.

The present invention also features methods of using the compounds of the present Invention (or salts, solvates or prodrugs thereof) to beat HCV infection. The methods typically comprise administering a therapeutic effective amount of a compound of the present invention (or a salt, solvate or prodrug thereof), or a pharmaceutical composition comprising the same, to an HCV patient, thereby reducing the HCV viral level in the blood or liver of the patient. As used herein, the term "treating" refers to reversing, alleviating, inhibiting the progress of, or preventing the disorder or condition, or one or more symptoms of such disorder or condition to which such term applies. The term "treatment" refers to the act of treating. In one embodiment, the methods comprise administering a therapeutic effective amount of two or more compounds of the present invention (or salts, solvates or prodrugs thereof), or a pharmaceutical composition comprising the same, to an HCV patient, thereby reducing the HCV viral level in the blood or liver of the patient.

A compound of the present invention (or a salt, solvate or prodrug thereof) can be administered as the sole active pharmaceutical agent, or in combination with another desired drug, such as other anti-HCV agents, anti-HIV agents, anti-HBV agents, anti-hepatitis A agents, anti-hepatitis D agents, anti-hepatitis E agents, anti-hepatitis G agents, or other antiviral drugs. Any compound described herein, or a pharmaceutically acceptable salt thereof, can be employed in the methods of the present invention.

A compound of the present invention (or a salt, solvent or prodrug thereof) can be administered to a patient in a single dose or divided doses. A typical daily dosage can range, without limitation, from 0.1 to 200 mg/kg body weight, such as from 0.25 to 100 mg/kg body weight. Single dose compositions can contain these amounts or submultiples thereof to make up the daily dose. Preferably, each dosage contains a sufficient amount of a compound of the present invention that is effective in reducing the HCV viral load in the blood or liver of the patient. The amount of the active ingredient, or die active ingredients that are combined, to produce a single dosage form may vary depending upon the host treated and the particular mode of administration. It will be understood that the specific dose level for any particular patient will depend upon a variety of factors including the activity of the specific compound employed, the age, body weight, general health, sex, diet, time of administration, route of administration, rats of excretion, drug combination, and the severity of the particular disease undergoing therapy.

The present invention former features methods of using the pharmaceutical compositions of the present invention to treat HCV infection. The methods typically comprise administering a pharmaceutical composition of the present invention to an HCV patient, thereby reducing the HCV viral level in the blood or liver of the patient. Any pharmaceutical composition described herein can be used in the methods of the present invention.

In addition, the present invention features use of the compounds or salts of the present invention for the manufacture of medicaments for the treatment of HCV infection. Any compound described herein, or a pharmaceutically acceptable salt thereof, can be used to make medicaments of the present invention.

The foregoing description of the present invention provides illustration and description, but is not intended to be exhaustive or to limit the invention to the precise one disclosed. Modifications and variations are possible is light of the above teachings or may be acquired from practice of the invention. Thus, it is noted that the scope of the invention is defined by the claims and their equivalents.

What is claimed is:

1. A compound of Formula I, or a pharmaceutically acceptable salt thereof,

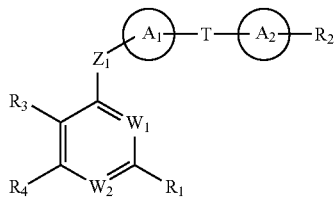

wherein:
- $A_1$ is $C_3$-$C_{14}$carbocyclyl or 3- to 14-membered heterocyclyl, and is substituted with —$X_1$—$R_7$, wherein said $C_3$-$C_{14}$carbocyclyl and 3- to 14-membered heterocyclyl are optionally substituted with one or more $R_A$;
- $X_1$ is selected from a bond, -$L_S$-, —O—, —S—, or —N($R_B$)—;
- $R_7$ is selected from hydrogen, -$L_A$, $C_5$-$C_{10}$carbocyclyl, or 5- to 10-membered heterocyclyl, wherein at each occurrence said $C_5$-$C_{10}$carbocyclyl and 5- to 10-membered heterocyclyl are each independently optionally substituted with one or more $R_A$;
- $Z_1$ is selected from a bond, —C($R_C R_{C'}$)—, —O—, —S—, or —N($R_B$)—;
- $W_1$ and $W_2$ are each independently selected from N or C($R_D$);
- $R_1$ is selected from hydrogen or $R_A$;
- $R_3$ and $R_4$ are each independently selected from hydrogen or $R_A$; or $R_3$ and $R_4$, taken together with the carbon atoms to which they are attached, form a $C_5$-$C_{10}$carbocyclic or 5- to 10-membered heterocyclic ring, wherein said $C_5$-$C_{10}$carbocyclic and 5- to 10-membered heterocyclic ring are optionally substituted with one or more $R_A$;
- $A_2$ is $C_3$-$C_{14}$carbocyclyl or 3- to 14-membered heterocyclyl, and is optionally substituted with one or more $R_A$;
- $R_2$ is —N($R_B$)C(O)C($R_5 R_6$)N($R_8$)-T-$R_D$,

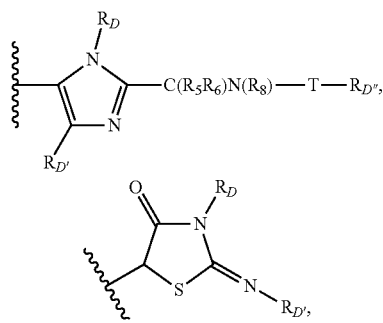

or -$L_K$-B;
- $R_5$ is $R_C$;
- $R_6$ is $R_{C'}$, and $R_8$ is $R_B$; or $R_6$ and $R_8$, taken together with the atoms to which they are attached, form a 3- to 10-membered heterocyclic ring which is optionally substituted with one or more $R_A$;
- $L_K$ is a bond; $C_1$-$C_6$alkylene, $C_2$-$C_6$alkenylene, or $C_2$-$C_6$alkynylene, each of which is independently optionally substituted at each occurrence with one or more substituents selected from halogen, $R_S$ (except hydrogen), —O—$R_S$, —S—$R_S$, —N($R_S R_{S'}$), —OC(O)$R_S$, —C(O)O$R_S$, nitro, phosphate, oxo, thioxo, formyl or cyano; or —N($R_B$)C(O)— or —C(O)N($R_B$)—;
- B is $C_3$-$C_{10}$carbocycle or 3- to 10-membered heterocycle, and is optionally substituted with one or more $R_A$;
- T is independently selected at each occurrence from a bond, -$L_S$-, -$L_S$-M-$L_{S'}$-, -$L_S$-M-$L_S$, -M'-$L_{S''}$-, wherein M and M' are each independently selected from a bond, —O—, —S—, —N($R_B$)—, —C(O)—, —S(O)$_2$—, —S(O)—, —OS(O)—, —OS(O)$_2$—, —S(O)$_2$O—, —S(O)O—, —C(O)O—, —OC(O)—, —OC(O)O—, —C(O)N($R_B$)—, —N($R_B$)C(O)—, —N($R_B$)C(O)O—, —OC(O)N($R_B$)—, —N($R_B$)S(O)—, —N($R_B$)S(O)$_2$—, —S(O)N($R_B$)—, —S(O)$_2$N($R_B$)—, —C(O)N($R_B$)C(O)—, —N($R_B$)C(O)N($R_{B'}$)—, —N($R_B$)SO$_2$N($R_{B'}$)—, —N($R_B$)S(O)N($R_{B'}$)—, $C_5$-$C_{10}$carbocycle, or 5- to 10-membered heterocycle, and wherein at each occurrence T is independently optionally substituted with one or more $R_A$;
- $R_A$ is independently selected at each occurrence from halogen, hydroxy, mercapto, amino, carboxy, nitro, phosphate, oxo, thioxo, formyl, cyano, -$L_A$, or -$L_S$-$R_E$;
- $R_B$ and $R_{B'}$ are each independently selected at each occurrence from hydrogen; or $C_1$-$C_6$alkyl, $C_2$-$C_6$alkenyl, $C_2$-$C_6$alkynyl, $C_3$-$C_6$carbocyclyl, $C_3$-$C_6$carbocyclyl$C_1$-$C_6$alkyl, 3- to 6-membered heterocyclyl, or (3- or 6-membered heterocyclyl)$C_1$-$C_6$alkyl, each of which is independently optionally substituted at each occurrence with one or more substituents selected from halogen, hydroxy, mercapto, amino, carboxy, nitro, phosphate, oxo, thioxo, formyl or cyano;
- $R_C$ and $R_{C'}$ are each independently selected at each occurrence from hydrogen; halogen; hydroxy; mercapto; amino; carboxy; nitro; phosphate; oxo; thioxo; formyl; cyano; or $C_1$-$C_6$alkyl, $C_2$-$C_6$alkenyl, $C_2$-$C_6$alkynyl, or $C_3$-$C_6$carbocyclyl, each of which is independently optionally substituted at each occurrence with one or more substituents selected from halogen, hydroxy, mercapto, amino, carboxy, nitro, phosphate, oxo, thioxo, formyl or cyano;
- $R_D$, $R_{D'}$ and $R_{D''}$ are each independently selected at each occurrence from hydrogen or $R_A$
- $L_A$ is independently selected at each occurrence from $C_1$-$C_6$alkyl, $C_2$-$C_6$alkenyl, or $C_2$-$C_6$alkynyl, each of which is independently optionally substituted at each occurrence with one or more substituents selected from halogen, —O—$R_S$, —S—$R_S$, —N($R_S R_{S'}$), —OC(O)$R_S$, —C(O)O$R_S$, nitro, phosphate, oxo, thioxo, formyl or cyano;
- $L_S$, $L_{S'}$ and $L_{S''}$ are each independently selected at each occurrence from a bond; or $C_1$-$C_6$alkylene, $C_2$-$C_6$alkenylene, or $C_2$-$C_6$alkynylene, each of which is independently optionally substituted at each occurrence with one or more substituents selected from halogen, —O—$R_S$, —S—$R_S$, —N($R_S R_{S'}$), —OC(O)$R_S$, —C(O)O$R_S$, nitro, phosphate, oxo, thioxo, formyl or cyano;
- $R_E$ is independently selected at each occurrence from —O—$R_S$, —S—$R_S$, —C(O)$R_S$, —OC(O)$R_S$, —C(O)O$R_S$, —N($R_S R_{S'}$), —S(O)$R_S$, —SO$_2 R_S$, —C(O)N($R_S R_{S'}$), —N($R_S$)C(O)$R_{S'}$, —N($R_S$)C(O)N($R_S R_{S'}$), —N($R_S$)SO$_2 R_{S'}$, —SO$_2$N($R_S R_{S'}$), —N($R_S$)SO$_2$N($R_S R_{S''}$), —N($R_S$)S(O)N($R_S R_{S''}$), —OS(O)—$R_S$, —OS(O)$_2$—$R_S$, —S(O)$_2$O$R_S$, —S(O)O$R_S$, —OC(O)O$R_S$, —N($R_S$)C(O)O$R_{S'}$, —OC(O)N($R_S R_{S'}$), —N($R_S$)S(O)—$R_{S'}$, —S(O)N($R_S R_{S'}$), —C(O)N($R_S$)C(O)—$R_{S'}$, $C_3$-$C_{10}$carbocyclyl, or 3- to 10-membered heterocyclyl, wherein said $C_3$-$C_{10}$carbocyclyl and 3- to 10-membered heterocyclyl are each independently optionally substituted at each occurrence with one or more substituents selected from $C_1$-$C_6$alkyl, $C_2$-$C_6$alkenyl, $C_2$-$C_6$alkynyl, $R_S$ (except hydrogen), halogen, —O—$R_B$, —S—$R_B$, —N($R_B R_{B'}$), —OC(O)$R_B$, —C(O)O$R_B$, nitro, phosphate, oxo, thioxo, formyl or cyano; and $R_S$, $R_{S'}$ and $R_{S''}$ are each independently selected at each occurrence from hydrogen; or $C_1$-$C_6$alkyl, $C_2$-$C_6$alkenyl, $C_2$-$C_6$alkynyl, $C_3$-$C_6$carbocyclyl, $C_3$-$C_6$carbocyclyl$C_1$-$C_6$alkyl, 3- to 6-membered heterocyclyl, or (3- or 6-membered heterocyclyl)$C_1$-$C_6$alkyl, each of which is independently optionally substituted at each occurrence with one or more substituents selected from halogen, —O—$R_B$, —S—$R_B$, —N($R_B R_{B'}$), —OC(O)$R_B$, —C(O)O$R_B$, nitro, phosphate, oxo, thioxo, formyl or cyano.

2. The compound or salt of claim 1, wherein:
$A_1$ is $C_5$-$C_6$carbocyclyl or 5- to 6-membered heterocyclyl, which is optionally substituted with one or more $R_4$, and $A_1$ is substituted with —$X_1$—$R_7$;
$R_7$ is $C_5$-$C_6$carbocyclyl or 5- to 6-membered heterocyclyl, and is optionally substituted with one or more $R_4$;
$R_3$ and $R_4$ are each independently selected from hydrogen or $R_4$; or $R_3$ and $R_4$, taken together with the carbon atoms to which they are attached, form a $C_5$-$C_6$carbocyclic or 5- to 6-membered heterocyclic ring, wherein said $C_5$-$C_6$carbocyclic and 5- to 6-membered heterocyclic ring are optionally substituted with one or more $R_4$; and
$A_2$ is $C_5$-$C_{10}$carbocyclyl or 5- to 10-membered heterocyclyl, and is optionally substituted with one or more $R_4$.

3. The compound or salt of claim 2, wherein $A_2$ is $C_5$-$C_6$carbocyclyl or 5- to 6-membered heterocyclyl, and is optionally substituted with one or more $R_4$.

4. The compound or salt of claim 2, wherein $R_7$ is phenyl, and is optionally substituted with one or more $R_4$.

5. The compound or salt of claim 2, wherein $A_1$ is phenyl, and is optionally substituted with one or more $R_4$.

6. The compound or salt of claim 2, wherein $A_2$ is phenyl, and is optionally substituted with one or more $R_4$.

7. The compound or salt of claim 2, wherein $A_1$, $A_2$ and $R_7$ are phenyl, and are each independently optionally substituted with one or more $R_4$.

8. The compound or salt of claim 2, wherein $R_3$ and $R_4$, taken together with the carbon atoms to which they are attached, form a $C_5$-$C_6$carbocyclic or 5- to 6-membered heterocyclic ring which is optionally substituted with one or more $R_4$.

9. The compound or salt of claim 2, wherein $W_1$ and $W_2$ are N, and $Z_1$ is —N($R_B$)—.

10. The compound or salt of claim 2, wherein:
$W_1$ and $W_2$ are N;
$Z_1$ is —N($R_B$)—;
$X_1$ is —CH$_2$—, —O—, or —S—;
$R_3$ and $R_4$, taken together with the carbon atoms to which they are attached, form

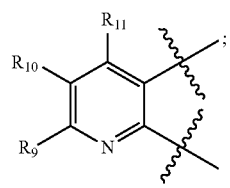

$R_9$, $R_{10}$, and $R_{11}$ are each independently selected from hydrogen or $R_4$.

11. The compound or salt of claim 10, wherein
$A_1$ is phenyl, and is optionally substituted with one or more $R_4$;
$R_7$ is phenyl, and is optionally substituted with one or more $R_4$;
$R_1$ is hydrogen;
$R_9$, $R_{10}$, and $R_{11}$ are each independently selected from hydrogen; halogen; or $C_1$-$C_6$alkyl, $C_2$-$C_6$alkenyl, $C_2$-$C_6$alkynyl, $C_3$-$C_6$carbocyclyl, or $C_3$-$C_6$carbocyclyC$_1$-$C_6$alkyl, each of which is independently optionally substituted at each occurrence with one or more substituents selected from halogen, hydroxy, mercapto, amino, carboxy, nitro, phosphate, oxo, thioxo, formyl or cyano.

12. The compound or salt of claim 1, wherein $R_2$ is —N($R_B$)C(O)C($R_5 R_6$)N($R_8$)-T-$R_D$.

13. The compound or salt of claim 12, wherein R5 is $R_C$, and R6 and R8 taken together with the atoms to which they are attached form a 5- to 6-membered heterocyclic ring which is optionally substituted with one or more $R_4$.

14. The compound or salt of claim 12, wherein:
$R_5$ is H;
$R_6$ and $R_8$, taken together with the atoms to which they are attached, form

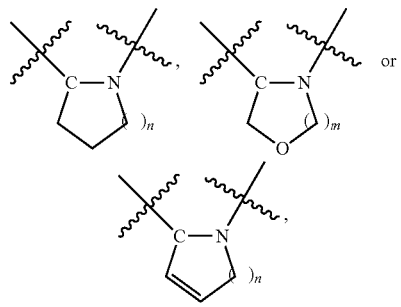

each of which is independently optionally substituted with one or more $R_4$;
n is 0, 1 or 2; and
m is 1 or 2.

15. The compound or salt of claim 14, wherein:
-T-$R_D$ is —C(O)-$L_{S'}$-$R_{12}$ or —C(O)-$L_{S'}$-M'-$L_{S'}$-$R_{12}$; and
$R_{12}$ is hydrogen; $C_1$-$C_6$alkyl, $C_2$-$C_6$alkenyl or $C_2$-$C_6$alkynyl, each of which is independently optionally substituted at each occurrence with one or more substituents selected from halogen, —O—$R_S$, —S—$R_S$, —N($R_S R_{S'}$), —OC(O)$R_S$, —C(O)O$R_S$, nitro, phosphate, oxo, thioxo, formyl or cyano; or $C_3$-$C_{10}$carbocyclyl or 3- to 10-membered heterocyclyl, each of which is independently optionally substituted at each occurrence with one or more substituents selected from $C_1$-$C_6$alkyl, $C_2$-$C_6$alkenyl, $C_2$-$C_6$alkynyl, halogen, —O—$R_B$, —S—$R_B$, —N($R_B R_{B'}$), —OC(O)$R_B$, —C(O)O$R_B$, nitro, phosphate, oxo, thioxo, formyl or cyano.

16. The compound or salt of claim 1, wherein $R_2$ is

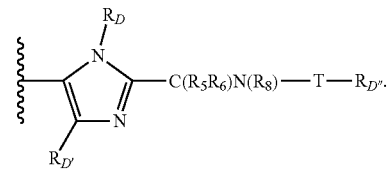

17. The compound or salt of claim 16, wherein R5 is $R_C$, and $R_6$ and $R_8$, taken together with the atoms to which they are attached, form a 5- to 6-membered heterocyclic ring which is optionally substituted with one or more $R_A$.

18. The compound or salt of claim 16, wherein:
$R_5$ is H;
$R_6$ and $R_8$, taken together with the atoms to which they are attached, form

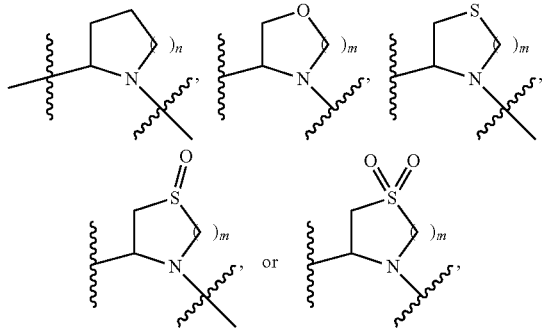

which is optionally substituted with one or more $R_A$;
n is 0, 1 or 2; and
m is 1 or 2.

19. The compound or salt of claim 18, wherein:
-T-$R_{D''}$ is —C(O)-$L_{S'}$-$R_{12}$ or —C(O)-$L_{S'}$-M'-$L_{S''}$-$R_{12}$; and $R_{12}$ is hydrogen; $C_1$-$C_6$alkyl, $C_2$-$C_6$alkenyl or $C_2$-$C_6$alkynyl, each of which is independently optionally substituted at each occurrence with one or more substituents selected from halogen, —O—$R_S$, —S—$R_S$, —N($R_S R_{S'}$), —OC(O)$R_S$, —C(O)O$R_S$, nitro, phosphate, oxo, thioxo, formyl or cyano; or $C_3$-$C_{10}$carbocyclyl or 3- to 10-membered heterocyclyl, each of which is independently optionally substituted at each occurrence with one or more substituents selected from $C_1$-$C_6$alkyl, $C_2$-$C_6$alkenyl, $C_2$-$C_6$alkynyl, halogen, —O—$R_B$, —S—$R_B$, —N($R_B R_{B'}$), —OC(O)$R_B$, —C(O)O$R_B$, nitro, phosphate, oxo, thioxo, formyl or cyano.

20. The compound or salt of claim 1, wherein R2 is

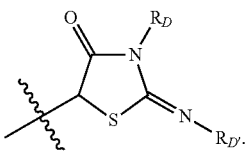

21. The compound or salt of claim 1, wherein $R_2$ is -$L_K$-B.

22. The compound or salt of claim 21, wherein B is $C_3$-$C_{10}$carbocycle or 3- to 10-membered heterocycle, and is optionally substituted with one or more $R_A$.

23. The compound or salt of claim 21, wherein B is

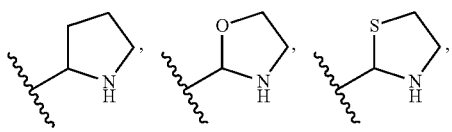

-continued

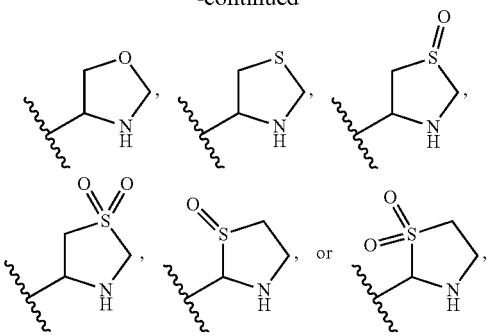

and is optionally substituted with one or more $R_A$.

24. The compound or salt of claim 21, wherein:
B is

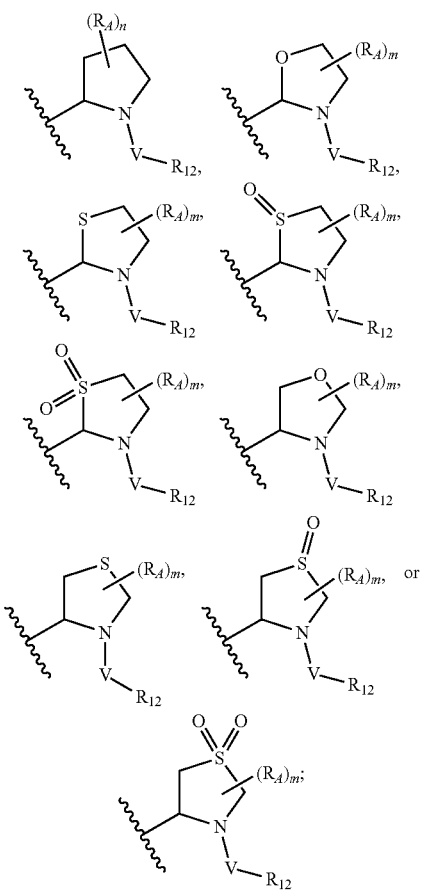

n is 0, 1, 2, 3, or 4;
m is 0, 1, 2, or 3;
V is —C(O)— or —S(O)$_2$—;
$R_{12}$ is —$R_S$, —O$R_S$, or —N($R_S R_{S'}$).

25. A pharmaceutical composition comprising a compound or salt according to claim 1.

26. A process of making a compound according to claim 1, comprising a step described in one of schemes described herein.

* * * * *

(12) EX PARTE REEXAMINATION CERTIFICATE (11720th)
United States Patent
Degoey et al.

(10) Number: US 9,163,017 C1
(45) Certificate Issued: *Sep. 4, 2020

(54) ANTI-VIRAL COMPOUNDS

(71) Applicant: ABBVIE INC., North Chicago, IL (US)

(72) Inventors: David A. Degoey, Salem, WI (US); Pamela L. Donner, Mundelein, IL (US); Warren M. Kati, Gurnee, IL (US); Charles W. Hutchins, Green Oaks, IL (US); Mark A. Matulenko, Libertyville, IL (US); Tammie K. Jinkerson, Pleasant Prairie, WI (US); Ryan G. Keddy, Beach Park, IL (US)

(73) Assignee: AbbVie Inc.

Reexamination Request:
No. 90/014,436, Jan. 18, 2020

Reexamination Certificate for:
Patent No.: 9,163,017
Issued: Oct. 20, 2015
Appl. No.: 14/021,435
Filed: Sep. 9, 2013

( * ) Notice: This patent is subject to a terminal disclaimer.

Related U.S. Application Data

(63) Continuation of application No. 12/644,427, filed on Dec. 22, 2009, now Pat. No. 8,541,424.

(60) Provisional application No. 61/140,262, filed on Dec. 23, 2008.

(51) Int. Cl.
*C07D 471/04* (2006.01)

(52) U.S. Cl.
CPC .................................. *C07D 471/04* (2013.01)

(58) Field of Classification Search
None
See application file for complete search history.

(56) References Cited

To view the complete listing of prior art documents cited during the proceeding for Reexamination Control Number 90/014,436, please refer to the USPTO's public Patent Application Information Retrieval (PAIR) system under the Display References tab.

*Primary Examiner* — Jerry D Johnson

(57) ABSTRACT

Compounds effective in inhibiting replication of Hepatitis C virus ("HCV") are described. This invention also relates to processes of making such compounds, compositions comprising such compounds, and methods of using such compounds to treat HCV infection.

At the time of issuance and publication of this certificate, the patent remains subject to pending reissue application number 16/874,444 filed May 14, 2020. The claim content of the patent may be subsequently revised if a reissue patent is issued from the reissue application.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 3, lines 38-40:

$R_A$ is independently selected at each occurrence from halogen, hydroxy, mercapto, amino, carboxy, nitro, phosphate, oxo, thioxo, formyl, cyano, —$L_A$, or [—$L_S R_B$] —$L_S R_E$;

Column 15, lines 34-50:

$R_2$ is —$N(R_B)C(O)C(R_5 R_6)N(R_8)$-T-$R_D$,

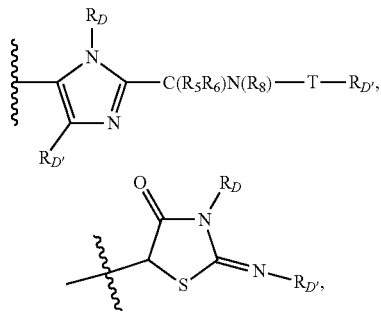

or —$L_K B$;

AS A RESULT OF REEXAMINATION, IT HAS BEEN DETERMINED THAT:

Claims 1-26 are cancelled.

New claims 27-32 are added and determined to be patentable.

27. *A compound of Formula I, or a pharmaceutically acceptable salt thereof,*

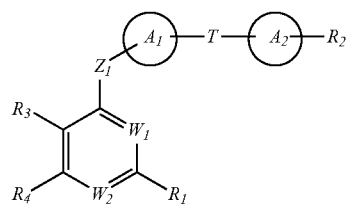

*wherein:*
*$W_1$ and $W_2$ are each N or are each $C(R_D)$, wherein $R_D$ is hydrogen;*
*$R_1$ and $R_4$ are hydrogen; and*

*$R_3$ is $R_A$, wherein $R_A$ is —$L_S$—$R_E$, wherein $L_S$ is a bond, $R_E$ is —$SO_2 N(R_S R_{S'})$, and $R_S$ and $R_{S'}$ are each $C_1$-$C_6$ alkyl;*
*or $R_1$ is hydrogen, and $R_3$ and $R_4$, taken together with the carbon atoms to which they are attached, form a 5- to 10-membered heterocyclic ring, wherein said 5- to 10-membered heterocyclic ring is optionally substituted with one or more $R_A$, wherein $R_A$ is $L_A$, and $L_A$ is $C_1$-$C_6$ alkyl;*
*$A_1$ is $C_3$-$C_{14}$ carbocyclyl or 3- to 14-membered heterocyclyl, and is substituted with —$X_1 R_7$, wherein said $C_3$-$C_{14}$ carbocyclyl and 3- to 14-membered heterocyclyl are optionally substituted with one $R_A$ wherein $R_A$ is halogen;*
*$X_1$ is a bond or —S—;*
*$R_7$ is hydrogen or $C_5$-$C_{10}$ carbocyclyl, wherein said $C_5$-$C_{10}$ carbocyclyl is optionally substituted with one or more $R_A$, wherein $R_A$ is amino or $L_S R_E$, wherein $L_S$ is a bond, $R_E$ is —$OR_S$, and $R_S$ is $C_1$-$C_6$ alkyl;*
*$Z_1$ is —$N(R_B)$—, wherein $R_B$ is hydrogen;*
*T is a bond; —$L_S$—, wherein $L_S$ is $C_{2-6}$ alkynylene; or —$L_S$—M—$L_{S'}$—, wherein $L_S$ and $L_{S'}$ are each a bond and wherein M is —$N(R_B)$— or —$C(O)N(R_B)$—, wherein $R_B$ is hydrogen;*
*$A_2$ is $C_3$-$C_{14}$ carbocyclyl;*
*$R_2$ is —$L_K$—B;*
*$L_K$ is $C_1$-$C_6$ alkylene or —$N(R_B)C(O)$—, wherein $R_B$ is H; and*
*B is 3- to 10-membered heterocycle substituted with one $R_A$, wherein $R_A$, when substituted on B, is —$L_A$ or —$L_S R_E$, wherein $L_A$ is $C_1$-$C_6$ alkyl, $L_S$ is a bond, $R_E$ is —$C(O)R_S$ or —$C(O)OR_S$, and $R_S$ is $C_3$-$C_6$ carbocyclyl$C_1$-$C_6$ alkyl optionally substituted with —$NR_B R_{B'}$, wherein $R_B$ and $R_{B'}$ are each $C_{1-6}$ alkyl.*

28. *The compound of claim 27, or a pharmaceutically acceptable salt thereof, wherein:*
*$R_7$ is hydrogen or $C_5$-$C_{10}$ carbocyclyl, wherein said $C_5$-$C_{10}$ carbocyclyl is substituted with one $R_A$, wherein $R_A$ is amino;*
*T is a bond or —$L_S$—M—$L_{S'}$—, wherein $L_S$ and $L_{S'}$ are each a bond, and M is —$N(R_B)$—or —$C(O)N(R_B)$—, wherein $R_B$ is hydrogen; and*
*B is 3- to 10-membered heterocycle substituted with one $R_A$, wherein $R_A$, when substituted on B, is —$L_A$ or —$L_S R_E$, wherein $L_A$ is $C_1$-$C_6$ alkyl, $L_S$ is a bond, $R_E$ is —$C(O)OR_S$, and $R_S$ is $C_3$-$C_6$ carbocyclyl$C_1$-$C_6$ akyl.*

29. *The compound of claim 28, or a pharmaceutically acceptable salt thereof, wherein:*
*T is a bond or —$L_S$—M—$L_{S'}$—, wherein $L_S$ and $L_{S'}$ are each a bond, and M is —$N(R_B)$—, wherein $R_B$ is hydrogen; and*
*$A_2$ is phenyl.*

30. *The compound of claim 29, or a pharmaceutically acceptable salt thereof, wherein:*
*$W_1$ and $W_2$ are each $C(R_D)$, wherein $R_D$ is hydrogen;*
*$R_1$ and $R_4$ are hydrogen;*
*$R_3$ is $R_A$, wherein $R_A$ is —$L_S$—$R_E$, wherein $L_S$ is a bond, $R_E$ is —$SO_2 N(R_S R_{S'})$, and $R_S$ and $R_{S'}$ are each $C_{1-6}$ alkyl;*
*$A_1$ is 3- to 14-membered heterocyclyl substituted with —$X_1$-$R_7$ and further substituted with one $R_A$, wherein $R_A$ is halogen;*
*$X_1$ is a bond;*
*$R_7$ is hydrogen;*
*T is —$L_S$—M—$L_{S'}$—, wherein $L_S$ and $L_{S'}$ are each a bond, and M is —$N(R_B)$—, wherein $R_B$ is hydrogen;*
*$L_K$ is $C_{1-6}$ alkylene; and*

B is 3- to 10-membered heterocycle substituted with one $R_A$, wherein $R_A$, when substituted on B, is —$L_A$, wherein $L_A$ is $C_{1-6}$alkyl.

31. The compound of claim 27, or a pharmaceutically acceptable salt thereof, wherein:

$R_1$ and $R_4$ are hydrogen; and $R_3$ is $R_A$, wherein $R_A$ is —$L_S$—$R_E$, wherein $L_S$ is a bond, $R_E$ is —$SO_2N(R_S R_{S'})$, and $R_S$ and $R_{S'}$ are each methyl;

or $R_1$ is hydrogen, and $R_3$ and $R_4$, taken together with the carbon atoms to which they are attached, form a pyridinyl ring, wherein said pyridinyl ring is substituted with one $R_A$, wherein $R_A$ is $L_A$, and $L_A$ is isopropyl;

$A_1$ is phenyl or pyrimidinyl, and is substituted with —$X_1$-$R_7$, wherein said pyrimidinyl is substituted with one $R_A$ wherein $R_A$ is halogen;

$R_7$ is hydrogen or phenyl, wherein said phenyl is substituted with one $R_A$, wherein $R_A$ is amino;

T is a bond or —$L_S$—M—$L_{S'}$—, wherein $L_S$ and $L_{S'}$ are each a bond, and M is —$N(R_B)$—, wherein $R_B$ is hydrogen;

$A_2$ is phenyl;

$L_K$ is —$CH_2$— or —$N(R_B)C(O)$—, wherein $R_B$ is H; and

B is pyrrolidinyl or piperazinyl substituted with one $R_A$, wherein $R_A$, when substituted on B, is —$L_A$ —or —$L_S R_E$, wherein $L_A$ is methyl, and wherein $L_S$ is a bond, $R_E$ is —C(O)$OR_S$, and $R_S$ is $C_3$-$C_6$carbocyclyl$C_1$-$C_6$alkyl.

32. The compound of claim 27, or a pharmaceutically acceptable salt thereof, wherein:

$W_1$ and $W_2$ are each $C(R_D)$, wherein $R_D$ is hydrogen;

$R_3$ is $R_A$, wherein $R_A$ is —$L_S$—$R_E$, wherein $L_S$ is a bond, $R_E$ is —$SO_2N(R_S R_{S'})$, and $R_S$ and $R_{S'}$ are each methyl;

$A_1$ is pyrimidinyl substituted with —$X_1$-$R_7$, and further substituted with one $R_A$, wherein $R_A$ is halogen;

$X_1$ is a bond;

$R_7$ is hydrogen;

T is —$L_S$—M—$L_{S'}$, wherein $L_S$ and $L_{S'}$ are each a bond, and M is —$N(R_B)$—, wherein $R_B$ is hydrogen;

$A_2$ is phenyl;

$L_K$ is —$CH_2$—; and

B is piperazinyl substituted with one $R_A$, wherein $R_A$, when substituted on B, is —$L_A$, wherein $L_A$ is methyl.

* * * * *